(12) United States Patent
Moore et al.

(10) Patent No.: US 7,407,776 B2
(45) Date of Patent: Aug. 5, 2008

(54) ENGINEERED ZINC FINGER PROTEINS FOR REGULATION OF GENE EXPRESSION

(75) Inventors: Michael Moore, London (GB); Yen Choo, London (GB); Aaron Klug, Cambridge (GB)

(73) Assignee: Sangamo Biosciences, Inc., Richmond, CA (US)

( * ) Notice: Subject to any disclaimer, the term of this patent is extended or adjusted under 35 U.S.C. 154(b) by 60 days.

(21) Appl. No.: 10/572,886

(22) PCT Filed: Sep. 17, 2004

(86) PCT No.: PCT/US2004/030606

§ 371 (c)(1),
(2), (4) Date: Oct. 3, 2006

(87) PCT Pub. No.: WO2005/028630

PCT Pub. Date: Mar. 31, 2005

(65) Prior Publication Data

US 2007/0059795 A1 Mar. 15, 2007

Related U.S. Application Data

(60) Provisional application No. 60/504,502, filed on Sep. 19, 2003.

(51) Int. Cl.
C12P 21/06 (2006.01)
C07K 14/00 (2006.01)
(52) U.S. Cl. .................. 435/69.1; 536/23.1; 530/350
(58) Field of Classification Search .............. 530/350; 536/23.1; 435/69.1
See application file for complete search history.

(56) References Cited

U.S. PATENT DOCUMENTS

| | | | |
|---|---|---|---|
| 4,186,183 A | 1/1980 | Steck et al. |
| 4,217,344 A | 8/1980 | Vanlerberghe et al. |
| 4,235,871 A | 11/1980 | Papahadjopolous et al. |
| 4,261,975 A | 4/1981 | Fullerton et al. |
| 4,485,054 A | 11/1984 | Mezei et al. |
| 4,501,728 A | 2/1985 | Geho et al. |
| 4,603,044 A | 7/1986 | Geho et al. |
| 4,774,085 A | 9/1988 | Fidler |
| 4,797,368 A | 1/1989 | Carter et al. |
| 4,837,028 A | 6/1989 | Allen |
| 4,897,355 A | 1/1990 | Eppstein et al. |
| 4,946,787 A | 8/1990 | Eppstein et al. |

(Continued)

FOREIGN PATENT DOCUMENTS

WO    WO 91/16024 A1    10/1991

(Continued)

OTHER PUBLICATIONS

Ahmad et al., "Antibody-Medicated Specific Binding and Cytotoxicity of Liposome-Entrapped Doxorubicin to Lung Cancer Cells In Vitro," Cancer Res 52(17):4817-4820 (1992).

(Continued)

*Primary Examiner*—Karen Cochrane Carlson
(74) *Attorney, Agent, or Firm*—Robins & Pasternak LLP

(57) ABSTRACT

Disclosed herein are methods and compositions for modulation of gene expression, with single-gene specificity, in a human-sized genome.

10 Claims, 15 Drawing Sheets

U.S. PATENT DOCUMENTS

| | | | |
|---|---|---|---|
| 4,957,773 | A | 9/1990 | Spencer et al. |
| 5,049,386 | A | 9/1991 | Eppstein et al. |
| 5,173,414 | A | 12/1992 | Lebkowski et al. |
| 5,176,996 | A | 1/1993 | Hogan et al. |
| 5,272,071 | A | 12/1993 | Chappel |
| 5,356,802 | A | 10/1994 | Chandrasegaran |
| 5,364,791 | A | 11/1994 | Vegeto et al. |
| 5,422,251 | A | 6/1995 | Fresco |
| 5,436,150 | A | 7/1995 | Chandrasegaran |
| 5,487,994 | A | 1/1996 | Chandrasegaran |
| 5,585,245 | A | 12/1996 | Nils et al. |
| 5,789,538 | A | 8/1998 | Rebar et al. |
| 5,792,640 | A | 8/1998 | Chandresegaran |
| 5,834,266 | A | 11/1998 | Crabtree et al. |
| 5,874,534 | A | 2/1999 | Vegeto et al. |
| 5,916,794 | A | 6/1999 | Chandresegaran |
| 5,925,523 | A | 7/1999 | Dove et al. |
| 5,935,934 | A | 8/1999 | Vegeto et al. |
| 5,994,313 | A | 11/1999 | Crabtree et al. |
| 6,007,988 | A | 12/1999 | Choo et al. |
| 6,013,453 | A | 1/2000 | Choo et al. |
| 6,140,081 | A | 10/2000 | Barbas |
| 6,200,759 | B1 | 3/2001 | Dove et al. |
| 6,265,196 | B1 | 7/2001 | Chandrasegeren |
| 6,270,990 | B1 | 8/2001 | Anderson et al. |
| 6,453,242 | B1 | 9/2002 | Eisenberg et al. |
| 6,534,261 | B1 | 3/2003 | Cox et al. |
| 6,607,882 | B1 | 8/2003 | Cox et al. |

FOREIGN PATENT DOCUMENTS

| | | |
|---|---|---|
| WO | WO 91/17424 A1 | 11/1991 |
| WO | WO 93/24641 A2 | 2/1993 |
| WO | WO 94/18313 A1 | 8/1994 |
| WO | WO 94/26877 A1 | 11/1994 |
| WO | WO 95/19431 A1 | 7/1995 |
| WO | WO 96/06166 A1 | 2/1996 |
| WO | WO 98/44350 A1 | 10/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 99/10508 A1 | 3/1999 |
| WO | WO 99/27092 A1 | 6/1999 |
| WO | WO 00/27878 A1 | 5/2000 |
| WO | WO 01/04296 A1 | 1/2001 |
| WO | WO 01/53480 A1 | 7/2001 |
| WO | WO 01/60970 A2 | 8/2001 |
| WO | WO 01/83793 A2 | 11/2001 |
| WO | WO 01/88197 A2 | 11/2001 |
| WO | WO 02/26959 A2 | 4/2002 |
| WO | WO 02/26960 A2 | 4/2002 |
| WO | WO 02/44376 A2 | 6/2002 |
| WO | WO 02/44386 A2 | 6/2002 |
| WO | WO 02/077227 A2 | 10/2002 |
| WO | WO 02/099084 A2 | 12/2002 |
| WO | WO 03/016496 A2 | 2/2003 |
| WO | WO 03/087341 A2 | 10/2003 |
| WO | WO 2005/014791 A2 | 2/2005 |
| WO | WO 2005/116060 A1 | 12/2005 |

OTHER PUBLICATIONS

Ahn et al., "Threonine 68 Phosphorylation by Ataxia Telangiectasia Mutated is Required for Efficient Activation of CHK2 in Response to Ionizing Radiation," Cancer Res 60:5934-5936 (2000).

Altincicek et al., "Interaction of the Corepressor Alien With DAX-1 is Abrogated by Mutations of DAX-1 Involved in Adrenal Hypoplasia Congenital," J. Biol. Chem. 275(11):7662-7667 (2000).

Alvarez et al. "A Phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients," Hum. Gene Ther. 8(5):597-613 (1997).

Anderson, "Human Gene Therapy," Science 256(5058):808-813 (1992).

Arora et al., "Residues 1-254 of Anthrax Toxin Lethal Factor are Sufficient to Cause Cellular Uptake of Fused Polypeptides," J. Biol. Chem. 268(5):3334-3341 (1993).

Aso et al., "Transcription Syndromes and the Role of RNA Polymerase II General Transcription Factors in Human Disease," J. Clin. Invest. 97:1561-1569 (1996).

Ayer et al., "Mad Proteins Contain a Dominant Transcription Repression Domain," Mol. Cell. Biol. 16(10):5772-5781 (1996).

Ballard et al., "The 65-KDA Subunit of Human NF-{KAPPA}B Functions as a Potent Transcriptional Activator and a Target for V-Rel-Mediated Repression," PNAS USA 89:1875-1879 (1992).

Barahmand-Pour et al., "A Role for Stat Family Transcription Factors in Myeloid Differentiation," Curr Top Microbiol Immunol 211:121-128 (1996).

Barnes & Adcock "Transcription Factors," Clin Exp Allergy 2:46-49 (1995).

Bartek et al., "CHK2 Kinase—A Busy Messenger," Nat Rev Mol Cell Biol 2:877-886 (2001).

Bartsevich et al., "Regulation of the MDRI Gene by Transcriptional Repressors Selected Using Peptide Combinatorial Libraries," Mol Pharmacol 58:1-10 (2000).

Batzer et al., "Enhanced Evolutionary PCR Using Oligonucleotides With Inosine at the 3'—Terminus," Nucleic Acid Res. 19:5081 (1991).

Beerli et al., "Positive and Negative Regulation of Endogenous Genes by Designed Transcription Factors," PNAS 97: 1495-1500 (2000).

Behr et al., "Gene Transfer With Synthetic Cationic Amphiphiles: Prospects for Gene Therapy," Bioconjug. Chem. 5(5):382-389 (1994).

Berg et al., "The Galvanization of Biology: A Growing Appreciation for the Roles of Zinc," Science 271: 1081-1085 (1996).

Beug et al., "Avian Erythropoiesis and Erythroleukemia: Towards Understanding the Role of the Biomolecules Involved," Biochim. Biophys. Acta 1288(3):M35-47 (1996).

Bird et al., "Methylation-Induced Repression—Belts, Braces, and Chromatin," Cell 99(5):451-454 (1999).

Bitko & Barik, "Persistent Activation of Rela by Respiratory Syncytial Virus Involves Protein Kinase C, Underphosphorylated Ikappabbeta, and Sequestration of Protein Phosphatase 2A by the Viral Phosphoprotein," J. Virol. 72(7):5610-5618 (1998).

Blaese et al., "Vectors in Cancer Therapy: How Will They Deliver?" Cancer Gene Therapy 2:291-297 (1995).

Blaese et al., "T Lymphocyte-Directed Gene Therapy for ADA-SCID: Initial Trial Results After 4 Years," Science 270(5235):475-480 (1995).

Boulikas, "Phosphorylation of Transcription Factors and Control of the Cell Cycle," Crit Rev Eukaryot. Gene Expr. 5(1):1-77 (1995).

Buchscachher et al., "Human Immunodeficiency Virus Vectors for Inducible Expression of Foreign Genes," J Virol 66(5):2731-2739 (1992).

Burley et al., "The TATA Binding Protein," Curr. Opin. Struct. Biol. 6:69-75 (1996).

Capecchi et al., "Altering the Genome by Homologous Recombination," Science 244:1288-1292 (1989).

Carbonetti et al., "Use of Purtussis Toxin Vaccine Molecule PT9K/129G to Deliver Peptide Epitopes for Stimulation of a Cytotoxic T Lymphocyte Response," Abstr. Annu. Meet. Am. Soc. Microbiol. 95:295 (1995).

Carreira et al., "Brachyury-Related Transcription Factor TBX2 and Repression of the Melanocyte-Specific TRP-1 Promoter," Mol. Cell. Biol. 18(9):5099-5108 (1998).

Chehab et al., "CHK2/HCDS1 Functions as a DNA Damage Checkpoint in G1 by Stabilizing P53," Genes Dev 14:278-288 (2000).

Cheng, "DNA Modification by Methyltransferases," Curr. Opin. Struct. Biol. 5(1):4-10 (1995).

Chern et al., "The Regulator of MAT2 (ROM2) Protein Binds to Early Maturation Promoters and Represses PVALF-Activated Transcription," Plant Cell 8(2):305-321 (1996).
Cho et al., "Analysis of the C-Terminal Region of Arabidopsis Thaliana Apetalai as a Transcription Activation Domain," Plant Mol. Biol. 40(3):419-429 (1999).
Cho et al., "Antisense DNAS as Multisite Genomic Modulators Identified by DNA Microarray," PNAS USA 98:9819-9823 (2001).
Choo et al., "Toward a Code for the Interactions of Zinc Fingers With DNA: Selection of Randomized Fingers Displayed on Phage," PNAS 91: 11163-11167 (1994).
Choo et al., "Selection of DNA Binding Sites for Zinc Fingers Using Randomized DNAS Reveals Coded Interactions," PNAS 91: 11168-11172 (1994).
Ciana et al., "Leukemic Transformation by the V-Erba Oncoprotein Entails Constitutive Binding to and Repression of an Erythroid Enhancer In Vivo," EMBO J. 17(24):7382-7394 (1998).
Clarke-Curtiss & Curtiss, "Analysis of Recombinant DNA Using *Escherichia coli* Minicells," Methods in Enzymology 101:347-362 (1983).
Colley et al., "Conversion of a Golgi Apparatus Sialyltransferase to a Secretory Protein by Replacement of the NH2-Terminal Signal Anchor With a Signal Peptide," J. Biol. Chem. 264(30):17619-17622 (1989).
Collingwood et al., "Nuclear Receptors: Coactivators, Corepressors and Chromatin Remodeling in the Control of Transcription," J. Mol. Endocrinol. 23(3):255-275 (1999).
Cook et al., "Three Conserved Transcriptional Repressor Domains are a Defining Feature of the Tieg Subfamily of SP1-Like Zinc Finger Proteins," J. Biol. Chem. 274(41):29500-29504 (1999).
Crepieux et al., "The ETS Family of Proteins: Weak Modulators of Gene Expression in Quest for Transcriptional Partners," Crit. Rev. Oncog. 5(6):615-638 (1994).
Crystal, "Transfer of Genes to Humans: Early Lessons and Obstacles to Success," Science 270(5235):404-410 (1995).
Cultraro, et al., "Function of the C-MYC Antagonist MAD1 During a Molecular Switch From Proliferation to Differentiation," Mol Cell. Biol. 17(5):2353-2359 (1997).
Damm et al., "Protein Encoded by V-Erba Functions as a Thyroid-Hormone Receptor Antagonist," Nature 339:593-597 (1989).
Deamer & Bangham, "Large Volume Liposomes by an Ether Vaporization Method," Biochim. Biophys. Acta 443(3):629-634 (1976).
Desjarlais et al., "Toward Rules Relating Zinc Finger Protein Sequences and DNA Binding Site Preferences," PNAS USA 89:7345-7349 (1992).
Desjarlais et al., "Use of a Zinc-Finger Consensus Sequences Framework and Specificity Rules to Design Specific DNA Binding Proteins" PNAS 90: 2256-2260 (1993).
Desjarlais et al., "Length-Encoded Multiplex Binding Site Determination: Application to Zinc Finger Proteins," PNAS 91: 11099-11103 (1994).
Denisenko et al., "Point Mutations in the WD40 Domain of EED Block its Interaction With EZH2," Mol. Cell. Biol. 18(10):5634-5642 (1998).
Derossi et al., "The Third Helix of the Antennapedia Homeodomain Translocates Through Biological Membranes," J. Biol. Chem. 269(14):10444-10450 (1994).
Dillon, "Regulating Gene Expression in Gene Therapy," TIBTECH 11(5):167-175 (1993).
Doench et al., "Sirnas can Function as Mirnas," Genes Dev 17:438-442 (2003).
Donelly et al., "Targeted Delivery of Peptide Epitopes to Class I Major Histocompatibility Molecules by a Modified Pseudomonas Exotoxin," PNAS 90(8):3530-3534 (1993).
Doyle & Hunt, "Reduced Nuclear Factor KAPPAB (P65) Expression in Rat Primary Sensory Neurons After Peripheral Nerve Injury," Neuroreport 8(13):2937-2942 (1997).
Dranoff et al., "A Phase I Study of Vaccination With Autologous, Irradiated Melanoma Cells Engineered to Secrete Human Granulocyte-Macrophage Colony Stimulating Factor," Hum Gene Ther. 8(1):111-112 (1997).
Eisenberg et al., "Promoter Domains Required for Expression of Plasmid-Borne Copies of the Herpes Simplex Virus Thymidine Kinase Gene in Virus-Infected Mouse Fibroblasts and Microinjected Frog Oocytes," Mol. Cell. Biol. 5:1940-1947 (1985).
Ellem et al., "A Case Report: Immune Responses and Clinical Course of the First Human Use of Granulocyte/Macrophage-Colony-Stimulating-Factor-Transduced Autologous Melanoma Cells for Immunotherapy," Cancer Immunol Immunother. 44(1):10-20 (1997).
Elliott & O'Hare, "Intercellular Trafficking and Protein Delivery by a Herpesvirus Structural Protein," Cell 88(3):223-233 (1997).
Epstein et al., "Tumor-Specific PAX3-FKHR Transcription Factor, but not PAX3, Activates the Platelet-Derived Growth Factor Alpha Receptor," Mol. Cell. Biol. 18:4118-4130 (1998).
Evans, "The V-Erba Oncogene is a Thyroid Hormone Receptor Antagonist," Int. J. Cancer Suppl. 4:26-28 (1989).
Fahraeus et al., "Inhibition of PRB Phosphorylation and Cell-Cycle Progression by a 20-Residue Peptide Derived From P16CDKN2/INK4A," Current Biology 6:84 (1996).
Fields et al., "A Novel Genetic System to Detect Protein-Protein Interactions," Nature 340:245-246 (1989).
Fisher et al., "The WRPW Motif of the Hairy-Related Basic Helix-Loop-Helix Repressor Proteins Acts as a 4-Amino-Acid Transcription Repression and Protein-Protein Interaction Domain," Mol. Cell. Biol. 16:2670-2677 (1996).
Flynn et al., "DNA Binding Discrimination of the Murine DNA Cytosine-C5 Methyltransferase," J. Mol. Biol. 279:101-116 (1998).
Fondell et al., "Unliganded Thyroid Hormone Receptor Inhibits Formation of a Functional Preinitiation Complex: Implications for Active Repression," Genes Dev 7:1400-1410 (1993).
Fondell et al., "Unliganded Thyroid Hormone Receptor Alpha Can Target TATA-Binding Protein for Transcriptional Repression," Mol. Cell. Biol. 16:281-287 (1996).
Fraley et al., "Entrapment of a Bacterial Plasmid in Phospholipid Vesicles: Potential for Gene Transfer," PNAS 76:3348-3352 (1979).
Fraley et al., "Expression of Bacterial Genes in Plant Cells," PNAS USA 80:4803-4807 (1983).
Friedman et al., "KAP-1, A Novel Corepressor for the Highly Conserved KRAB Repression Domain," Genes Dev 10:2067-2078 (1996).
Fromm et al., "Expression of Genes Transferred Into Monocot and Dicot plant Cells by Electroporation," PNAS USA 82:5824-5828 (1985).
Gangloff et al., "Transcription, Topoisomerases and Recombination," Experientia 50:261-269 (1994).
Gao et al., "Cationic Liposome-Mediated Gene Transfer," Gene Therapy 2:710-722 (1995).
Garcia et al., "RYBP, A New Repressor Protein That Interacts With Components of the Mammalian Polycomb Complex, and With the Transcription Factor YY1," EMBO J 18(12):3404-3418 (1999).
Ginsberg et al., "Up-Regulation of MET but not Neural Cell Adhesion Molecule Expression by the PAX3-FKHR Fusion Protein in Alveolar Rhabdomyosarcoma," Cancer Res 58(16):3542-3546 (1998).
Goff et al., "Identification of Functional Domains in the Maize Transcriptional Activator C1: Comparison of Wild-Type and Dominant Inhibitor Proteins," Genes Dev. 5(2):298-309 (1991).
Gong et al., "A Constitutively Expressed MYC-Like Gene Involved in Anthocyanin Biosynthesis From Perilla Frutescens: Molecular Characterization, Heterologous Expression in Transgenic Plants and Transactivation in Yeast Cells," Plant Mol. Biol. 41(1):33-44 (1999).
Goodrich et al., "Contacts in Context: Promoter Specificity and Macromolecular Interactions in Transcription," Cell 84:825-830 (1996).
Goodrich & Tijian, "TBP-TAF Complexes: Selectivity Factors for Eukaryotic Transcription," Curr. Opin. Cell Biol. 6(3):403-409 (1994).
Gossen & Bujard "Tight Control of Gene Expression in Mammalian Cells by Tetracycline-Responsive Promoters," PNAS USA 89:5547 (1992).
Greisman et al., "A General Strategy for Selecting High-Affinity Zinc Finger Proteins for Diverse DNA Target Sites," Science 275:657-661 (1997).

Guenther et al., "A Core SMRT Corepressor Complex Containing HDAC3 and TBL1, A WD40-Repeat Protein Linked to Deafness," Genes Dev. 14:1048-1057 (2000).

Gunster et al., "Identification and Characterization of Interactions Between the Vertebrate Polycomb-Group Protein BMI1 and Human Homologs of Polyhomeotic," Mol. Cell. Biol. 17:2326-2335 (1997).

Gupta et al., "MMIP1: A Novel Leucine Zipper Protein That Reverses the Suppressive Effects of MAD Family Members on C-MYC," Oncogene 16:1149-1159 (1998).

Hagmann et al., "The VP16 Paradox: Herpes Simplex Virus VP16 Contains a Long-Range Activation Domain but Within the Natural Multiprotein Complex Activates Only From Promoter-Proximal Positions," J. Virol. 71:5952-5962 (1997).

Han et al., "Ligand-Directed Retroviral Targeting of Human Breast Cancer Cells," PNAS USA 92:9747-9751 (1995).

Hassig et al., "Transcription Repression by Xenopus Et and Its Human Ortholog TBX3, A Gene Involved in Ulnar-Mammary Syndrome," PNAS 95:3519-3524 (1998).

He et al., "Transcription Repression by Xenopus Et and Its Human Ortholog TBX3, A Gene Involved in Ulnar-Mammary Syndrome," PNAS USA 96:10,212-10,217 (1999).

Hemenway et al., "The BMI-1 Oncoprotein Interacts With Ding and MPH2: The Role of Ring Finger Domains," Oncogene 16:2541-2547 (1998).

Hendrich et al., "Genomic Structure and Chromosomal Mapping of the Murine and Human MBD1, MBD2, MBD3, and MBD4 Genes," Mamm Genome 10:906-912 (1999).

Heppard et al., "Developmental and Growth Temperature Regulation of Two Different Microsomal [Omega]-6 Desaturase Genes in Soybeans," Plant Physiol 110:311-319 (1996).

Hermonat et al., "Use of Adeno-Associated Virus as a Mammalian DNA Cloning Vector: Transduction of Neomycin Resistance Into Mammalian Tissue Culture Cells," PNAS 81:6466-6470 (1984).

Hirao et al., "DNA Damage-Induced Activation of P53 by the Checkpoint Kinase CHK2," Science 287:1824-1827 (2000).

Ho et al., "Dimeric Ligands Define a Role for Transcriptional Activation Domains in Reinitiation," Nature 382:822-826 (1996).

Hobo et al., "A BZIP Factor, TRAB1, Interacts With VP1 and Mediates Abscisic Acid-Induced Transcription," PNAS USA 96:15,348-15,353 (1999).

Hope et al., "Production of Large Unilamellar Vesicles by a Rapid Extrusion Procedure. Characterization of Size Distribution, Trapped Volume and Ability to Maintain a Memgrane Potential," Biochim. Biophys. Acta 812:55-65 (1985).

Hope et al., "Generation of Multilamellar and Unilamellar Phospholipid Vesicles," Chem. Phys. Lip. 40:89-107 (1986).

Horsch et al., "Inheritance of Functional Foreign Genes in Plants," Science 233:496-498 (1984).

Hurlin et al., "The Max Transcription Factor Network: Involvement of MAD in Differentiation and an Approach to Identification of Target Genes," Cold Spring Harb. Symp. Quant. Biol. 59:109-116 (1994).

Inaba et al., "Generation of Large Numbers of Dendritic Cells From Mouse Bone Marrow Cultures Supplemented With Granulocyte/Macrophage Colony-Stimulating Factor," J Exp Med 176:1693-1702 (1992).

Isalan et al., "A Rapid, Generally Applicable Method to Engineer Zinc Fingers Illustrated by Targeting the HIV-1 Promoter," Nat Biotechnol 19:656-660 (2001).

Jackson et al., "Phosphorylation of Transcription Factor SP1 by the DNA-Dependent Protein Kinase," Adv. Second Messenger Phosphoprotein Res. 28:279-286 (1993).

Jackson et al., "Expression Profiling Reveals Off-Target Gene Regulation by RNAI," Nat Biotechnol 21:635-637 (2003).

Jacobs, G. H., "Determination of the Base Recognition Positions of Zinc Fingers From Sequence Analysis," EMBO J. 11(12):4507-4517 (1992).

Jamieson et al., "In Vitro Selection of Zinc Fingers With Altered DNA-Binding Specificity," Biochemistry 33:5689-5695 (1994).

Jamieson et al., "Drug Discovery With Engineered Zinc Finger Proteins," Nat Rev Drug Discov 2:361-368 (2003).

Jin & Scotto, "Transcriptional Regulation of the MDR1 Gene by Histone Acetyltransferase and Deacetylase is Mediated by NF-Y," Mol. Cell. Biol. 18:4377-4384 (1998).

Johann et al., "GLVR1, A Receptor for Gibbon Ape Leukemia Virus, is Homologous to a Phosphate Permease of Neurospora Crassa and is Expressed at High Levels in the Brain and Thymus," J Virol 66:1635-1640 (1992).

Jones et al., "Replacing the Complementarity-Determining Regions in a Human Antibody With Those From a Mouse," Nature 321: 522-525 (1986).

Khanna et al., "ATM Associates With and Phosphorylates P53: Mapping the Region of Interaction," Nat Genet 20:398-400 (1998).

Kaiser et al., "The Human General Co-Factors," Trends Biochem. Sci. 21:342-345 (1996).

Kanei-Ishii et al., "Structure and Function of the Proteins Encoded by the MYB Gene Family," Curr. Top. Microbiol. Immunol. 211:89-98 (1996).

Kearns et al., "Recombinant Adeno-Associated Virus (AAV-CFTR) Vectors do not Integrate in a Site-Specific Fashion in an Immortalized Epithelial Cell Line," Gene Ther. 9:748-755 (1996).

Kim et al., "Hybrid Restriction Enzymes: Zinc Finger Fusions FOK 1 Cleavage Domain," PNAS 93: 1156-1160 (1996).

Kim et al., "Transcriptional Repression by Zinc Finger Peptides. Exploring the Potential for Applications in Gene Therapy" J. Biol. Chem. 272: 29795-29800 (1997).

Kim et al., "TIN2, A New Regulator of Telomere Length in Human Cells," Nat Genet. 23:405-412 (1999).

Klee et al., "Agrobacterium-Mediated Plant Transformation and its Further Applications to Plant Biology," Ann. Rev. of Plant Phys. 38:467-486 (1987).

Klein et al., "High-Velocity Microprojectiles for Delivering Nucleic Acids into Living Cells," Nature 327:70-73 (1987).

Klemm et al., "Dimerization as a Regulatory Mechanism in Signal Transduction," Annu Rev Immunol 16:569-592 (1998).

Klimpel et al., "Anthrax Toxin Protective Antigen is Activated by a Cell Surface Protease With the Sequence Specificity and Catalytic Properties of Furin," PNAS USA 89:10277-10281 (1992).

Knoepfler et al., "SIN Meets NURD and Other Tails of Repression," Cell 99:447-450 (1999).

Kohn et al., "Engraftment of Gene-Modified Umbilical Cord Blood Cells in Neonates With Adenosine Deaminase Deficiency," Nat Med 1:1017-1102 (1995).

Kotin, "Prospects for the Use of Adeno-Associated Virus as a Vector for Human Gene Therapy," Hum. Gene Ther. 5:793-801 (1994).

Kremer & Perricaudet, "Adenovirus and Adeno-Associated Virus Mediated Gene Transfer," British Medical Bulletin 51(1):31-44 (1995).

Laherty et al., "Histone Deacetylases Associated With the MSIN3 Corepressor Mediate MAD Transcriptional Repression," Cell 89:349-356 (1997).

Lai et al., "RBP1 Induces Growth Arrest by Repression of E2F-Dependent Transcription," Oncogene 18:2091-2100 (1999).

Lai et al., "RBP1 Recruits Both Histone Deacetylase-Dependent and -Independent Repression Activities to Retinoblastoma Family Proteins," Mol. Cell. Biol. 19:6632-6641 (1999).

Lai et al., "RBP1 Recruits the MSIN3-Histone Deacetylase Complex to the Pocket of Retinoblastoma Tumor Suppressor Family Proteins Found in Limited Discrete Regions of the Nucleus at Growth Arrest," Mol. Cell. Biol. 21:2918-2932 (2001).

Lapierre et al., "Identification of a Novel Transcriptional Repressor Encoded by Human Cytomegalovirus," J. Virol. 75:6062-6069 (2001).

Larsson et al., "Analysis of the DNA-Binding Activities of MYC/MAX/MAD Network Complexes During Induced Differentiation of U-937 Monoblasts and F9 Teratocarcinoma Cells," Oncogene 15:737-748 (1997).

Lehmann, "The Molecular Biology of Nucleotide Excision Repair and Double-Strand Break Repair in Eukaryotes," Genet. Eng. 17:1-19 (1995).

Lemon et al., "Nuclear Receptor Cofactors as Chromatin Remodelers," Curr. Opin. Genet. Dev. 9:499-504 (1999).

Leo et al., "The SRC Family of Nuclear Receptor Coactivators," Gene 245:1-11 (2000).

Leonnetti et al., "Antibody-Targeted Liposomes Containing Oligodeoxyribonucleotides Complementary to Viral RNA Selectivity Inhibit Viral Replication," PNAS 87:2448-2451 (1990).

Li et al., "Both Corepressor Proteins SMRT and N-Cor Exist in Large Protein Complexes Containing HDAC3," EMBO J. 19:4342-4350 (2000).

Liang et al., "Activation of Vascular Endothelial Growth Factor a Transcription in Tumorigenic Glioblastoma Cell Lines by an Enhancer With Cell Type-Specific DNASE I Accessibility," J Biol Chem 277:20087-20094 (2002).

Lin et al., "Inhibition of Nuclear Translocation of Transcription Factor NF-KAPPA B by a Synthetic Peptide Containing a Cell Membrane-Permeable Motif and Nuclear Localization Sequence," J. Biol. Chem. 270:14255-14258 (1995).

Liu et al., "Suppression of Growth and Transformation and Induction of Apoptosis by EGR-1," Cancer Gene Ther. 5:3-28 (1998).

Liu et al., "Regulation of an Endogenous Locus Using a Oanel of Designed Zinc Finger Proteins Targeted to Accessible Chromatin Regions Activation of Vascular Endothelial Growth Factor A," J Biol Chem 276(14):11323-11334 (2001).

Liu et al., "Design of Polydactyl Zinc-Finger Proteins for Unique Addressing Within Complex Genomes," PNAS 94: 5525-5530 (1997).

Malech et al., "Prolonged Production of NADPH Oxidase-Corrected Granulocytes After Gene Therapy of Chronic Granulomatous Disease," PNAS 94(22):12133-12138 (1997).

Malik et al., "Transcriptional Regulation Through Mediator-Like Coactivators in Yeast and Metazoan Cells," Trends Biochem. Sci. 25:277-283 (2000).

Manteuffel-Cymborowska, "Nuclear Receptors, Their Coactivators and Modulation of Transcription," Acta Biochim. Pol. 46:77-89 (1999).

Margolin et al., "Kruppel-Associated Boxes are Potent Transcriptional Repression Domains," PNAS USA 91:4509-4513 (1994).

Martinez et al., "A Human SPT3-TAFII31-GCN5-L Acetylase Complex Distinct From Transcription Factor IID," J. Biol. Chem. 273:23781-23785 (1998).

Matson et al., "DNA Helicases: Enzymes With Essential Roles in All Aspects of DNA Metabolism," Bioessays 16:13-22 (1994).

Matsuoka et al., "Ataxia Telangiectasia-Mutated Phosphorylates CHK2 In Vivo and In VITro," PNAS USA 97:10389-10394 (2000).

Maxon et al., "ASHIP is a Site-Specific DNA-Binding Protein That Actively Represses Transcription," PNAS USA 98:1495-1500 (2001).

Mayer et al., "Vesicles of Variable Sizes Produced by Rapid Extrusion Procedure," Biochim. Biophys. Acta 858:161-168 (1986).

McGowan et al., "Checking in on CDSL (CHK2): A Checkpoint Kinase an Tumor Suppressor," Bioessays 24:502-511 (2002).

McKenna et al., "Nuclear Receptor Coactivators: Multiple Enzymes, Multiple Complexes, Multiple Functions," J. Steroid Biochem. Mol. Biol. 69:3-12 (1999).

Meier, "Co-Activators and Co-Repressors: Mediators of Gene Activation by Nuclear Hormone Receptors," Eur J Endocrinol 134(2):158-159 (1996).

Melchionna et al., "Threonine 68 is Required for Radiation-Induced Phosphorylation and Activation of CDS1," Nat Cell Biol 2:762-765 (2000).

Miller, "Human Gene Therapy Comes of Age," Nature 357:455-460 (1992).

Miller et al., "Construction and Properties of Retrovirus Packaging Cells Based on Gibbon Ape Leukemia Virus," J. Virol. 65:2220-2224 (1991).

Misteli & Spector, "Applications of the Green Fluorescent Protein in Cell Biology and Biotechnology," Nature Biotechnology 15:961-964 (1997).

Mitani & Caskey, "Delivering Therapeutic Genes—Matching Approach and Application," TIBTECH 11:162-166 (1993).

Moore et al., "Improved DNA Binding Specificity From Polyzinc Finger Peptides by Using Strings of Two-Finger Units," PNAS USA 98:1437-1441 (2001).

Moore et al., "Design of Polyzinc Finger Peptides With Structured Linkers," PNAS USA 98:1432-1436 (2001).

Morrison, "Transformation in *Escherichia coli*: Cryogenic Preservation of Competent Cells," J. Bact. 132:349-351 (1977).

Muzyczka, "Adeno-Associated Virus (AAV) Vectors: Will They Work?," J Clin Invest 94:1351 (1994).

Nabel & Felgner, "Direct Gene Transfer for Immunotherapy and Immunization," TIBTECH 11:211-217 (1993).

Nebert, "Transcription Factors and Cancer: An Overview," Toxicity 181-182:131-141 (2002).

Neering et al., "Transduction of Primitive Human Hematopoietic Cells With Recombinant Adenovirus Vectors," Blood 88:1147-1155 (1996).

Novak et al., "Functional Charaterization of Protease-Treated Bacillus Anthracis Protective Antigen," J. Biol. Chem. 267:17186-17193 (1992).

Ohtsuka et al., "An Alternative Approach to Deoxyoligonucleotides as Hybridization Probes by Insertion of Deoxyinosine at Ambiguous Codon Positions," J. Biol. Chem. 260:2605-2608 (1985).

Okanami et al., "Half-1, A BZIP-Type Protein, Interacting With the Wheat Transcription Factor HBP-1A Contains a Novel Transcriptional Activation Domain," Genes Cells 1:87-99 (1996).

Okano et al., "DNMT2 is not Required for De Novo and Maintenance Methylation of Viral DNA in Embryonic Stem Cells," Nucleic Acids Res. 26:2536-2540 (1998).

Oligino et al., "Drug Inducible Transgene Expression in Brain Using a Herpes Simplex Virus Vector," Gene Ther. 5:491-496 (1998).

O'Shea et al., "X-Ray Structure of the GCN4 Leucine Zipper, A Two-Stranded, Parallel Coiled Coil," Science 254:539-544 (1991).

Pain et al., "The Carbonic Anhydrase II Gene, A Gene Regulated by Thyroid Hormone and Erythropoietin, is Repressed by the V-ERBA Oncogene in Erythrocytic Cells," New Biol. 2:284-294 (1990).

Palva et al., "Secretion of Interferon by *Bacillus subtilis*," Gene 22:229-235 (1983).

Pear et al., "Production of High-Titer Helper-Free Retroviruses by Transient Transfection," PNAS USA 90:8392-8396 (1993).

Pengue et al., "Repression of Transcriptional Activity at a Distance by the Evolutionarily Conserved Krab Domain Present in a Subfamily of Zinc Finger Proteins," Nucl. Acids Res. 22:2908-2914 (1994).

Perelle et al., "Characterization of Clostridium Perfringens Iota-Toxin Genes and Expression in *Escherichia coli*," Infect. Immun. 61:5147-5156 (1993).

Pomerantz et al., "Structure-Based Design of a Dimeric Zinc Finger Protein," Biochem 37:965-970 (1998).

Pomerantz et al., "Structure-Based Design of Transcription Factors," Science 267:93-96 (1995).

Pomerantz et al., "Analysis of Homeodomain Function by Structure-Based Design of a Transcription Factor," PNAS 92: 9752-9756 (1995).

Prochiantz, "Getting Hydrophilic Compounds into Cells: Lessons From Homeopeptides," Current Opinion in Neurobiology 6:629-634 (1996).

Rebar et al., "Induction of Angiogenesis in a Mouse Model Using Engineered Transcription Factors," Nat Med 8:1427-1432 (2002).

Rebar et al, "Zinc Finger Phage: Affinity Selection of Fingers With New DNA-Binding Specifities," Science 263: 671-673 (1994).

Reid et al., "Selective Inhibition of DNA Methyltransferase Enzymes as a Novel Strategy for Cancer Treatment," Curr Opin Mol Ther 4:130-137 (2002).

Remy et al., "Gene Transfer With a Series of Lipophilic DNA-Binding Molecules," Bioconjugate Chem 5:647-654 (1994).

Ren et al., "PPARγ Knockdown by Engineered Transcription Factors: Exogenous PPARγ 2 but not PPARγ 1 Reactivates Adipogenesis," Genes Dev 16:27-32 (2002).

Rendahl et al., "Regulation of Gene Expression In Vivo Following Transduction by Two Separate RAAV Vectors," Nat. Biotechnol 16:757-761 (1998).

Renneisen et al., "Inhibition of Expression of Human Immunodeficiency Virus-1 In Vitro by Antibody-Targeted Liposomes Containing Antisense RNA to the ENV Region," J. Biol. Chem. 265:16337-16342 (1990).

Reynolds et al., "Repression of the HIV-1 5' LTR Promoter and Inhibition of HIV-1 Replication by Using Engineered Zinc-Finger Transcription Fators," PNAS USA 100:1615-1620 (2003).

Robertson et al., "DNMT1 Forms a Complex With RB, E2F1 and HDAC1 and Represses Transcription From E2F-Responsive Promoters," Nature Genet. 25:338-342 (2000).

Robyr et al., "Nuclear Hormone Receptor Coregulators in Action: Diversity for Shared Tasks," Mol. Endocrinol 14:329-347 (2000).

Roeder, "Nuclear RNA Polymerases: Role of General Initiation Factors and Confactors in Eukaryotic Transcription," Methods Enzymol 273:165-171 (1996).

Rogers et al., "Gene Transfer in Plants: Production of Transformed Plants Using T1 Plasmid Vectors," Methods Enzymol. 118:627-641 (1986).

Rosen et al., "Intracellular Receptors and Signal Transducers and Activators of Transcription Superfamilies: Novel Targets for Small-Molecule Drug Discovery," J Med Chem 38:4855-4874 (1995).

Rossolini et al., "Use of Deoxyinosine-Containing Primers vs Degenerate Primers for Polymerase Chain Reaction Based on Ambiguous Sequence Information," Mol. Cell. Probes 8:91-98 (1994).

Rubio et al., "Reversible Manipulation of Telomerase Expression and Telomere Length. Implications for the Ionizing Radiation Response and Replicative Senescence of Human Cells," J Biol Chem 277:28609-28617 (2002).

Ryan et al., "MYC Oncogenes: The Enigmatic Family," Biochem. J. 314:713-721 (1996).

Sabbattini et al., "Binding of Ikaros to the LAMBDA5 Promoter Silences Transcription Through a Mechanism That Does not Require Heterochromatin Formation," EMBO J. 20:2812-2822 (2001).

Sadowski, "Site-Specific Genetic Recombination: Hops, Flips, and Flops," FASEB J. 7:760-767 (1993).

Sakaguchi et al., "DNA Damage Activates P53 Through a Phosphorylation-Acetylation Cascade," Genes Dev. 12:2831-2841 (1998).

Satijn et al., "RING1 is Asciated With the Polycomb Group Protein Complex and Acts as a Transcriptional Repressor," Mol. Cell. Biol. 17:4105-4113 (1997).

Samulski et al., "Helper-Free Stocks of Recombinant Adeno-Associated Viruses: Normal Integration Does not Require Viral Gene Expression," J. Virol. 63:3822-3828 (1989).

Sancar, "DNA Repair in Humans," Ann. Rev. Genet. 29:69-105 (1995).

Sap et al., "Repression of Transcription Mediated at a Thyroid Hormone Response Element by the V-ERB-A Oncogene Product," Nature 340:242-244 (1989).

Schonthal, "Regulation of Gene Expression by Serine/Threonine Protein Phosphatases," Semin Cancer Biol 6:239-248 (1995).

Sebo et al., "Cell-Invasive Activity of Epitope-Tagged Adenylate Cyclase of Bordetella Pertussis Allows In Vitro Presentation of a Foreign Epitope to CD8+ Cytotoxic T Cells," Infect Immun 63:3851-3857 (1995).

Seipel et al., "Different Activation Domains Simulate Transcription From Remote ('Enhancer') and Proximal ('Promoter') Positions," EMBO J. 11:4961-4968 (1996).

Sgouras et al., "ERF: An ETS Domain Protein With Strong Transcriptional Repressor Activity, Can Suppress ETS-Associated Tumorigenesis and is Regulated by Phosphorylation During Cell Cycle and Mitogenic Stimulation," EMBO J. 14:4781-4793 (1995).

Shieh et al., "DNA Damage-Induced Phosphorylation of P53 Alleviates Inhibition by MDM2," Cell 91:325-334 (1997).

Shieh et al., "The Human Homologs of Checkpoint Kinases CHK1 and CDS1 (CHK2) Phosphorylate P53 at Multiple DNA Damage-Inducible Sites," Genes Dev 14:289-300 (2000).

Simon, "Gotta Have Gata," Nat Genet 11:9-11 (1995).

Snowden et al., "Gene-Specific Targeting of H3K9 Methylation is Sufficient for Initiating Repression In Vivo," Curr Biol 12:2159-2166 (2002).

Sommer et al., "Identification and Characterization of Specific DNA-Binding Complexes Containing Members of the MYC/MAX/MAD Network of Transcriptional Regulators," J Biol Chem 273:6632-6642 (1998).

Sommerfelt et al., "Receptor Interference Groups of 20 Retroviruses Plating on Human Cells," Virol. 176:58-59 (1990).

Sprenger-Haussels et al., "Transactivation Properties of Parsley Proline-Rich BZIP Transcription Factors," Plant J. 22:1-8 (2000).

Stenmark et al., "Peptides Fused to the Amino-Terminal End of Diptheria Toxin are Translocated to the Cytosol," J. Cell. Biol. 113:1025-1032 (1991).

Sterman et al., "Adenovirus-Mediated Herpes Simplex Virus Thymidine Kinase/Ganciclovir Gene Therapy in Patients With Localized Malignancy: Results of a Phase I Clinical Trial in Malignant Mesothelioma," Hum. Gene. Ther. 7:1083-1089 (1998).

Stunnenberg et al., "Leukemia: The Sophisticated Subversion of Hematopoiesis by Nuclear Receptor Oncoproteins," Biochim Biophys Acta, 1423(1):F15-33 (1999).

Sucov et al., "Retinoic Acid and Retinoic Acid Receptors in Development," Mol Neurobiol 10(2-3):169-184 (1995).

Syntichaki and Thireos, "The GCN5.ADA Complex Potentiates the Histone Acetyltransferase Activity of GCN5," J. Biol Chem. 273:24414-24419 (1998).

Takai et al., "HK-2 Deficient Mice Exhibit Radioresistance and Defective P53-Mediated Transcription," EMBO J. 21:5195-5205 (2002).

Taunton et al., "A Mammalian Histone Deacetylase Related to the Yeast Transcriptional Regulator RPD3P," Science 272:408-411 (1996).

Thiesen, "Multiple Genes Encoding Zinc Finger Domains are Expressed in Human T Cells," New Biologist 2:363-374 (1990).

Topf et al., "Regional 'Pro-Drug' Gene Therapy: Intravenous Administration of an Adenoviral Vector Expressing the *E. coli*Cytosine Deaminase Gene and Systemic Administration of 5-Fluorocytosine Suppresses Growth of Hepatic Metastasis of Colon Carcinoma," Gene Ther 5:507-513 (1998).

Tora et al., "The Cloned Human Oestrogen Receptor Contains a Mutation Which Alters Its Hormone Binding Properties," Embo J. 8:1981-1986 (1989).

Torchia et al., "Co-Activators and Co-Repressors in the Integration of Transcriptional Responses," Curr. Opin. Cell. Biol. 10:373-383 (1998).

Tratschin et al., "Adeno-Associated Virus Vector for High-Frequency Integration, Expression, and Rescue of Genes in Mammalian Cells," Mol. Cell. Biol. 5:3251-3260 (1985).

Tratschin et al., "A Human Parvovirus, Adeno-Associated Virus, as a Eucaryotic Vector: Transient Expression and Encapsidation of the Procaryotic Gene for Chloramphenicol Acetyltransferase," Mol. Cell Biol. 4:2072-2081 (1984).

Trimarchi et al., "The E2F6 Transcription Factor is a Component of the Mammalian BMI1-Containing Polycomb Complex," PNAS USA 98:1519-1524 (2001).

Tyler et al., "The "Dark Side" of Chromatin Remodeling: Repressive Effects on Transcription," Cell 99:443-446 (1999).

Ulmasov et al., "Activation and Repression of Transcription by Auxin-Response Factors" PNAS USA 96:5844-5849 (1999).

Uptain et al., "Basic Mechanisms of Transcript Elongation and its Regulation," Annu. Rev. Biochem. 66:117-172 (1997).

Urnov et al., "Targeting of N-COR and Histone Deacetylase 3 by the Oncoprotein V-ERBA Yields a Chromatin Infrastructure-Dependent Transcriptional Repression Pathway," EMBO J. 19:4074-4090 (2000).

Urnov et al., "Designed Transcription Factors as Tools for Therapeutics and Fucntional Genomics," Biochem Pharmacol 64:919-923 (2002).

Utley et al., "Transcriptional Activators Direct Histone Acetyltransferase Complexes to Nucleosomes," Nature 394:498-502 (1998).

Van Brunt, "Molecular Farming: Transgenic Animals as Bioreactors," Biotechnology 6(10):1149-1154 (1988).

Van den Wyngaert et al., "Cloning and Analysis of a Novel Human Putative DNA Methyltransferase," FEBS Lett. 426:283-289 (1998).

Van der Vlag et al., "Transcriptional Repression Mediated by the Human Polycomb-Group Protein EED Involves Histone Deacetylation," Nature Genet. 23:474-478 (1999).

Vigne et al., "Third-Generation Adenovectors for Gene Therapy," Restorative Neurology and Neuroscience 8:35-36 (1995).

Vissing et al., "Repression of Transcriptional Activity by Heterologus Krabdomains Present in Zinc-Finger Proteins," FEBS Lett 369:153-157 (1995).

Vos, "CIS and Trans Mechanisms of DNA Repair," Curr. Opin. Cell Biol. 4:385-395 (1992).

Wagner et al., "Efficient and Persistent Gene Transfer of AAV-CFTR in Maxillary Sinus," Lancet 351:1702-1703 (1998).

Wang, "Nuclear Protein Tyrosine Kinases," Trends Biochem. Sci. 19:373-376 (1994).

Wang et al., "Positive and Negative Regulation of Gene Expression in Eukaryotic Cells With an Inducible Transcriptional Regulator," Gene Ther. 4:432-441 (1997).

Wang et al., "A Regulatory System for Use in Gene Transfer," PNAS USA 91:8180-8184 (1994).

Wasylyk et al., "The ETS Family of Transcription Factors" Eur. J. Biochem. 211:7-18 (1993).

Wedel et al., "The C/EBP Family of Transcription Factors," Immunobiology 193:171-185 (1995).

Weising et al., "Foreign Genes in Plants—Transfer, Structure, Expression, and Application," Ann Rev Genet 22:421-477 (1988).

Weiss et al., "Gata Transcription Factors: Key Regulators of Hematopoiesis," Exp Hematol 23:99-107 (1995).

Welsh et al., "Adenovirus-Mediated Gene Transfer for Cystic Fibrosis: Part A. Safety of Dose and Repeat Administration in the Nasal Epithelium. Part B. Clinical Efficacy in the Maxillary Sinus," Hum. Gene Ther. 2:205-218 (1995).

Williams et al., "Low Density Lipoprotein Receptor-Independent Hepatic Uptake of a Synthetic, Cholesterol-Scavenging Lipoprotein: Implications for the Treatment of Receptor-Deficient Atherosclerosis," PNAS 85:242-246 (1988).

Wilson et al., "Formation of Infectious Hybrid Virions With Gibbon Ape Leukemia Virus and Human T-Cell Leukemia Virus Retroviral Envelope Glycoproteins and the GAG and POL Proteins of Moloney Murine Leukemia Virus," J Virol 63:2374-2378 (1989).

West et al., "Gene Expression in Adeno-Asociated Virus Vectors: The Effects of Chimeric MRNA Structure, Helper Virus, and Adenovirus VA1 RNA," Virology 160:38-47 (1987).

Witzgall et al., "The Kruppel-Associated Box-A (KRAB-A) Domain of Zinc Finger Proteins Mediates Transcriptional Repression," PNAS USA 91:4514-4518 (1994).

Wolffe, "Histone Deacetylase: A Regulator of Transcription," Science 272:371-372 (1996).

Wood, "DNA Repair in Eukaryotes," Ann. Rev. Biochem. 65:135-167 (1996).

Wu et al., "Building Zinc Fingers by Selection: Toward a Therapeutic Application," PNAS 92: 344-348 (1995).

Wu et al., "Functional Analysis of HD2 Histone Deacetylase Homologues in Arabidopsis Thaliana," Plant J. 22:19-27 (2000).

Yan et al., "Tissue Factor Transcription Driven by EGR-1 is a Critical Mechanism of Murine Pulmonary Fibrin Deposition in Hypoxia," PNAS USA 95:8298-8303 (1998).

Yeh et al., "Peptide-Mediated Delivery of an Artificial Transcription Factor to Upregulate Specific Endogenous Gene Expression: A Novel Approach to Gene Therapy," Molecular Therapy 7(5):S461 Abstract #1191 (2003).

Yew et al., "MOS and the Cell Cycle: The Molecular Basis of the Transformed Phenotype," Curr. Opin. Genet. Dev. 3:19-25 (1993).

Yu et al., "Progress Towards Gene Therapy for HIV Infection," Gene Therapy 1:13-26 (1994).

Zardo et al., "The Unmethylated State of CPG Islands in Mouse Fibroblasts Depends on the Poly(ADP-Ribosyl)ation Process," J. Biol. Chem. 273:16517-16520 (1998).

Zazopoulos et al., "DNA Binding and Trascriptional Repression by DAX-1 Blocks Steroidogenesis," Nature 390:311-315 (1997).

Zenke et al., "V-ERBA Specifically Suppresses Transcription of the Avian Erythrocyte Anion Transporter (BAND 3) Gene," Cell 52: 107-119 (1988).

Zenke et al., "V-ERBA Oncogene Activation Entails the Loss of Hormone-Dependent Regulator Activity of C-ERBA," Cell 61:1035-1049 (1990).

Zhang et al., "Synthetic Zinc Finger Transcription Factor Action at an Endogenous Chromosomal Site. Activation of the Human Erythropoietin Gene," Journal of Biological Chemistry 275(43): 33850-33860 (2000).

Zhang et al., "A Conserved Alpha-Helical Motif Mediates the Interaction of SP1-Like Transcriptional Repressors With the Corepressor MSIN3A," Mol. Cell. Biol. 21:5041-5049 (2001).

MAERPFQCRICMRNFS<u>RSDHLSR</u>HIRTHTGEKPFACDICGRKFA<u>DNRDRTKH</u>T
KIHTGGQRPYACPVESCDRRFS<u>DRKTLIE</u>HIRIHTGQKPFQCRICMRNFS<u>TSSG
LSR</u>HIRTHTGSQKPFQCRICMRNFS<u>RSDHLSE</u>HIRTHTGEKPFACDICGRKFA<u>T
SSDRTK</u>HTKIHLRQKDAARN

SEQ ID NO: 27

FIGURE 7

MAERPYACPVESCDRRFS<u>TSADLTE</u>HIRIHTGQKPFQCRICMRNFS<u>ASANLSR</u>HIRTHTGGERPF
QCRICMRNFS<u>RSDALST</u>HIRTHTGEKPFACDICGRKFA<u>DRSTRTK</u>HTKIHTGSQKPFQCRICMRN
FS<u>RSDVLSA</u>HIRTHTGEKPFACDICGKKFA<u>DRSNRIK</u>HTKIHLRQKDAAR (SEQ ID NO: 53)

FIG.9A

```
  1  GACGGATCGG GAGATCTCCC GATCCCCTAT GGTCGACTCT CAGTACAAATC TGCTCTGATG CCGCATAGTT
     CTGCCTAGCC CTCTAGAGGG CTAGGGGATA CCAGCTGAGA GTCATGTTAG ACGAGACTAC GGCGTATCAA
 71  AAGCCAGTAT CTGCTCCCTG CTTGTGTGTT GGAGGTCGCT GAGTAGTGCG CGAGCAAAAT TTAAGCTACA
     TTCGGTCATA GACGAGGGAC GAACACACAA CCTCCAGCGA CTCATCACGC GCTCGTTTTA AATTCGATGT
141  ACAAGGCAAG GCTTGACCGA CAATTGCATG AAGAATCTGC TTAGGGTTAG GCGTTTTGCG CTGCTTCGCG
     TGTTCCGTTC CGAACTGGCT GTTAACGTAC TTCTTAGACG AATCCCAATC CGCAAAACGC GACGAAGCGC
211  ATGTACGGGC CAGATATACG CGTTGACATT GATTATTGAC TAGTTATTAA TAGTAATCAA TTACGGGGTC
     TACATGCCCG GTCTATATGC GCAACTGTAA CTAATAACTG ATCAATAATT ATCATTAGTT AATGCCCCAG
281  ATTAGTTCAT AGCCCATATA TGGAGTTCCG CGTTACATAA CTTACGGTAA ATGCCCGCC TGGCTGACCG
     TAATCAAGTA TCGGGTATAT ACCTCAAGGC GCAATGTATT GAATGCCATT TACGGGCGG ACCGACTGGC
351  CCCAACGACC CCCGCCCATT GACGTCAATA ATGACGTATG TTCCCATAGT AACGCCAATA GGGACTTTCC
     GGGTTGCTGG GGGCGGGTAA CTGCAGTTAT TACTGCATAC AAGGGTATCA TTGCGGTTAT CCCTGAAAGG
421  ATTGACGTCA ATGGGTGGAC TATTTACGGT AAACTGCCCA CTTGGCAGTA CATCAAGTGT ATCATATGCC
     TAACTGCAGT TACCCACCTG ATAAATGCCA TTTGACGGGT GAACCGTCAT GTAGTTCACA TAGTATACGG
491  AAGTACGCCC CCTATTGACG TCAATGACGG TAAATGCCC GCCTGGCATT ATGCCCAGTA CATGACCTTA
     TTCATGCGGG GGATAACTGC AGTTACTGCC ATTTACCGGG CGGACCGTAA TACGGGTCAT GTACTGGAAT
                                                              NcoI
                                                            ~~~~~~~
561  TGGGACTTTC CTACTTGGCA GTACATCTAC TCGCTATTAC CATGGTGATG CGGTTTTGGC
     ACCCTGAAAG GATGAACCGT CATGTAGATG AGCGATAATG GTACCACTAC GCCAAAACCG
631  AGTACATCAA TGGGCGTGGA TAGCGGTTTG ACTCACGGGG ATTTCCAAGT CTCCACCCCA TTGACGTCAA
     TCATGTAGTT ACCCGCACCT ATCGCCAAAC TGAGTGCCCC TAAAGGTTCA GAGGTGGGGT AACTGCAGTT
701  TGGGAGTTTG TTTTGGCACC AAAATCAACG GGACTTTCCA AAATGTCGTA ACAACTCCGC CCCATTGACG
     ACCCTCAAAC AAAACCGTGG TTTTAGTTGC CCTGAAAGGT TTTACAGCAT TGTTGAGGCG GGGTAACTGC
771  CAAATGGGCG GTAGGCGTGT ACGGTGGGAG GTCTATATAA GCAGAGCTCT CTGGCTAACT AGAGAACCCA
     GTTTACCCGC CATCCGCACA TGCCACCCTC CAGATATATT CGTCTCGAGA GACCGATTGA TCTCTTGGGT
841  CTGCTTACTG GCTTATCGAA ATTAATACGA CTCACTATAG GGAGACCCAA GCTGGCTAGC GTTTAAACTT
     GACGAATGAC CGAATAGCTT TAATTATGCT GAGTGATATC CCTCTGGGTT CGACCGATCG CAAATTTGAA
                 EcoRI                                     NcoI
               ~~~~~~~                                    ~~~~~~~
                                                                M  A  P  K  K  R  R  K  V
```

```
 911  AAGCTGATCC ACTAGTCCAG TGTGGTGGAA TTCGCTAGCG CCACCATGGC CCCCAAGAAG AAGAGGAAGG
      TTCGACTAGG TGATCAGGTC ACACCACCTT AAGCGATCGC GGTGGTACCG GGGGTTCTTC TTCTCCTTCC
                                                 KpnI
                                                 ~~~~~
       .  G   I   D   G   V   P   F   Q   C   R   I   C   M   R   N   E   S   R   S   D   H   L   S  .
 981  TGGGAATCGA TGGGGTACCC TTCCAGTGTC GAATCTGCAT GCGTAACTTC AGTCGTAGTG ACCACCTGAG
      ACCCTTAGCT ACCCCATGGG AAGGTCACAG CTTAGACGTA CGCATTGAAG TCAGCATCAC TGGTGGACTC
       .  R   H   I   R   T   H   T   G   E   K   P   F   A   C   D   I   C   G   R   K   F   A   D  .
1051  CCGGCACATC CGCACCCACA CAGGCGAGAA GCCTTTTGCC TGTGACATTT GTGGGAGGAA ATTTGCCGAC
      GGCCGTGTAG GCGTGGGTGT GTCCGCTCTT CGGAAAACGG ACACTGTAAA CACCCTCCTT TAAACGGCTG
         N   R   D   R   T   K   H   T   K   I   H   T   G   G   Q   R   P   Y   A   C   P   V   E   S  .
1121  AACCGGGACC GCACAAAGCA TACCAAGATA CACACGGGCG GACAGCGGCC GTACGCATGC CCTGTCGAGT
      TTGGCCCTGG CGTGTTTCGT ATGGTTCTAT GTGTGCCCGC CTGTCGCCGG CATGCGTACG GGACAGCTCA
       .  C   D   R   R   F   S   D   R   K   T   L   I   E   H   I   R   I   H   T   G   Q   K   P  .
1191  CCTGCGATCG CCGCTTTTCT GACAGGAAGA CACTTATCGA GCATATCCGC ATCCACACCG GTCAGAAGCC
      GGACGCTAGC GGCGAAAAGA CTGTCCTTCT GTGAATAGCT CGTATAGGCG TAGGTGTGGC CAGTCTTCGG
       .  F   Q   C   R   I   C   M   R   N   F   S   T   S   S   G   L   S   R   H   I   R   T   H  .
1261  CTTCCAGTGT CGAATCTGCA TGCGTAACTT CAGTACCAGC AGCGGGCTGA GCCGCCACAT CCGCACCCAC
      GAAGGTCACA GCTTAGACGT ACGCATTGAA GTCATGGTCG TCGCCCGACT CGGCGGTGTA GGCGTGGGTG
         T   G   S   Q   K   P   F   Q   C   R   I   C   M   R   N   F   S   R   S   D   H   L   S   E  .
1331  ACAGGATCTC AGAAGCCCTT CCAGTGTCGA ATCTGCATGC GTAACTTCAG TCGTAGTGAC CACCTGAGCG
      TGTCCTAGAG TCTTCGGGAA GGTCACAGCT TAGACGTACG CATTGAAGTC AGCATCACTG GTGGACTCGC
       .  H   I   R   T   H   T   G   E   K   P   F   A   C   D   I   C   G   R   K   F   A   T   S  .
1401  AACACATTCG CACCCACACA GGCGAGAAGC CTTTTGCCTG TGACATTTGT GGGAGGAAAT TGCCACCAG
      TTGTGTAAGC GTGGGTGTGT CCGCTCTTCG GAAAACGGAC ACTGTAAACA CCCTCCTTTA AACGGTGGTC
       .  S   D   R   T   K   H   T   K   I   H   L   R   Q   K   D   A   A   R   G   S   G   M   D  .
1471  CAGGGACCGC ACAAAGCATA CCAAGATACA CCTGCGCCAA AAAGATGCGG CCCGGGGATC CGGCATGGAT
      GTCGACTGGCG TGTTTCGTAT GGTTCTATGT GGACGCGGTT TTTCTACGCC GGGCCCCTAG GCCGTACCTA
       .  A   K   S   L   T   A   W   S   R   T   L   V   T   F   K   D   V   F   V   D   F   T   R   E  .
1541  GCTAAGTCAC TAACTGCCTG GTCCCGGACA CTGGTGACCT TCAAGGATGT ATTTGTGGAC TTCACCAGGG
      CGATTCAGTG ATTGACGGAC CAGGGCCTGT GACCACTGGA AGTTCCTACA TAAACACCTG AAGTGGTCCC
```

FIG.9C

```
            .  E   W   K   L   L   D   T   A   Q   Q   I   V   Y   R   N   V   M   L   E   N   Y   K   N
1611   AGGAGTGGAA GCTGCTGGAC ACTGCTCAGC AGATCGTGTA CAGAAATGTG ATGCTGGAGA ACTATAAGAA
       TCCTCACCTT CGACGACCTG TGACGAGTCG TCTAGCACAT GTCTTTACAC TACGACCTCT TGATATTCTT
            .  L   V   S   L   G   Y   Q   L   T   K   P   D   V   I   L   R   L   E   K   G   E   E   P
1681   CCTGGTTCC TTGGGTTATC AGCTTACTAA GCCAGATGTG ATCCTCCGGT TGGAGAAGGG AGAAGAGCCC
       GGACCAAGG AACCCAATAG TCGAATGATT CGGTCTACAC TAGGAGGCCA ACCTCTTCCC TCTTCTCGGG
            .  W   L   V   E   R   E   I   H   Q   E   T   H   P   D   S   E   T   A   F   E   I   K   S   S
1751   TGGCTGGTGG AGAGAGAAAT TCACCAAGAG ACCCATCCTG ATTCAGAGAC TGCATTTGAA ATCAAATCAT
       ACCGACCACC TCTCTCTTTA AGTGGTTCTC TGGGTAGGAC TAAGTCTCTG ACGTAAACTT TAGTTTAGTA
                                                                 XhoI
                                                                ~~~~~~~~
            .  V   D   Y   K   D   D   D   D   K   *
1821   CAGTTGACTA CAAGGACGAC GATGACAAGT AAGCTTCTCG AGTCTAGCTA GAGGGCCCGT TTAAACCCGC
       GTCAACTGAT GTTCCTGCTG CTACTGTTCA TTCGAAGAGC TCAGATCGAT CTCCCGGGCA AATTTGGGCG
1891   TGATCAGCCT CGACTGTGCC TTCTAGTTGC CAGCCATCTG TTGTTTGCCC CTCCCCCGTG CCTTCCTTGA
       ACTAGTCGGA GCTGACACGG AAGATCAACG GTCGGTAGAC AACAAACGGG GAGGGGGCAC GGAAGGAACT
1961   CCCTGGAAGG TGCCACTCCC ACTGTCCTTT CCTAATAAAA TGAGGAAATT GCATCGCATT GTCTGAGTAG
       GGGACCTTCC ACGGTGAGGG TGACAGGAAA GGATTATTTT ACTCCTTTAA CGTAGCGTAA CAGACTCATC
2031   GTGTCATTCT ATTCTGGGGG GTGGGGTGGG GCAGGACAGC AAGGGGGAGG ATTGGGAAGA CAATAGCAGG
       CACAGTAAGA TAAGACCCCC CACCCCACCC CGTCCTGTCG TTCCCCCTCC TAACCCTTCT GTTATCGTCC
2101   CATGCTGGGG ATGCGGTGG TACGCCACCC CTCTATGGCT TCTGAGGCGG AAAGAACCAG CTGGGCTCT AGGGGTATC
       GTACGACCCC TACGCCACC GATGCGGTGGG GAGATACCGA AGACTCCGCC TTTCTTGGTC GACCCCGAGA TCCCCATAG
2171   CCCACGCGCC CTGTAGCGGC GCATTAAGCG CGGCGGGTGT CGGCGGGTGT CCACCAATGC GCGTCGCACT CCGCTACACT
       GGGTGCGCGG GACATCGCCG CGTAATTCGC GCCGCCCACA GCCGCCCACA GGTGGTTACG CGCAGCGTGA GGCGATGTGA
2241   TGCCAGCGCC CTAGCGCCCG CTCCTTTCGC GAGGAAAGCG AAAGAAGGGA AGGAAAGAGC CCACGTTCGC CGGCTTTCCC
       ACGGTCGCGG GATCGCGGGC GAGGAAAGCG CTCCTTTCGC TCCTTTCCCT AGGAAAGAGC AGGAAAGAGC GCCGAAAGGG
2311   CGTCAAGCTC TAAATCGGGG CATCCCTTTA GGGTTCCGAT TTAGTGCTTT ACGGCACCTC GACCCAAAA
       GCAGTTCGAG ATTTAGCCCC GTAGGGAAAT CCCAAGGCTA AATCACGAAA TGCCGTGGAG CTGGGGTTTT
2381   AACTTGATTA GGGTGATGGT TCACGTAGTG GCCATCGCCC CTGATAGACG GTTTTTCGCC CTTTGACGTT
       TTGAACTAAT CCCACTACCA AGTGCATCAC CGGTAGCGGG GACTATCTGC CAAAAAGCGG GAAACTGCAA
2451   GGAGTCCACG TTCTTTAATA GTGGACTCTT GTTCCAAACT GGAACAACAC TCAACCCTAT CTCGGTCTAT
```

FIG.9D

```
2521  CCTCAGGTGC AAGAAATTAT CACCTGAGAA CAAGGTTTGA CCTTGTTGTG AGTTGGGATA GAGCCAGATA
      TCTTTTGATT TATAAGGGAT TTTGGGGATT TCGGCCTATT GGTTAAAAAA TGAGCTGATT TAACAAAAAT
      AGAAAACTAA ATATTCCCTA AAACCCCTAA AGCCCGATAA CCAATTTTTT ACTCGACTAA ATTGTTTTTA
2591  TTAACGCGAA TTAATTCTGT GGAATGTGTG TCAGTTAGGG TGTGGAAAGT CCCCAGGCTC CCCAGGCAGG
      AATTGCGCTT AATTAAGACA CCTTACACAC AGTCAATCCC ACACCTTTCA GGGGTCCGAG GGGTCCGTCC
2661  CAGAAGTATG CAAAGCATGC ATCTCAATTA GTCAGCAACC AGTGTGGAA GTCCCCAGG CTCCCCAGCA
      GTCTTCATAC GTTTCGTACG TAGAGTTAAT CAGTCGTTGG TCCACACCTT TCAGGGGTCC GAGGGGTCGT
2731  GGCAGAAGTA TGCAAAGCAT GCATCTCAAT TAGTCAGCAA CCATAGTCCC GCCCTAACT CCGCCCATCC
      CCGTCTTCAT ACGTTTCGTA CGTAGAGTTA ATCAGTCGTT GGTATCAGGG CGGGGATTGA GGCGGGTAGG
                                                   NcoI
                                                   ~~~~~~~~
2801  CGCCCCTAAC TCCGCCCAGT CTCCGCCCAT TGGCTGACTA ATTTTTTTTA TTTATGCAGA
      GCGGGGATTG AGGCGGGTCA AGGCGGGTAA ACCGACTGAT TAAAAAAAT AAATACGTCT
2871  GGCCGAGGCC GCCTCTGCCT CTGAGCTATT CCAGAAGTAG TGAGGAGGCT TTTTGGAGG CCTAGCTTT
      CCGGCTCCGG CGGAGACGGA GACTCGATAA GGTCTTCATC ACTCCTCCGA AAAACCTCC GGATCCGAAA
2941  TGCAAAAAGC TCCCGGGAGC TTGTATATCC ATTTTCGGAT CTGATCAAGA GACAGGATGA GGATCGTTTC
      ACGTTTTTCG AGGGCCCTCG AACATATAGG TAAAAGCCTA GACTAGTTCT CTGTCCTACT CCTAGCAAAG
3011  GCATGATTGA ACAAGATGGA TTGCACGCAG GTTCTCCGGC CGCTTGGGTG GAGAGGCTAT TCGGCTATGA
      CGTACTAACT TGTTCTACCT AACGTGCGTC CAAGAGGCCG GCGAACCCAC CTCTCCGATA AGCCGATACT
3081  CTGGGCACAA CAGACAATCG GCTGCTCTGA TGCCGCCGTG TTCCGGCTGT CAGCGCAGGG GCGCCCGGTT
      GACCCGTGTT GTCTGTTAGC CGACGAGACT ACGGCGGCAC AAGGCCGACA GTCGCGTCCC CGCGGGCCAA
3151  CTTTTTGTCA AGACCGACCT GTCCGGTGCC CTGAATGAAC TGCAGGACGA ACGTCCTGCT CCGTCGCGCC CTATCGTGGC
      GAAAAACAGT TCTGGCTGGA CAGGCCACGG GACTTACTTG ACGTCCTGCT TGCAGGACGA GGCAGCGCGG GATAGCACCG
3221  TGGCCACGAC GGGCGTTCCT TGCGCAGCTG TGCTCGACGT TGTCACTGAA ACAGTGACTT CGCCCTTCCC ACTGGCTGCT
      ACCGGTGCTG CCCGCAAGGA ACGCGTCGAC ACGCGTCGAC ACAGTGACTT TGTCACTGAA GCGGGAAGGG TGACCGACGA
3291  ATTGGGCGAA GTGCCGGGGC AGGATCTCCT GTCATCTCAC CTTGCTCCTG CCGAGAAAGT ATCCATCATG
      TAACCCGCTT CACGGCCCCG TCCTAGAGGA CAGTAGAGTG GAACGAGGAC GGCTCTTTCA TAGGTAGTAC
3361  GCTGATGCAA TGCGGCGGCT GCATACGCTT GATCCGGCTA CCTGCCCATT CGACCACCAA GCGAAACATC
      CGACTACGTT ACGCCGCCGA CGTATGCGAA CTAGGCCGAT GGACGGGTAA GCTGGTGGTT CGCTTTGTAG
3431  GCATCGAGCG AGCACGTACT CGGATGGAAG CCGGTCTTGT CGATCAGGAT GATCTGGACG AAGAGCATCA
      CGTAGCTCGC TCGTGCATGA GCCTACCTTC GGCCAGAACA GCTAGTCCTA CTAGACCTGC TTCTCGTAGT
```

FIG.9E

```
3501  GGGGCTCGCG CCAGCCGAAC TGTTCGCCAG GCTCAAGGCG CGCATGCCCG ACGGGCGAGGA TCTCGTCGTG
      CCCGAGCGC GGTCGGCTTG ACAAGCGGTC CGAGTTCCGC GCGTACGGGC TGCCGCTCCT AGAGCAGCAC
          NcoI
          ~~~~~~
3571  ACCCATGGCG ATGCCTGCTT GCCGAATATC ATGGTGGAAA ATGGCCGCTT TTCTGGATTC ATCGACTGTG
      TGGGTACCGC TACGGACGAA CGGCTTATAG TACCACCTTT TACCGGCGAA AAGACCTAAG TAGCTGACAC
3641  GCCCGGCTGGG TGTGGCGGAC CGCTATCAGG ACATAGCGTT GGCTACCCGT GATATTGCTG AAGAGCTTGG
      CGGGCCGACCC ACACCGCCTG GCGATAGTCC TGTATCGCAA CCGATGGGCA CTATAACGAC TTCTCGAACC
3711  CGGGGAATGG GCTGACCGCT TCCTCGTGCT TTACGGTATC GCCGCTCCCG ATTCGCAGCG CATCGCCTTC
      GCCGCTTACC CGACTGGCGA AGGAGCACGA AATGCCATAG CGGCGAGGGC TAAGCGTCGC GTAGCGGAAG
3781  TATCGCCTTC TTGACGAGTT CTTCTGAGCG GGACTCTGGG GTTCGAAATG CCGACCAAG CGACGCCCAA
      ATAGCGGAAG AACTGCTCAA GAAGACTCGC CCTGAGACCC CAAGCTTTAC TGGCTGGTTC GCTGCGGGTT
3851  CCTGCCATCA CGAGATTTCG ATTCCACCGC GCGGAAGATA CTTTCCAACC CGAAGCCTTA CGTTTTCCGG
      GGACGGTAGT GCTCTAAAGC TAAGGTGGCG CGCCTTCTAT GAAAGGTTGG GCTTCGGAAT GCAAAAGGCC
3921  GACGCCGGCT GGATGATCCT CCAGCGCGGG GATCTCATGC TGGAGTTCTT CGCCCACCCC AACTTGTTTA
      CTGCGGCCGA CCTACTAGGA GGTCGCGCCC CTAGAGTACG ACCTCAAGAA GCGGGTGGGG TTGAACAAAT
3991  TTGCAGCTTA AATAAAAGCA TTTATTTCGT TATCGTAGTG TTTAAAGTGT TTATTTCGTA AAAAAAGTGA
      AACGTCGAAT ATTACCAATG TTTATTTGT CCAAACTCAT CAATGTATCT TATCATGTCT GTATACCGTC GACCTCTAGC
4061  GCATTCTAGT TGTGGTTTGT CCAAACTCAT CAATGTATCT TATCATGTCT GTATACCGTC GACCTCTAGC
      CGTAAGATCA ACACCAAACA GGTTTGAGTA GTTACATAGA ATAGTACAGA CATATGGCAG CTGGAGATCG
4131  TAGAGCTTGG CGTAATCATG GTCATAGCTG TTTCCTGTGT GAAATTGTTA TCCGCTCACA ATTCCACACA
      ATCTCGAACC GCATTAGTAC CAGTATCGAC AAAGGACACA CTTTAACAAT AGGCGAGTGT TAAGGTGTGT
4201  ACATACGAGC CGGAAGCATA AAGTGTAAAG CCTGGGGTGC CTAATGAGTG AGCTAACTCA CATTAATTGC
      TGTATGCTCG GCCTTCGTAT TTCACATTTC GGACCCCACG GATTACTCAC TCGATTGAGT GTAATTAACG
4271  GTTGCGCTCA CTGCCCGCTT TCCAGTCGGG AAACCTGTCG TGCCAGCTGC ATTAATGAAT CGGCCAACGC
      CAACGCGAGT GACGGGCGAA AGGTCAGCCC TTTGGACAGC ACGGTCGACG TAATTACTTA GCCGGTTGCG
4341  GCGGGGAGAG GCGGTTTGCG TATTGGGCGC TCTTCCGCTT CCTCGCTCAC TGACTCGCTG CGCTCGGTCG
      CGCCCCTCTC CGCCAAACGC ATAACCCGCG AGAAGGCGAA GGAGCGAGTG ACTGAGCGAC GCGAGCCAGC
4411  TTCGGCTGCG GCGAGCGGTA TCAGCTCACT CAAAGGCGGT AATACGGTTA TCCACAGAAT CAGGGGATAA
      AAGCCGACGC CGCTCGCCAT AGTCGAGTGA GTTTCCGCCA TTATGCCAAT AGGTGTCTTA GTCCCCTATT
4481  CGCAGGAAAG AACATGTGAG CAAAAGGCCA GCAAAAGGCC AGGAACCGTA AAAAGGCCGC GTTGCTGGCG
```

FIG.9F

```
       GCGTCCTTTC TTGTACACTC GTTTTCCGGT CGTTTTCCGG TCCTTGGCAT TTTTCCGGCG CAACGACCGC
       TTTTTCCATA GGCTCCGCCC CCCTGACGAG CATCACAAAA ATCGACGCTC AAGTCAGAGG TGGCGAAACC
       AAAAAGGTAT CCGAGGCGGG GGGACTGCTC GTAGTGTTTT TAGCTGCGAG TTCAGTCTCC ACCGCTTTGG
 4551  CGACAGGACT ATAAAGATAC CAGGCGTTTC CCCCTGGAAG CTCCCTCGTG CGCTCTCCTG TTCCGACCCT
       GCTGTCCTGA TATTTCTATG GTCCGCAAAG GGGGACCTTC GAGGGAGCAC GCGAGAGGAC AAGGCTGGGA
 4621  GCCGCTTACC GGATACCTGT CCGCCTTTCT CCCTTCGGGA AGCGTGGCGC TTTCTCAATG CTCACGCTGT
       CGGCGAATGG CCTATGGACA GCGGAAAGA GGGAAGCCCT TCGCACCGCG AAAGAGTTAC GAGTGCGACA
 4691  AGGTATCTCA GTTCGGTGTA GGTCGTTCGC TCCAAGCTGG GCTGTGTGCA CGAACCCCCC GTTCAGCCCG
       TCCATAGAGT CAAGCCACAT CCAGCAAGCG AGGTTCGACC CGACACACGT GCTTGGGGGG CAAGTCGGGC
 4761  ACCGCTGCGC CTTATCCCGT AACTATCGTC TTGAGTCCAA CCCGGTAAGA CACGACTTAT CGCCACTGGC
       TGGCGACGCG GAATAGGCCA TTGATAGCAG AACTCAGGTT GGGCCATTCT GTGCTGAATA GCGGTGACCG
 4831  AGCAGCCACT GGTAACAGGA TTAGCAGAGC GAGTATGTA GGCGGTGCTA CAGAGTTCTT GAAGTGGTGG
       TCGTCGGTGA CCATTGTCCT AATCGTCTCG CTCCATACAT CCGCCACGAT GTCTCAAGAA CTTCACCACC
 4901  CCTAACTACG GCTACACTAG AAGGACAGTA TTTGGTATCT GCGCTCTGCT GAAGCCAGTT ACCTTCGGAA
       GGATTGATGC CGATGTGATC TTCCTGTCAT AAACCATAGA CGCGAGACGA CTTCGGTCAA TGGAAGCCTT
 4971  AAAGAGTTGG TAGCTCTTGA TCCGGCAAAC AAAACCACGC TGGTAGCCGT GGTTTTTTG TTTGCAAGCA
       TTTCTCAACC ATCGAGAACT AGGCCGTTTG TTTGGTGGCG ACCATCGCCA CCAAAAAAC AAACGTTCGT
 5041  GCAGATTACG CGCAGAAAAA AAGGATCTCA AGAAGATCCT TTGATCTTTT CTACGGGGTC TGACGCTCAG
       CGTCTAATGC GGCGTCTTTT TTCCTAGAGT TCTTCTAGGA AACTAGAAAA GATGCCCCAG ACTGCGAGTC
 5111  TGGAACGAAA ACTCACGTTA AGGGATTTTG GTCATGAGAT TATCAAAAAG GATCTTCACC TAGATCCTTT
       ACCTTGCTTT TGAGTGCAAT TCCCTAAAAC CAGTACTCTA ATAGTTTTTC CTAGAAGTGG ATCTAGGAAA
 5181  TAAATTAAAA ATGAAGTTTT AAATCAATCT AAAGTATATA TGAGTAAACT TGGTCTGACA GTTACCAATG
       ATTTAATTTT TACTTCAAAA TTTAGTTAGA TTTCATATAT ACTCATTTGA ACCAGACTGT CAATGTTAC
 5251  CTTAATCAGT GAGGCACCTA TCTCAGCGAT CTGTCTATTT CGTTCATCCA TAGTTGCCTG ACTCCCCGTC
       GAATTAGTCA CTCCGTGGAT AGAGTCGCTA GACAGATAAA GCAAGTAGGT ATCAACGGAC TGAGGGGCAG
 5321  GTGTAGATAA CTACGATACG GGAGGGCTTA CCATCTGGCC CCAAGTGCTG AATGATACCG CGAGACCCAC
       CACATCTATT GATGCTATGC CCTCCCGAAT GGTAGACCGG GGTCACGACG TTACTATGGC GCTCTGGGTG
 5391  GCTCACCGGC TCCAGATTTA TCAGCAATAA ACCAGCCAGC CGGAAGGGCC GGGACGCAGAA GTGGTCCTGC
       CGAGTGGCCG AGGTCTAAAT AGTCGTTATT TGGTCGGTCG GCCTTCCCGG CTCGCGTCTT CACCAGGACG
 5461  AACTTTATCC GCCTCCATCC AGTCTATTAA TTGTTGCCGG GAAGCTAGAG TAAGTAGTTC GCCAGTAAT
       TTGAAATAGG CGGAGGTAGG TCAGATAATC AACAACGGCC CTTCGATCTC ATTCATCAAG CGGTCAATTA
 5531
```

FIG.9G

```
5601 AGTTTGCGCA ACGTTGTTGC CATTGCTACA GGCATCGTGG TGTCACGCTC GTCGTTTGGT ATGGCTTCAT
     TCAAACGCGT TGCAACAACG GTAACGATGT CCGTAGCACC ACAGTGCGAG CAGCAAACCA TACCGAAGTA
5671 TCAGCTCCGG TTCCCAACGA TCAAGGCGAG TTACATGATC CCCCATGTTG GGGTACAAC ACGTTTTTC GCCAATCGAG
     AGTCGAGGCC AAGGGTTGCT AGTTCCGCTC AATGTACTAG GGGTACAAC ACGTTTTTC GCCAATCGAG
5741 CTTCGGTCCT CCGATCGTTG TCAGAAGTAA GTTGGCCGCA GTGTTATCAC TCATGGTTAT GGCAGCACTG
     GAAGCCAGGA GGCTAGCAAC AGTCTTCATT CAACCGGCGT CACAATAGTG AGTACCAATA CCGTCGTGAC
5811 CATAATTCTC TTACTGTCAT GCCATCCGTA AGATGCTTTT CTGTGACTGG TGAGTACTCA ACCAAGTCAT
     GTATTAAGAG AATGACAGTA CGGTAGGCAT TCTACGAAAA GACACTGACC ACTCATGAGT TGGTTCAGTA
5881 TCTGAGAATA GTGTATGCGG CGACCGAGTT GCTCTTGCCC GGCGTCAATA CGGGATAATA CCCGCCACA
     AGACTCTTAT CACATACGCC GCTGGCTCAA CGAGAACGGG CCGCAGTTAT GCCCTATTAT GGCGCGGTGT
5951 TAGCAGAACT TTAAAAGTGC TCATCATTGG AAAAACGTTCT TCGGGGCGAA AACTCTCAAG GATCTTACCG
     ATCGTCTTGA AATTTTCACG AGTAGTAACC TTTTGCAAGA AGCCCCGCTT TTGAGAGTTC CTAGAATGGC
6021 CTGTTGAGAT CCAGTTCGAT GTAACCCCACT CGTGCACCCA ACTGATCTTT AGCATCTTTT ACTTTCACCA
     GACAACTCTA GGTCAAGCTA CATTGGGTGA GCACGTGGGT TGACTAGAAG TCGTAGAAAA TGAAAGTGGT
6091 GCGTTTCTGG GTGAGCAAAA ACAGGAAGGC AAAATGCCGC AAAAAAGGGA ATAAGGGCGA CACGGAAATG
     CGCAAAGACC CACTCGTTTT TGTCCTTCCG TTTTACGGCG TTTTTTCCCT TATTCCCGCT GTGCCTTTAC
6161 TTGAATACTC ATACTCTTCC TTTTTCAATA TATTGAAGC GTTATTGTCT CATGAGCGGA
     AACTTATGAG TATGAGAAGG AAAAAGTTAT AATAACTTCG CAATAGTCC CAATAACAGA GTACTCGCCT
6231 TACATATTTG AATGTATTTA GAAAAATAAA CAAATAGGGG TTCCGCGCAC ATTTCCCCGA AAAGTGCCAC
     ATGTATAAAC TTACATAAAT CTTTTTATTT GTTTATCCCC AAGGCGCGTG TAAAGGGGCT TTTCACGGTG
6301 CTGACGTC
     GACTGCAG
```

```
                        SEQUENCE LISTING

<160> NUMBER OF SEQ ID NOS: 53

<210> SEQ ID NO 1
<211> LENGTH: 7
<212> TYPE: PRT
<213> ORGANISM: Artificial Sequence
<220> FEATURE:
<223> OTHER INFORMATION: Engineered portion of a zinc finger peptide
      designed to bind with target mammalian sequences

<400> SEQUENCE: 1

Arg Ser Asp His Leu Ser Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Engineered portion of a zinc finger peptide
      designed to bind with target mammalian sequences

<400> SEQUENCE: 2

Asp Asn Arg Asp Arg Thr Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Engineered portion of a zinc finger peptide
      designed to bind with target mammalian sequences

<400> SEQUENCE: 3

Asp Arg Lys Thr Leu Ile Glu
```

-continued

```
<210> SEQ ID NO 4
<211> LENGTH: 7
<212> TYPE: PRT
<213> ORGANISM: Artificial Sequence
<220> FEATURE:
<223> OTHER INFORMATION: Engineered portion of a zinc finger peptide
      designed to bind with target mammalian sequences

<400> SEQUENCE: 4

Thr Ser Ser Gly Leu Ser Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Engineered portion of a zinc finger peptide
      designed to bind with target mammalian sequences

<400> SEQUENCE: 5

Arg Ser Asp His Leu Ser Glu
1               5

<210> SEQ ID NO 6
<211> LENGTH: 7
<212> TYPE: PRT
<213> ORGANISM: Artificial Sequence
<220> FEATURE:
<223> OTHER INFORMATION: Engineered portion of a zinc finger peptide
      designed to bind with target mammalian sequences

<400> SEQUENCE: 6

Thr Ser Ser Asp Arg Thr Lys
1               5

<210> SEQ ID NO 7
<211> LENGTH: 4
<212> TYPE: PRT
<213> ORGANISM: Artificial Sequence
<220> FEATURE:
<223> OTHER INFORMATION: Engineered portion of a zinc finger peptide
      designed to bind with target mammalian sequences

<400> SEQUENCE: 7

Arg Asp His Arg
1

<210> SEQ ID NO 8
<211> LENGTH: 4
<212> TYPE: PRT
<213> ORGANISM: Artificial Sequence
<220> FEATURE:
<223> OTHER INFORMATION: Engineered portion of a zinc finger peptide
      designed to bind with target mammalian sequences

<400> SEQUENCE: 8

Asp Arg Asp Lys
1

<210> SEQ ID NO 9
<211> LENGTH: 4
<212> TYPE: PRT
<213> ORGANISM: Artificial Sequence
<220> FEATURE:
<223> OTHER INFORMATION: Engineered portion of a zinc finger peptide
``` designed to bind with target mammalian sequences

<400> SEQUENCE: 9

Asp Lys Thr Glu
1

<210> SEQ ID NO 10
<211> LENGTH: 4
<212> TYPE: PRT
<213> ORGANISM: Artificial Sequence
<220> FEATURE:
<223> OTHER INFORMATION: Engineered portion of a zinc finger peptide
      designed to bind with target mammalian sequences

<400> SEQUENCE: 10

Thr Ser Gly Arg
1

<210> SEQ ID NO 11
<211> LENGTH: 4
<212> TYPE: PRT
<213> ORGANISM: Artificial Sequence
<220> FEATURE:
<223> OTHER INFORMATION: Engineered portion of a zinc finger peptide
      designed to bind with target mammalian sequences

<400> SEQUENCE: 11

Arg Asp His Glu
1

<210> SEQ ID NO 12
<211> LENGTH: 4
<212> TYPE: PRT
<213> ORGANISM: Artificial Sequence
<220> FEATURE:
<223> OTHER INFORMATION: Engineered portion of a zinc finger peptide
      designed to bind with target mammalian sequences

<400> SEQUENCE: 12

Thr Ser Asp Lys
1

<210> SEQ ID NO 13
<211> LENGTH: 5
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 13

Thr Gly Glu Lys Pro
1               5

<210> SEQ ID NO 14
<211> LENGTH: 6
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 14

Thr Gly Gly Gln Arg Pro
1               5

<210> SEQ ID NO 15

```
<211> LENGTH: 5
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 15

Thr Gly Gln Lys Pro
1               5

<210> SEQ ID NO 16
<211> LENGTH: 6
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 16

Thr Gly Ser Gln Lys Pro
1               5

<210> SEQ ID NO 17
<211> LENGTH: 18
<212> TYPE: DNA
<213> ORGANISM: Homo sapiens

<400> SEQUENCE: 17
acccgggttc ccctcggg                                                       18

<210> SEQ ID NO 18
<211> LENGTH: 25
<212> TYPE: PRT
<213> ORGANISM: Homo sapiens
<220> FEATURE:
<221> NAME/KEY: misc_feature
<222> LOCATION: (2)..(5)
<223> OTHER INFORMATION: Xaa can be any naturally occurring amino acid
      and up to 2 residues may be absent
<220> FEATURE:
<221> NAME/KEY: misc_feature
<222> LOCATION: (7)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
      and up to 2 residues may be absent

<400> SEQUENCE: 18

Cys Xaa Xaa Xaa Xaa Cys Xaa Xaa Xaa Xaa Xaa Xaa Xaa Xaa Xaa Xaa
1               5                   10                  15

Xaa Xaa His Xaa Xaa Xaa Xaa Xaa His
            20                  25

<210> SEQ ID NO 19
<211> LENGTH: 5
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 19

Thr Gly Glu Lys Pro
1               5
```

```
<210> SEQ ID NO 20
<211> LENGTH: 9
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 20

Leu Arg Gln Lys Asp Gly Glu Arg Pro
1               5

<210> SEQ ID NO 21
<211> LENGTH: 4
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 21

Gly Gly Arg Arg
1

<210> SEQ ID NO 22
<211> LENGTH: 5
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 22

Gly Gly Gly Gly Ser
1               5

<210> SEQ ID NO 23
<211> LENGTH: 8
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 23

Gly Gly Arg Arg Gly Gly Gly Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 24

Leu Arg Gln Arg Asp Gly Glu Arg Pro
1               5

<210> SEQ ID NO 25
<211> LENGTH: 12
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 25
```

Leu Arg Gln Lys Asp Gly Gly Gly Ser Glu Arg Pro
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Engineered linker sequence of a zinc finger
      peptide designed to bind with target mammalian sequences

<400> SEQUENCE: 26

Leu Arg Gln Lys Asp Gly Gly Gly Ser Gly Gly Gly Ser Glu Arg Pro
1               5                   10                  15

<210> SEQ ID NO 27
<211> LENGTH: 181
<212> TYPE: PRT
<213> ORGANISM: Artificial Sequence
<220> FEATURE:
<223> OTHER INFORMATION: Zinc finger protein designed to bind to a
      target sequence in the human CHK2 gene

<400> SEQUENCE: 27

Met Ala Glu Arg Pro Phe Gln Cys Arg Ile Cys Met Arg Asn Phe Ser
1               5                   10                  15

Arg Ser Asp His Leu Ser Arg His Ile Arg Thr His Thr Gly Glu Lys
                20                  25                  30

Pro Phe Ala Cys Asp Ile Cys Gly Arg Lys Phe Ala Asp Asn Arg Asp
            35                  40                  45

Arg Thr Lys His Thr Lys Ile His Thr Gly Gln Arg Pro Tyr Ala
        50                  55                  60

Cys Pro Val Glu Ser Cys Asp Arg Arg Phe Ser Asp Arg Lys Thr Leu
65                  70                  75                  80

Ile Glu His Ile Arg Ile His Thr Gly Gln Lys Pro Phe Gln Cys Arg
                85                  90                  95

Ile Cys Met Arg Asn Phe Ser Thr Ser Ser Gly Leu Ser Arg His Ile
            100                 105                 110

Arg Thr His Thr Gly Ser Gln Lys Pro Phe Gln Cys Arg Ile Cys Met
        115                 120                 125

Arg Asn Phe Ser Arg Ser Asp His Leu Ser Glu His Ile Arg Thr His
130                 135                 140

Thr Gly Glu Lys Pro Phe Ala Cys Asp Ile Cys Gly Arg Lys Phe Ala
145                 150                 155                 160

Thr Ser Ser Asp Arg Thr Lys His Thr Lys Ile His Leu Arg Gln Lys
                165                 170                 175

Asp Ala Ala Arg Asn
            180

<210> SEQ ID NO 28
<211> LENGTH: 6308
<212> TYPE: DNA
<213> ORGANISM: Homo sapiens
<220> FEATURE:
<221> NAME/KEY: misc_feature
<222> LOCATION: (1)..(6308)
<223> OTHER INFORMATION: Double stranded DNA sequence
<220> FEATURE:
<221> NAME/KEY: CDS
<222> LOCATION: (956)..(1849)

<400> SEQUENCE: 28

-continued

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc agatatacg cgttgacatt      240 gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgc cccattgacg caaatgggcg      780
gtaggcgtgt acggtgggag gtctatataa gcagagctct ctggctaact agagaaccca     840
ctgcttactg gcttatcgaa attaatacga ctcactatag ggagacccaa gctggctagc     900 gtttaaacttaagctgatcc actagtccag tgtggtggaa ttcgctagcg ccacc atg      958
                                                                Met
                                                                  1 gcc ccc aag aag aag agg aag gtg gga atc gat ggg gta ccc ttc cag     1006
Ala Pro Lys Lys Lys Arg Lys Val Gly Ile Asp Gly Val Pro Phe Gln
         5                  10                  15 tgt cga atc tgc atg cgt aac ttc agt cgt agt gac cac ctg agc cgg     1054
Cys Arg Ile Cys Met Arg Asn Phe Ser Arg Ser Asp His Leu Ser Arg
         20                  25                  30 cac atc cgc acc cac aca ggc gag aag cct ttt gcc tgt gac att tgt     1102
His Ile Arg Thr His Thr Gly Glu Lys Pro Phe Ala Cys Asp Ile Cys
         35                  40                  45 ggg agg aaa ttt gcc gac aac cgg gac cgc aca aag cat acc aag ata     1150
Gly Arg Lys Phe Ala Asp Asn Arg Asp Arg Thr Lys His Thr Lys Ile
 50                  55                  60                  65 cac acg ggc gga cag cgg ccg tac gca tgc cct gtc gag tcc tgc gat     1198
His Thr Gly Gly Gln Arg Pro Tyr Ala Cys Pro Val Glu Ser Cys Asp
                 70                  75                  80 cgc cgc ttt tct gac agg aag aca ctt atc gag cat atc cgc atc cac     1246
Arg Arg Phe Ser Asp Arg Lys Thr Leu Ile Glu His Ile Arg Ile His
         85                  90                  95 acc ggt cag aag ccc ttc cag tgt cga atc tgc atg cgt aac ttc agt     1294
Thr Gly Gln Lys Pro Phe Gln Cys Arg Ile Cys Met Arg Asn Phe Ser
        100                 105                 110 acc agc agc ggg ctg agc cgc cac atc cgc acc cac aca gga tct cag     1342
Thr Ser Ser Gly Leu Ser Arg His Ile Arg Thr His Thr Gly Ser Gln
        115                 120                 125 aag ccc ttc cag tgt cga atc tgc atg cgt aac ttc agt cgt agt gac     1390
Lys Pro Phe Gln Cys Arg Ile Cys Met Arg Asn Phe Ser Arg Ser Asp
130                 135                 140                 145 cac ctg agc gaa cac att cgc acc cac aca ggc gag aag cct ttt gcc     1438
His Leu Ser Glu His Ile Arg Thr His Thr Gly Glu Lys Pro Phe Ala
                150                 155                 160 tgt gac att tgt ggg agg aaa ttt gcc acc agc agc gac cgc aca aag     1486
Cys Asp Ile Cys Gly Arg Lys Phe Ala Thr Ser Ser Asp Arg Thr Lys
        165                 170                 175
```

| | | |
|---|---|---|
| cat acc aag ata cac ctg cgc caa aaa gat gcg gcc cgg gga tcc ggc<br>His Thr Lys Ile His Leu Arg Gln Lys Asp Ala Ala Arg Gly Ser Gly<br>180                       185                      190 | | 1534 |
| atg gat gct aag tca cta act gcc tgg tcc cgg aca ctg gtg acc ttc<br>Met Asp Ala Lys Ser Leu Thr Ala Trp Ser Arg Thr Leu Val Thr Phe<br>195                       200                     205 | | 1582 |
| aag gat gta ttt gtg gac ttc acc agg gag gag tgg aag ctg ctg gac<br>Lys Asp Val Phe Val Asp Phe Thr Arg Glu Glu Trp Lys Leu Leu Asp<br>210                       215                      225 | | 1630 |
| act gct cag cag atc gtg tac aga aat gtg atg ctg gag aac tat aag<br>Thr Ala Gln Gln Ile Val Tyr Arg Asn Val Met Leu Glu Asn Tyr Lys<br>                    230                     235                   240 | | 1678 |
| aac ctg gtt tcc ttg ggt tat cag ctt act aag cca gat gtg atc ctc<br>Asn Leu Val Ser Leu Gly Tyr Gln Leu Thr Lys Pro Asp Val Ile Leu<br>245                       250                     255 | | 1726 |
| cgg ttg gag aag gga gaa gag ccc tgg ctg gtg gag aga gaa att cac<br>Arg Leu Glu Lys Gly Glu Glu Pro Trp Leu Val Glu Arg Glu Ile His<br>260                       265                     270 | | 1774 |
| caa gag acc cat cct gat tca gag act gca ttt gaa atc aaa tca tca<br>Gln Glu Thr His Pro Asp Ser Glu Thr Ala Phe Glu Ile Lys Ser Ser<br>275                       280                     285 | | 1822 |
| gtt gac tac aag gac gac gat gac aag taagcttctc gagtctagct<br>Val Asp Tyr Lys Asp Asp Asp Asp Lys<br>290                       295 | | 1869 |
| agagggcccg tttaaacccg ctgatcagcc tcgactgtgc cttctagttg ccagccatct | | 1929 |
| gttgtttgcc cctcccccgt gccttccttg accctggaag gtgccactcc cactgtcctt | | 1989 |
| tcctaataaa atgaggaaat tgcatcgcat tgtctgagta ggtgtcattc tattctgggg | | 2049 |
| ggtggggtgg ggcaggacag caaggggag gattgggaag acaatagcag gcatgctggg | | 2109 |
| gatgcggtgg gctctatggc ttctgaggcg gaaagaacca gctgggctc taggggtat | | 2169 |
| ccccacgcgc cctgtagcgg cgcattaagc gcggcgggtg tggtggttac gcgcagcgtg | | 2229 |
| accgctacac ttgccagcgc cctagcgccc gctcctttcg ctttcttccc ttcctttctc | | 2289 |
| gccacgttcg ccggctttcc ccgtcaagct ctaaatcggg gcatcccttt agggttccga | | 2349 |
| tttagtgctt tacggcacct cgaccccaaa aaacttgatt agggtgatgg ttcacgtagt | | 2409 |
| gggccatcgc cctgatagac ggtttttcgc cctttgacgt tggagtccac gttctttaat | | 2469 |
| agtggactct tgttccaaac tggaacaaca ctcaacccta tctcggtcta ttcttttgat | | 2529 |
| ttataaggga ttttggggat ttcggcctat tggttaaaaa atgagctgat ttaacaaaaa | | 2589 |
| tttaacgcga attaattctg tggaatgtgt gtcagttagg gtgtggaaag tccccaggct | | 2649 |
| ccccaggcag gcagaagtat gcaaagcatg catctcaatt agtcagcaac caggtgtgga | | 2709 |
| aagtccccag gctccccagc aggcagaagt atgcaaagca tgcatctcaa ttagtcagca | | 2769 |
| accatagtcc cgcccctaac tccgcccatc ccgcccctaa ctccgcccag ttccgcccat | | 2829 |
| tctccgcccc atggctgact aatttttttt atttatgcag aggccgaggc cgcctctgcc | | 2889 |
| tctgagctat tccagaagta gtgaggaggc ttttttggag gcctaggctt ttgcaaaaag | | 2949 |
| ctcccgggag cttgtatatc catttcgga tctgatcaag agacaggatg aggatcgttt | | 3009 |
| cgcatgattg aacaagatgg attgcacgca ggttctccgg ccgcttgggt ggagaggcta | | 3069 |
| ttcggctatg actgggcaca acagacaatc ggctgctctg atgccgccgt gttccggctg | | 3129 |
| tcagcgcagg ggcgcccggt tctttttgtc aagaccgacc tgtccggtgc cctgaatgaa | | 3189 |
| ctgcaggacg aggcagcgcg gctatcgtgg ctggccacga cgggcgttcc ttgcgcagct | | 3249 |
| gtgctcgacg ttgtcactga agcgggaagg gactggctgc tattgggcga agtgccgggg | | 3309 |

```
caggatctcc tgtcatctca ccttgctcct gccgagaaag tatccatcat ggctgatgca    3369
atgcggcggc tgcatacgct tgatccggct acctgcccat tcgaccacca agcgaaacat    3429
cgcatcgagc gagcacgtac tcggatggaa gccggtcttg tcgatcagga tgatctggac    3489
gaagagcatc aggggctcgc gccagccgaa ctgttcgcca ggctcaaggc gcgcatgccc    3549
gacggcgagg atctcgtcgt gacccatggc gatgcctgct tgccgaatat catggtggaa    3609
aatggccgct tttctggatt catcgactgt ggccggctgg gtgtggcgga ccgctatcag    3669
gacatagcgt tggctacccg tgatattgct gaagagcttg gcggcgaatg ggctgaccgc    3729
ttcctcgtgc tttacggtat cgccgctccc gattcgcagc gcatcgcctt ctatcgcctt    3789
cttgacgagt tcttctgagc gggactctgg ggttcgaaat gaccgaccaa gcgacgccca    3849
acctgccatc acgagatttc gattccaccg ccgccttcta tgaaaggttg gcttcggaa    3909
tcgttttccg ggacgccggc tggatgatcc tccagcgcgg ggatctcatg ctggagttct    3969
tcgcccaccc caacttgttt attgcagctt ataatggtta caaataaagc aatagcatca    4029
caaatttcac aaataaagca ttttttttcac tgcattctag ttgtggtttg tccaaactca    4089
tcaatgtatc ttatcatgtc tgtataccgt cgacctctag ctagagcttg gcgtaatcat    4149
ggtcatagct gtttcctgtg tgaaattgtt atccgctcac aattccacac aacatacgag    4209
ccggaagcat aaagtgtaaa gcctggggtg cctaatgagt gagctaactc acattaattg    4269
cgttgcgctc actgcccgct ttccagtcgg gaaacctgtc gtgccagctg cattaatgaa    4329
tcggccaacg cgcggggaga ggcggtttgc gtattgggcg ctcttccgct tcctcgctca    4389
ctgactcgct gcgctcggtc gttcggctgc ggcgagcggt atcagctcac tcaaaggcgg    4449
taatacggtt atccacagaa tcaggggata acgcaggaaa gaacatgtga gcaaaaggcc    4509
agcaaaaggc caggaaccgt aaaaaggccg cgttgctggc gtttttccat aggctccgcc    4569
ccccctgacga gcatcacaaa aatcgacgct caagtcagag gtggcgaaac ccgacaggac    4629
tataaagata ccaggcgttt ccccctggaa gctccctcgt gcgctctcct gttccgaccc    4689
tgccgcttac cggatacctg tccgcctttc tcccttcggg aagcgtggcg ctttctcaat    4749
gctcacgctg taggtatctc agttcggtgt aggtcgttcg ctccaagctg ggctgtgtgc    4809
acgaacccc cgttcagccc gaccgctgcg ccttatccgg taactatcgt cttgagtcca    4869
acccggtaag acacgactta tcgccactgg cagcagccac tggtaacagg attagcagag    4929
cgaggtatgt aggcggtgct acagagttct tgaagtggtg gcctaactac ggctacacta    4989
gaaggacagt atttggtatc tgcgctctgc tgaagccagt taccttcgga aaaagagttg    5049
gtagctcttg atccggcaaa caaaccaccg ctggtagcgg tggtttttttt gtttgcaagc    5109
agcagattac gcgcagaaaa aaaggatctc aagaagatcc tttgatcttt tctacggggt    5169
ctgacgctca gtggaacgaa aactcacgtt aagggatttt ggtcatgaga ttatcaaaaa    5229
ggatcttcac ctagatcctt ttaaattaaa aatgaagttt taaatcaatc taaagtatat    5289
atgagtaaac ttggtctgac agttaccaat gcttaatcag tgaggcacct atctcagcga    5349
tctgtctatt tcgttcatcc atagttgcct gactccccgt cgtgtagata actacgatac    5409
gggagggctt accatctggc cccagtgctg caatgatacc gcgagaccca cgctcaccgg    5469
ctccagattt atcagcaata aaccagccag ccggaagggc cgagcgcaga agtggtcctg    5529
caactttatc cgcctccatc cagtctatta attgttgccg ggaagctaga gtaagtagtt    5589
cgccagttaa tagtttgcgc aacgttgttg ccattgctac aggcatcgtg gtgtcacgct    5649
```

| | |
|---|---|
| cgtcgtttgg tatggcttca ttcagctccg gttcccaacg atcaaggcga gttacatgat | 5709 |
| cccccatgtt gtgcaaaaaa gcggttagct ccttcggtcc tccgatcgtt gtcagaagta | 5769 |
| agttggccgc agtgttatca ctcatggtta tggcagcact gcataattct cttactgtca | 5829 |
| tgccatccgt aagatgcttt tctgtgactg gtgagtactc aaccaagtca ttctgagaat | 5889 |
| agtgtatgcg gcgaccgagt tgctcttgcc cggcgtcaat acgggataat accgcgccac | 5949 |
| atagcagaac tttaaaagtg ctcatcattg gaaaacgttc ttcggggcga aaactctcaa | 6009 |
| ggatcttacc gctgttgaga tccagttcga tgtaacccac tcgtgcaccc aactgatctt | 6069 |
| cagcatcttt tactttcacc agcgtttctg ggtgagcaaa aacaggaagg caaaatgccg | 6129 |
| caaaaaaggg aataagggcg acacggaaat gttgaatact catactcttc ctttttcaat | 6189 |
| attattgaag catttatcag ggttattgtc tcatgagcgg atacatattt gaatgtattt | 6249 |
| agaaaaataa acaaataggg gttccgcgca catttccccg aaaagtgcca cctgacgtc | 6308 |

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 29
ccgaacatac agcaagaaac actt                                           24

<210> SEQ ID NO 30
<211> LENGTH: 23
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 30
tccattgcca ctgtgatctt cta                                            23

<210> SEQ ID NO 31
<211> LENGTH: 26
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 31
cggattttca gggaagtggg tcctaa                                         26

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 32
gctggagtgc agtgggtgat                                                20

<210> SEQ ID NO 33
<211> LENGTH: 23
<212> TYPE: DNA
<213> ORGANISM: Artificial Sequence

```
<220> FEATURE:
<223> OTHER INFORMATION: Synthetic oligonucleotide sequence for RNA
      analysis

<400> SEQUENCE: 33
tgactgtagg ccaagctaat tgg                                              23

<210> SEQ ID NO 34
<211> LENGTH: 24
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 34
ttggctcact gcaagctctg ccct                                             24

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 35
ccagcaaact ggtgctcaag                                                  20

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 36
agtccaatgt ccagcccatg a                                                21

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 37
caccaaggtg ccggaactga tcaga                                            25

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 38
agagacccat cctgattcag a                                                21

<210> SEQ ID NO 39
<211> LENGTH: 21
<212> TYPE: DNA
<213> ORGANISM: Artificial Sequence
<220> FEATURE:
```

<223> OTHER INFORMATION: Synthetic oligonucleotide sequence for RNA
      analysis

<400> SEQUENCE: 39
agctcggatc cttacagatc t                                             21

<210> SEQ ID NO 40
<211> LENGTH: 19
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 40
ctgcatttga aatcaaatc                                                19

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 41
ttccgataac gaacgagact ct                                            22

<210> SEQ ID NO 42
<211> LENGTH: 19
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 42
tggctgaacg ccacttgtc                                                19

<210> SEQ ID NO 43
<211> LENGTH: 23
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 43
taactagtta cgcgaccccc gag                                           23

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 44 cctttttgcag accacagtcc a                                            21

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide sequence for RNA analysis

<400> SEQUENCE: 45
gcagggatga tgttctggag a                                        21

<210> SEQ ID NO 46
<211> LENGTH: 23
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 46
cactgccacc cagaagactg tgg                                      23

<210> SEQ ID NO 47
<211> LENGTH: 23
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 47
agcaaagaga gcgtctaacc aga                                      23

<210> SEQ ID NO 48
<211> LENGTH: 18
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 48
cctcaatgcc tcctggga                                            18

<210> SEQ ID NO 49
<211> LENGTH: 30
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 49
cgggttctaa gttccgctct cccttctaaa                               30

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 50
acatcaagaa ggtggtgaag                                          20

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide sequence for RNA
      analysis

```
<400> SEQUENCE: 51
agcttgacaa agtggtcgtt g                                              21

<210> SEQ ID NO 52
<211> LENGTH: 23
<212> TYPE: DNA
<213> ORGANISM: Artificial Sequence
<220> FEATURE:
<223> OTHER INFORMATION: Synthetic oligonucleotide sequence for RNA
      analysis

<400> SEQUENCE: 52
cactgagcac caggtggtct cct                                            23

<210> SEQ ID NO 53
<211> LENGTH: 180
<212> TYPE: PRT
<213> ORGANISM: Artificial Sequence
<220> FEATURE:
<223> OTHER INFORMATION: Zinc finger protein designed to bind to a
      target sequence in the rat phospholamban gene

<400> SEQUENCE: 53

Met Ala Glu Arg Pro Tyr Ala Cys Pro Val Glu Ser Cys Asp Arg Arg
1               5                   10                  15

Phe Ser Thr Ser Ala Asp Leu Thr Glu His Ile Arg Ile His Thr Gly
            20                  25                  30

Gln Lys Pro Phe Gln Cys Arg Ile Cys Met Arg Asn Phe Ser Ala Ser
        35                  40                  45

Ala Asn Leu Ser Arg His Ile Arg Thr His Thr Gly Gly Glu Arg Pro
    50                  55                  60

Phe Gln Cys Arg Ile Cys Met Arg Asn Phe Ser Arg Ser Asp Ala Leu
65                  70                  75                  80

Ser Thr His Ile Arg Thr His Thr Gly Glu Lys Pro Phe Ala Cys Asp
                85                  90                  95

Ile Cys Gly Arg Lys Phe Ala Asp Arg Ser Thr Arg Thr Lys His Thr
            100                 105                 110

Lys Ile His Thr Gly Ser Gln Lys Pro Phe Gln Cys Arg Ile Cys Met
        115                 120                 125

Arg Asn Phe Ser Arg Ser Asp Val Leu Ser Ala His Ile Arg Thr His
    130                 135                 140

Thr Gly Glu Lys Pro Phe Ala Cys Asp Ile Cys Gly Lys Lys Phe Ala
145                 150                 155                 160

Asp Arg Ser Asn Arg Ile Lys His Thr Lys Ile His Leu Arg Gln Lys
                165                 170                 175

Asp Ala Ala Arg
            180
```

US 7,407,776 B2

ENGINEERED ZINC FINGER PROTEINS FOR REGULATION OF GENE EXPRESSION

CROSS-REFERENCE TO RELATED APPLICATIONS

This application is a 35 U.S.C. §371 filing of PCT/US 2004/030606, filed Sep. 17, 2004. PCT/US 2004/030606 claims the benefit of U.S. Provisional Applications 60/504,502, filed Sep. 19. 2003. The disclosures of all of the aforementioned applications are incorporated by reference in their entireties for all purposes.

STATEMENT OF RIGHTS TO INVENTIONS MADE UNDER FEDERALLY SPONSORED RESEARCH

Not applicable.

TECHNICAL FIELD

The present disclosure provides methods and compositions for regulating expression of a selected endogenous gene using an engineered zinc finger protein.

BACKGROUND

Defects in transcriptional regulation underlie numerous disease states, including cancer. See, e.g., Nebert (2002) *Toxicology* 181-182:131-41. A major goal of current strategies for correcting such defects is to achieve sufficient specificity of action. See, e.g., Reid et al. (2002) *Curr Opin Mol Ther* 4:130-137. Designed zinc-finger protein transcription factors (ZFP TFs) emulate natural transcriptional control mechanisms, and therefore provide an attractive tool for precisely regulating gene expression. See, e.g., U.S. Pat. Nos. 6,607,882 and 6,534,261; and Beerli et al. (2000) *Proc Natl Acad Sci USA* 97:1495-500; Zhang et al. (2000) *J Biol Chem* 275:33850-60; Snowden et al. (2002) *Curr Biol* 12:2159-66; Liu et al. (2001) *J Biol Chem* 276:11323-34; Reynolds et al. (2003) *Proc Natl Acad Sci USA* 100:1615-20; Bartsevich et al. (2000) *Mol Pharmacol* 58:1-10; Ren et al. (2002) *Genes Dev* 16: 27-32; Jamieson et al. (2003) *Nat Rev Drug Discov* 2:361-368). Accurate control of gene expression is important for understanding gene function (target validation) as well as for developing therapeutics to treat disease. See, e.g., Urnov & Rebar (2002) *Biochem Pharmacol* 64:919-23.

However, for many disease states, it may be that these proteins, or any other gene regulation technology, will have to be specific for a single gene within the genome—a challenging criterion to meet given the size and complexity of the human genome. Indeed, recent studies with siRNA (Doench et al. (2003) *Genes Dev* 17:438-42; Jackson et al. (2003) *Nat Biotechnol* 18:18) and antisense DNA/RNA (Cho et al. (2001) *Proc Natl Acad Sci USA* 98:9819-23) have fallen far short of obtaining single-gene specificity; illuminating the magnitude of the task of obtaining exogenous regulation of a single specific gene in a genome, e.g., the human genome.

SUMMARY

The present disclosure relates to compositions comprising engineered zinc finger proteins and methods of using these compositions to specifically regulate expression of a single gene, e.g., an endogenous cellular gene. In additional embodiments, an engineered zinc finger protein is expressed in a cell for the purpose of obtaining targeted regulation of a single gene in a genome, e.g., the human genome. An engineered protein can be expressed in a cell, e.g., by delivering the protein to the cell or by delivering a polynucleotide encoding the protein to a cell, wherein the polynucleotide (if DNA) is transcribed, and the transcript (or a RNA molecule delivered to the cell) is translated, to generate the fusion protein. Methods for polynucleotide and polypeptide delivery to cells are presented elsewhere in this disclosure.

In one aspect, disclosed herein is a polynucleotide comprising a sequence encoding an engineered zinc finger protein, the engineered zinc finger protein comprising 3 or more 2-finger zinc finger modules, wherein the 2-finger zinc finger modules are joined to each other by linkers of 6 or more amino acid residues, and further wherein the engineered zinc finger protein specifically binds to a target site in cellular chromatin such that expression of a single gene is regulated. In certain embodiments, the target site comprises 18 base pairs.

In certain embodiments, described herein is polynucleotide encoding an engineered polypeptide comprising a plurality of zinc fingers, wherein in proceeding from the N-terminus to the C-terminus of the polypeptide the zinc fingers are denoted F1 through F6, and further wherein the amino acid sequence corresponding to positions −1 through +6 with respect to the start of the alpha-helical portion of each zinc finger is as follows F1: RSDHLSR (SEQ ID NO:1), F2: DNRDRTK (SEQ ID NO:2), F3: DRKTLIE (SEQ ID NO:3), F4: TSSGLSR (SEQ ID NO:4), F5: RSDHLSE (SEQ ID NO:5) and F6: TSSDRTK (SEQ ID NO:6).

In another aspect, described herein is a polynucleotide encoding an engineered polypeptide comprising a plurality of zinc fingers, wherein in proceeding from the N-terminus to the C-terminus of the polypeptide the zinc fingers are denoted F1 through F6, and further wherein the amino acid sequence corresponding to positions −1, +2, +3 and +6 with respect to the start of the alpha-helical portion of each zinc finger is as follows: F1: RDHR (SEQ ID NO:7), F2: DRDK (SEQ ID NO:8), F3: DKTE, F4 (SEQ ID NO:9): TSGR (SEQ ID NO:10), F5: RDHE (SEQ ID NO:11) and F6: TSDK (SEQ ID NO:12). In certain embodiments, the engineered polypeptides further comprise one or more linker sequences between one or more of the zinc fingers modules and/or between one or more zinc finger proteins that may be linked to each other, for example, linkers of 5 or more amino acids in length (e.g., TGEKP (SEQ ID NO:13), TGGQRP (SEQ ID NO:14), TGQKP (SEQ ID NO:15), and/or TGSQKP (SEQ ID NO:16). In certain embodiments, the linkers between F2-F3 and F4-F5 are longer (e.g., six amino acids in length) than the linkers between F1-F2, F3-F4 and F5-E6 (e.g., linkers that are five amino acids in length).

In other aspects, any of the polypeptides encoded by the polynucleotides described herein preferably bind to a target sequence comprising 5'-ACCCGGGTTCCCCTCGGG-3' (SEQ ID NO:17). In one embodiment, the target sequence is in the human chk2 gene; in further embodiments, the human chk2 gene is in its normal chromosomal environment. In additional embodiments, the target sequence 5'-ACCCGGGTTCCCCTCGGG-3' (SEQ ID NO:17) is present on an extrachromosomal nucleic acid, and can be operatively linked to the chk2 gene or to any other gene or coding sequence.

Any of the polynucleotides described herein may further comprise a sequence encoding at least one functional domain (e.g., a transcriptional activation domain, a transcriptional repression domain, or a nuclease domain).

In yet another aspect, the disclosure provides for polypeptides encoded by any of the polynucleotides described herein.

In other aspects, a polypeptide (or polynucleotide encoding this polypeptide) that competes with any of the engineered polypeptides described herein for binding to a target sequence is provided.

In a still further aspect, described herein is a method for regulating expression of a gene in a cell, the method comprising administering any of the polynucleotides or polypeptides described herein to the cell under conditions such that the zinc finger protein binds to a target site in the cell, thereby modulating expression of the single gene. The modulation may be, e.g., activation or repression. The target sequence may be, for example, 5'-ACCCGGGTTCCCCTCGGG-3' (SEQ ID NO:17). In one embodiment, the target sequence is in a human chk2 gene. Furthermore, the target sequence can be chromosomal or extrachromosomal.

In a still further aspect, described herein is a method for regulating expression of a gene in a cell, the method comprising expressing a first polypeptide in the cell, wherein the first polypeptide binds to a target site comprising the sequence 5'-ACCCGGGTTCCCCTCGGG-3' (SEQ ID NO:17) or competes for binding with a protein that binds to a target site comprising 5'-ACCCGGGTTCCCCTCGGG-3' (SEQ ID NO:17).

In additional embodiments, methods for regulation of a gene, by binding of a protein to a target sequence comprising the sequence 5'-ACCCGGGTTCCCCTCGGG-3' (SEQ ID NO:17), operatively linked to the gene, are provided. The gene can be chromosomal or extrachromosomal and can be regulated either negatively (i.e., repressed) or positively (i.e., activated). The protein can be an engineered zinc finger protein (or can be encoded by a polynucleotide) and can further comprise a functional domain such as, for example, a transcriptional activation domain, a transcriptional repression domain, a nuclease domain or a nuclease half-domain.

Methods for functional gene knock-outs are also provided, wherein a target sequence comprising 5'-ACCCGGGTTCCCCTCGGG-3' (SEQ ID NO:17) is operatively linked to a gene in a cell, and a protein (e.g., an engineered ZFP) that binds to the target sequence is expressed in the cell. The protein can optionally comprise a transcriptional repression domain. The gene can be chromosomal or extrachromosomal.

These and other embodiments will be readily apparent to one of skill in the art upon reading the present disclosure.

BRIEF DESCRIPTION OF THE DRAWINGS

FIG. 1A is a schematic representation of the CHK2 promoter indicating the positions of restriction sites and probe used in the DNAseI hypermapping as well as the experimentally determined major start site of transcription (Trxn). FIG. 1B is a reproduction of a blot depicting DNAseI hypermapping of the CHK2 promoter. The XbaI and MscI digests serve as location markers while the numbers indicated on the left refer to the positions of the size markers run alongside. FIG. 1C is a reproduction of a blot showing EMSA of ZFP-5475 used to determine the apparent in vitro Kd for this DNA binding protein. Maltose Binding Protein purified ZFP protein was titrated using a 3-fold dilution series as indicated.

FIG. 2A is a graph depicting repression of CHK2 expression by ZFP-5475 in cultured cells. Black bars show mRNA levels upon administration of 250 ng of plasmid. Gray bars shown mRNA levels upon administration of 62.5 ng of plasmid and the white bars show mRNA levels upon administration of 15 ng of plasmid. HEK293 cells transfected with the plasmids indicated were assayed for CHK2 mRNA by quantitative RT-PCR (TaqMan) after 72 hrs. The CHK2 mRNA levels were normalized relative to an internal control of GAPDH mRNA, and are expressed as this ratio. Charts represent data from a minimum of two independent experiments, with means and standard deviations shown. Transfection efficiency was assessed in each independent experiment via the use of a GFP expression plasmid control, in all experiments an apparent efficiency of 80-90% GFP positive cells was observed. FIG. 2B is a graph depicting binding of ZFP-5475 to its intended target site within the CHK2 promoter in vivo. HEK293 cells transfected with the indicated plasmids were assayed for enrichment of the CHK2 promoter by ChIP with primers specific for the ZFP proximal region. Enrichment was quantified by RT-PCR Results are expressed as the fold-increase of the ratio to the GAPDH control relative to the results for non-transfected cells, the value of which is arbitrarily set to 1. The same samples were analyzed with primers specific for the p16 locus as a second internal control (open bars). No enrichment was observed with pre-immune serum.

FIG. 3A is a graph depicting inducible repression of CHK2 mRNA expression in isolated single cell-derived clones. ZFP TF transduced HEK293 T-REx clones were assayed for CHK2 mRNA by quantitative RT-PCR (TaqMan) after 48 hrs in the presence (black bars) or absence (grey bars) of 1 ng/ml doxycycline. mRNA assays were done as in FIG. 2 except that the CHK2 mRNA levels were normalized relative to an internal 18S rRNA control. "Pool" refers to the antibiotically selected ZFP TF transduced HEK293 T-REx cell population prior to single cell cloning. FIG. 3B are graphs depicting that CHK2 repression correlates with ZFP TF expression. An individual isolated single cell-derived clone was assayed for both CHK2 mRNA (left graph) and ZFP TF mRNA (right graph) over the range of DOX concentrations indicated and normalized as above. FIG. 3C is a reproduction of a blot showing that CHK2 protein is completely abolished by expression of the ZFP TF. Whole cell lysates obtained from the experiment described in FIG. 3B were assayed for the presence of CHK2 by immunoblot, and normalized to the signal from TFIIB. FIG. 3D are graphs depicting that ZFP TF repression of CHK2 is reversible. The experimental strategy is shown diagrammatically above the panel. Following 72 h of DOX treatment at 1 ng/ml, the DOX was removed and both CHK2 mRNA (left graph) and ZFP TF mRNA (right graph) assayed by RT PCR as described in FIG. 3B at the time points indicated.

FIG. 4A shows levels of CHK2 mRNA. FIG. 4B shows levels of BAX mRNA. FIG. 4C shows levels of MDM2 mRNA.

FIG. 5A shows constitutive expression of the ZFP TF in isolated single cell-derived clones of hTERT immortalized untransformed human fibroblasts results in repression of CHK2 at the protein level. Whole cell lysates from 5 different single-cell derived clones were assayed by immunoblot for CHK2 expression. As a loading control the blot was re-probed with an antibody recognizing actin. FIG. 5B depicts ZFP TF driven repression of CHK2 ablates the DNA damage dependent phosphorylation of p53 at Ser-20. Control cells (transduced with an insertless vector) and two ZFP TF single cell-derived clones shown above to repress CHK2 expression by western were challenged by irradiation with 10-Gy X-rays. Whole cell lysates were obtained at the indicated times and analyzed by immunoblot with the indicated antibodies. Actin was used as a loading control as above.

FIG. 6 shows the amino acid sequence of a zinc finger protein (SEQ ID NO: 27) designed to bind to a target sequence in the human CHK2 gene. Sequences of the recognition region (amino acids −1 through +6 with respect to the start of the alpha-helical portion of the zinc finger) of each of the six zinc fingers are underlined. Linker sequences (between zinc fingers) are in boldface. Note that the protein comprises three two-finger modules. Each of the modules is separated from an adjacent module by a six amino acid linker. With each module, the two zinc fingers are separated by a five amino acid linker.

FIG. 7 shows the amino acid sequence of an exemplary zinc finger protein (SEQ ID NO: 53) designed to bind to a target sequence in the rat phospholamban gene. Sequences of the recognition region (amino acids −1 through +6 with respect to the start of the alpha-helical portion of the zinc finger) of each of the six zinc fingers are underlined. Linker sequences (between zinc fingers) are in boldface. Note that the protein comprises three two-finger modules. Each of the modules is separated from an adjacent module by a six amino acid linker. With each module, the two zinc fingers are separated by a five amino acid linker.

FIG. 9, panels A to G, depict the polynucleotide sequence of pcDNA3-5475-KOX1 (SEQ ID NO:28). Selected restriction sites and the zinc finger protein encoded by the plasmid are also shown.

DETAILED DESCRIPTION

General Overview

Figure 1:
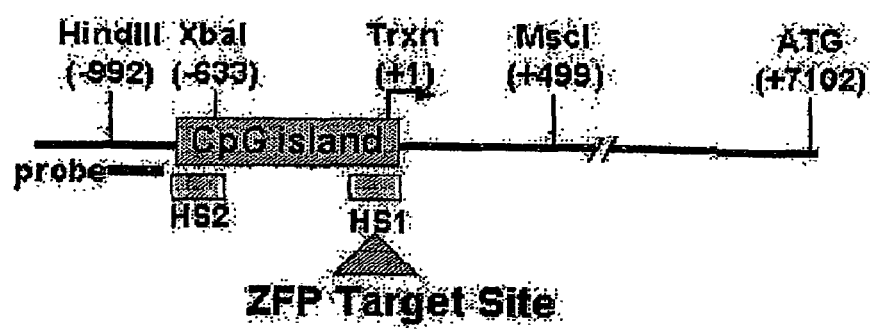
FIG. 1, panels A to C, depict initial steps in identification of a ZFP TF for the regulation of the human CHK2 gene.
Figure 1:
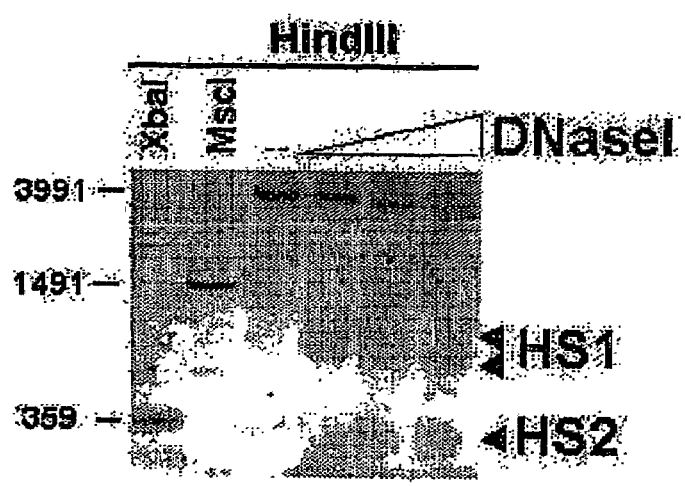
Figure 1:
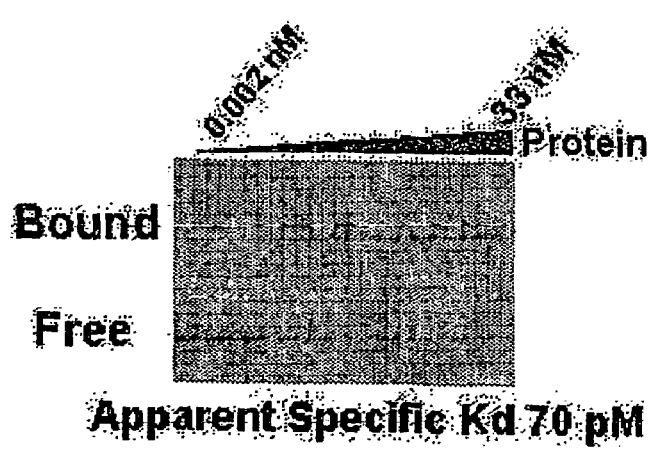

The present disclosure demonstrates that ZFPs can be used to regulate expression of a single gene within a genome. The gene can be an exogenous (e.g., extrachromosomal) gene or an endogenous cellular gene that is present in its native chromatin environment The present disclosure thus provides zinc finger DNA binding proteins that have been engineered to specifically recognize, with high efficacy, one particular endogenous cellular gene; thereby providing single gene specificity of gene regulation within a genome, e.g., a human genome.

Such methods of regulating expression of a single gene allow for novel human and mammalian therapeutic applications, e.g., treatment of genetic diseases, cancer, fungal, protozoal, bacterial, and viral infection, ischemia, vascular disease, arthritis, immunological disorders, etc., as well as providing means for functional genomics assays, and means for developing plants with altered phenotypes, including disease resistance, fruit ripening, sugar and oil composition, yield, and color.

As described herein and in co-owned U.S. Pat. Nos. 6,607,882; 6,534,261 and 6,453,242; ZFPs can be designed to recognize any suitable target site, for regulation of expression of any endogenous gene of choice. Examples of endogenous genes suitable for regulation include CHK2, VEGF, CCR5, ERα, Her2/Neu, Tat, Rev, HBV C, S, X, and P, LDL-R, PEPCK, CYP7, Fibrinogen, ApoB, Apo E, Apo(a), renin, NF-κB, I-κB, TNF-α, FAS ligand, amyloid precursor protein, atrial naturetic factor, ob-leptin, ucp-1, IL-1, IL-2, IL-3, IL-4, IL-5, IL-6, IL-12, G-CSF, GM-CSF, Epo, PDGF, PAF, p53, Rb, fetal hemoglobin, dystrophin, eutrophin, GDNF, NGF, IGF-1, VEGF receptors flt and flk, topoisomerase, telomerase, bcl-2, cyclins, angiostatin, IGF, ICAM-1, STATS, c-myc, c-myb, TH, PTI-1, polygalacturonase, EPSP synthase, FAD2-1, delta-12 desaturase, delta-9 desaturase, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, viral genes, protozoal genes, fungal genes, and bacterial genes. In general, suitable genes to be regulated include cytokines, lymphokines, growth factors, mitogenic factors, chemotactic factors, onco-active factors, receptors, potassium channels, G-proteins, signal transduction molecules, and other disease-related genes.

A general theme in transcription factor function is that simple binding and sufficient proximity to the promoter are all that is generally needed. Exact positioning relative to the promoter, orientation, and within limits, distance do not matter greatly. This feature allows considerable flexibility in choosing sites for constructing artificial transcription factors. The target site recognized by the ZFP therefore can be any suitable site in the target gene that will allow activation or repression of gene expression by a ZFP, optionally linked to a regulatory domain. Preferred target sites include regions adjacent to, downstream, or upstream of the transcription start site. In addition, target sites that are located in enhancer regions, repressor sites, RNA polymerase pause sites, and specific regulatory sites (e.g., SP-1 sites, hypoxia response elements, nuclear receptor recognition elements, p53 binding sites), sites in the cDNA encoding region or in an expressed sequence tag (EST) coding region. As described below, typically each finger recognizes 2-4 base pairs, with a two finger ZFP binding to a 4 to 7 bp target site, a three finger ZFP binding to a 6 to 10 base pair site, and a six finger ZFP binding to two adjacent target sites, each target site having from 6-10 base pairs.

As described herein, two ZFPs can be administered to a cell, recognizing either the same target endogenous cellular gene, or different target endogenous cellular gene. The first ZFP optionally is associated with the second ZFP, either covalently or non-covalently. Recognition of adjacent target sites by either associated or individual ZFPs can be used to produce cooperative binding of the ZFPs, resulting in an affinity that is greater than the affinity of the ZFPs when individually bound to their target site.

In one embodiment, two ZFPs are produced as a fusion protein linked by an amino acid linker, and the resulting six finger ZFP recognizes an approximately 18 base pair target site (see, e.g., Liu et al., *Proc Nat'l Acad Sci USA* 94:5525-5530 (1997)). An 18 base pair target site is expected to provide specificity in the human genome, as a target site of that size should occur only once in every $3 \times 10^{10}$ base pairs, and the size of the human genome is $3.5 \times 10^9$ base pairs (see, e.g., Liu et al., *PNAS* 94:5525-5530 (1997)). In another embodiment, the ZFPs are non-covalently associated, through a leucine zipper, a STAT protein N-terminal domain, or the FK506 binding protein (see, e.g., O'Shea, *Science* 254: 539 (1991), Barahmand-Pour et al., *Curr. Top. Microbiol. Immunol.* 211: 121-128 (1996); Klemm et al., *Annu. Rev. Immunol.* 16:569-592 (1998); Ho et al., *Nature* 382:822-826 (1996)).

In another embodiment, the ZFP is linked to at least one or more regulatory domains, described below. Preferred regulatory domains include transcription factor repressor or activator domains such as KRAB and VP16, co-repressor and co-activator domains, DNA methyl transferases, histone acetyltransferases, histone deacetylases, and endonucleases such as Fok1. For repression of gene expression, typically the expression of the gene is reduced by about 20% (i.e., 80% of non-ZFP modulated expression), more preferably by about 50% (i.e., 50% of non-ZFP modulated expression), more preferably by about 75-100% (i.e., 25% to 0% of non-ZFP modulated expression). For activation of gene expression, typically expression is activated by about 1.5 fold (i.e., 150% of non-ZFP modulated expression), preferably 2 fold (i.e., 200% of non-ZFP modulated expression), more preferably 5-10 fold (i.e., 500-1000% of non-ZFP modulated expression), up to at least 100 fold or more.

The expression of engineered ZFP activators and repressors can be also controlled by systems typified by the tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the ZFP activators and repressors and thus impart small molecule control on the target gene(s) of interest This beneficial feature could be used in cell culture models, in gene therapy, and in transgenic animals and plants.

The practice of conventional techniques in molecular biology, biochemistry, chromatin structure and analysis, computational chemistry, cell culture, recombinant DNA, bioinformatics, genomics and related fields are well-known to those of skill in the art and are discussed, for example, in the following literature references: Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999, all of which are incorporated by reference in their entireties.

Definitions

As used herein, the following terms have the meanings ascribed to them unless specified otherwise.

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T. The terms also encompasses nucleic acids containing modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Nucleic acids include, for example, genes, cDNAs, and mRNAs. Polynucleotide sequences are displayed herein in the conventional 5'-3' orientation.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins. The polypeptide sequences are displayed herein in the conventional N-terminal to C-terminal orientation.

A "binding protein" "or binding domain" is a protein or polypeptide that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger binding protein" is a protein or polypeptide that binds DNA, RNA and/or protein, preferably in a sequence-specific manner, as a result of stabilization of protein structure through coordination of a zinc ion. The term zinc finger binding protein is often abbreviated as zinc finger protein or ZFP. The individual DNA binding domains are typically referred to as "fingers" A ZFP has least one finger, typically two fingers, three fingers, or six fingers. Each finger binds from two to four base pairs of DNA, typically three or four base pairs of DNA. A ZFP binds to a nucleic acid sequence called a target site or target segment Each finger typically comprises an approximately 30 amino acid, zinc-chelating, DNA-binding subdomain. An exemplary motif characterizing one class of these proteins ($C_2H_2$ class) is -Cys-$(X)_{2-4}$-Cys-$(X)_{12}$-His-$(X)_{3-5}$-His (where X is any amino acid) (SEQ ID NO:18). Studies have demonstrated that a single zinc finger of this class consists of an alpha helix containing the two invariant histidine residues co-ordinated with zinc along with the two cysteine residues of a single beta turn (see, e.g., Berg & Shi, *Science* 271:1081-1085 (1996)).

Zinc finger binding domains can be engineered to bind to a predetermined nucleotide sequence. Non-limiting examples of methods for engineering zinc finger proteins are design and selection.

A "designed" zinc finger protein is a protein not occurring in nature whose structure and composition result principally from rational criteria. Rational criteria for design include application of substitution rules and computerized algorithms for processing information in a database storing information of existing ZFP designs and binding data, for example as described in co-owned U.S. Pat. No. 6,453,242. See also U.S. Pat. Nos. 6,140,081 and 6,534,261 and WO 98/53058; WO 98/53059; WO 98/53060; WO 02/016536 and WO 03/016496. A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

A "target site" or "target sequence" is a sequence that is bound by a binding protein such as, for example, a ZFP. Target sequences can be nucleotide sequences (either DNA or RNA) or amino acid sequences. A single target site typically has about four to about ten base pairs. Typically, a two-fingered ZFP recognizes a four to seven base pair target site, a three-fingered ZFP recognizes a six to ten base pair target site, and a six fingered ZFP recognizes two adjacent nine to ten base pair target sites. By way of example, a DNA target sequence for a three-finger ZFP is generally either 9 or 10 nucleotides in length, depending upon the presence and/or nature of cross-strand interactions between the ZFP and the target sequence. Target sequences can be found in any DNA or RNA sequence, including regulatory sequences, exons, introns, or any non-coding sequence.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (e.g., a "D-able subsite," as described for example co-owned U.S. Pat. No. 6,453,242, incorporated by reference in its entirety herein, a subsite is four nucleotides in length and overlaps with another 3- or 4-nucleotide subsite.

The term "adjacent target sites" refers to non-overlapping target sites that are separated by zero to about 5 base pairs.

The term "naturally-occurring" is used to describe an object that can be found in nature, as distinct from being artificially produced by a human.

"$K_d$" refers to the dissociation constant for the compound, i.e., the concentration of a compound (e.g., a zinc finger protein) that gives half maximal binding of the compound to its target (i.e., half of the compound molecules are bound to the target) under given conditions (i.e., when [target]<<$K_d$), as measured using a given assay system (see, e.g., U.S. Pat. No. 5,789,538). The assay system used to measure the $K_d$ should be chosen so that it gives the most accurate measure of the actual $K_d$ of the ZFP. Any assay system can be used, as long is it gives an accurate measurement of the actual $K_d$ of the ZFP. In one embodiment, the $K_d$ for a ZFP is measured using an electrophoretic mobility shift assay ("EMSA"), as described in Example 1 and elsewhere in the present specification. Unless an adjustment is made for ZFP purity or activity, the $K_d$ calculations made using the method of Example 1 may result in an underestimate of the true $K_d$ of a given ZFP. Preferably, the $K_d$ of a ZFP used to modulate transcription of an endogenous cellular gene is less than about 100 nM, more preferably less than about 75 nM, more preferably less than about 50 nM most preferably less than about 25 nM.

"Specific binding" between, for example, a ZFP and a specific target site means a binding affinity of at least $1 \times 10^6$ $M^{-1}$.

An "exogenous molecule" is a molecule that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule. Thus, the term "exogenous regulatory molecule" refers to a molecule that can modulate gene expression in a target cell but which is not encoded by the cellular genome of the target cell.

An exogenous molecule can be, among other things, a small molecule, such as is generated by a combinatorial chemistry process, or a macromolecule such as a protein, nucleic acid, carbohydrate, lipid, glycoprotein, lipoprotien, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., protein or nucleic acid (i.e., an exogenous gene), providing it has a sequence that is different from an endogenous molecule. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous molecule" is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and components of chromatin remodeling complexes.

Thus, an "endogenous cellular gene" refers to a gene that is native to a cell, which is in its normal genomic and chromatin context, and which is not heterologous to the cell. Such cellular genes include, e.g., animal genes, plant genes, bacterial genes, protozoal genes, fungal genes, mitochondrial genes, and chloroplastic genes.

An "endogenous gene" refers to a microbial or viral gene that is part of a naturally occurring microbial or viral genome in a microbially or virally infected cell. The microbial or viral genome can be extrachromosomal or integrated into the host chromosome. This term also encompasses endogenous cellular genes, as described above.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "native chromatin environment" refers to the naturally occurring, structural relationship of genomic DNA (e.g., bacterial, animal, fungal, plant, protozoal, mitochondrial, and chloroplastic) and DNA-binding proteins (e.g., histones, non-histone chromosomal proteins and bacterial DNA binding protein II), which together form chromosomes. The endogenous cellular gene can be in a transcriptionally active or inactive state in the native chromatin environment A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

The phrase "adjacent to a transcription initiation site" refers to a target site that is within about 50 bases either upstream or downstream of a transcription initiation site. "Upstream" of a transcription initiation site refers to a target site that is more than about 50 bases 5' of the transcription initiation site (i.e., in the non-transcribed region of the gene). "Downstream" of a transcription initiation site refers to a target site that is more than about 50 bases 3' of the transcription initiation site.

The phrase "RNA polymerase pause site" is described in Uptain et al., *Annu. Rev. Biochem.* 66:117-172 (1997).

"Humanized" refers to a non-human polypeptide sequence that has been modified to minimize immunoreactivity in humans, typically by altering the amino acid sequence to mimic existing human sequences, without substantially altering the function of the polypeptide sequence (see, e.g., Jones et al., *Nature* 321:522-525 (1986), and published UK patent application No. 8707252). Backbone sequences for the ZFPs are preferably be selected from existing human $C_2H_2$ ZFPs (e.g., SP-1). Functional domains are preferably selected from existing human genes, (e.g., the activation domain from the p65 subunit of NF-κB). Where possible, the recognition helix sequences will be selected from the thousands of existing ZFP DNA recognition domains provided by sequencing the human genome. As much as possible, domains will be combined as units from the same existing proteins. All of these steps will minimize the introduction of new junctional epitopes in the chimeric ZFPs and render the engineered ZFPs less immunogenic.

"Administering" an expression vector, nucleic acid, ZFP, or a delivery vehicle to a cell comprises transducing, transfecting, electroporating, translocating, fusing, phagocytosing, shooting or ballistic methods, etc., i.e., any means by which a protein or nucleic acid can be transported across a cell membrane and preferably into the nucleus of a cell.

The term "effective amount" includes that amount which results in the desired result, for example, deactivation of a previously activated gene, activation of a previously repressed gene, or inhibition of transcription of a structural gene or translation of RNA.

A "delivery vehicle" refers to a compound, e.g., a liposome, toxin, or a membrane translocation polypeptide, which is used to administer a ZFP. Delivery vehicles can also be used to administer nucleic acids encoding ZFPs, e.g., a lipid: nucleic acid complex, an expression vector, a virus, and the like.

A "gene," for the purposes of the present disclosure, includes a DNA region encoding a gene product (see below), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Further, a promoter can be a normal cellular promoter or, for example, a promoter of an infecting microorganism such as, for example, a bacterium or a virus. For example, the long terminal repeat (LTR) of retroviruses is a promoter region which may be a target for a modified zinc finger binding polypeptide. Promoters from members of the Lentivirus group, which include such pathogens as human T-cell lymphotrophic virus (HTLV) 1 and 2, or human immunodeficiency virus (HIV) 1 or 2, are examples of viral promoter regions which may be targeted for transcriptional modulation by a modified zinc finger binding polypeptide as described herein.

"Gene expression" refers to the conversion of the information, contained in a gene, into a gene product A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs that are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process which results in an increase in production of a gene product. A gene product can be either RNA (including, but not limited to, mRNA, rRNA, tRNA, and structural RNA) or protein. Accordingly, gene activation includes those processes that increase transcription of a gene and/or translation of a mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes that increase translation include those which increase translational initiation, those which increase translational elongation and those which increase mRNA stability. In general, gene activation comprises any detectable increase in the production of a gene product, preferably an increase in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more.

"Gene repression" and "inhibition of gene expression" refer to any process which results in a decrease in production of a gene product A gene product can be either RNA (including, but not limited to, mRNA, rRNA, tRNA, and structural RNA) or protein. Accordingly, gene repression includes those processes that decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes that decrease translation include those that decrease translational initiation, those that decrease translational elongation and those which decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more. Most preferably, gene repression results in complete inhibition of gene expression, such that no gene product is detectable.

The term "modulate" refers to a change in the quantity, degree or extent of a function. For example, the modified zinc finger-nucleotide binding polypeptides disclosed herein may modulate the activity of a promoter sequence by binding to a motif within the promoter, thereby inducing, enhancing or suppressing transcription of a gene operatively linked to the promoter sequence. Alternatively, modulation may include inhibition of transcription of a gene wherein the modified zinc finger-nucleotide binding polypeptide binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript Thus, "modulation" of gene expression includes both gene activation and gene repression.

Modulation can be assayed by determining any parameter that is indirectly or directly affected by the expression of the target gene. Such parameters include, e.g., changes in RNA or protein levels; changes in protein activity; changes in product levels; changes in downstream gene expression; changes in transcription or activity of reporter genes such as, for example, luciferase, CAT, beta-galactosidase, or GFP (see, e.g. Mistili & Spector, (1997) *Nature Biotechnology* 15:961-964); changes in signal transduction; changes in phosphorylation and dephosphorylation; changes in receptor-ligand interactions; changes in concentrations of second messengers such as, for example, cGMP, cAMP, IP$_3$, and Ca2$^+$; changes in cell growth, changes in neovascularization, and/or changes in any functional effect of gene expression. Measurements can be made in vitro, in vivo, and/or ex vivo. Such functional effects can be measured by conventional methods, e.g., measurement of RNA or protein levels, measurement of RNA stability, and/or identification of downstream or reporter gene expression. Readout can be by way of, for example, chemiluminescence, fluorescence, colorimetric reactions, antibody binding, inducible markers, ligand binding assays; changes in intracellular second messengers such as cGMP and inositol triphosphate (IP$_3$); changes in intracellular calcium levels; cytokine release, and the like.

Accordingly, the terms "modulating expression" "inhibiting expression" and "activating expression" of a gene can refer to the ability of a molecule to activate or inhibit transcription of a gene. Activation includes prevention of transcriptional inhibition (i.e., prevention of repression of gene expression) and inhibition includes prevention of transcriptional activation (i.e., prevention of gene activation).

To determine the level of gene expression modulation by a ZFP, cells contacted with ZFPs are compared to control cells, e.g., without the zinc finger protein or with a non-specific ZFP, to examine the extent of inhibition or activation. Control samples are assigned a relative gene expression activity value of 100%. Modulation/inhibition of gene expression is achieved when the gene expression activity value relative to the control about 80%, preferably 50% (i.e., 0.5× the activity of the control), more preferably 25%, more preferably 5-0%. Modulation/activation of gene expression is achieved when the gene expression activity value relative to the control is 110%, more preferably 150% (i.e., 1.5× the activity of the control), more preferably 200-500%, more preferably 1000-2000% or more.

A "promoter" is defined as an array of nucleic acid control sequences that direct transcription. As used herein, a promoter typically includes necessary nucleic acid sequences near the start site of transcription, such as, in the case of certain RNA polymerase II type promoters, a TATA element, enhancer, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Gal4, the lac repressor and the like.

A "constitutive" promoter is a promoter that is active under most environmental and developmental conditions. An "inducible" promoter is a promoter that is active under certain environmental or developmental conditions.

A "weak promoter" refers to a promoter having about the same activity as a wild type herpes simplex virus ("HSV")

thymidine kinase ("tk") promoter or a mutated HSV tk promoter, as described in Eisenberg & McKnight, *Mol. Cell. Biol.* 5:1940-1947 (1985).

A "transcriptional activator" and a "transcriptional repressor" refer to proteins or functional fragments of proteins that have the ability to modulate transcription, as described above. Such proteins include, e.g., transcription factors and co-factors (e.g., KRAB, MAD, ERD, SID, nuclear factor kappa B subunit p65, early growth response factor 1, and nuclear hormone receptors, VP16, VP64), endonucleases, integrases, recombinases, methyltransferases, histone acetyltransferases, histone deacetylases etc. Activators and repressors include co-activators and co-repressors (see, e.g. Utley et al., *Nature* 394:498-502 (1998)).

A "regulatory domain" or "functional domain" refers to a protein or a polypeptide sequence that performs a function related to DNA and/or RNA such as, for example, transcriptional modulation or DNA cleavage; or that is capable of interacting with proteins and/or protein domains that perform such a function. In certain embodiments, a transcriptional activation domain or a transcriptional repression domain is covalently or non-covalently linked to a DNA-binding domain (e.g., a ZFP) to modulate transcription of a gene of interest. Alternatively, a ZFP can act, in the absence of a functional domain, to modulate transcription. Furthermore, transcription of a gene of interest can be modulated by a ZFP linked to multiple functional domains. In additional embodiments, a cleavage domain or a cleavage half-domain is covalently or non-covalently linked to a DNA-binding domain for targeted cleavage of a nucleic acid sequence as disclosed, for example, in co-owned U.S. provisional patent application Ser. No. 60/493,931.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340: 245-246; U.S. Pat. No. 5,585,245 and PCT WO 98/44350.

A "fusion molecule" is a molecule in which two or more subunit molecules are linked, preferably covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a transcriptional activation domain) and fusion nucleic acids (for example, a nucleic acid encoding the fusion polypeptide described herein). Examples of the second type of fusion molecule include, but are not limited to, a fusion between a triplex-forming nucleic acid and a polypeptide, and a fusion between a minor groove binder and a nucleic acid.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include an non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell.

Similarly, a heterologous protein indicates that the protein comprises two or more subsequences that are not found in the same relationship to each other in nature (e.g., a "fusion protein," where the two subsequences are encoded by a single nucleic acid sequence). See, e.g., Ausubel, supra, for an introduction to recombinant techniques.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain.

With respect to fusion polypeptides, the terms "operatively linked" and "operably linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion polypeptide, the ZFP DNA-binding domain portion is able to bind its target site and/or its binding site, while the transcriptional activation domain (or functional fragment thereof) is able to activate transcription.

An "expression vector" is a nucleic acid construct, generated recombinantly or synthetically, with a series of specified nucleic acid elements that permit transcription of a particular nucleic acid in a host cell, and optionally integration or replication of the expression vector in a host cell. The expression vector can be part of a plasmid, virus, or nucleic acid fragment, of viral or non-viral origin. Typically, the expression vector includes an "expression cassette," which comprises a nucleic acid to be transcribed operably linked to a promoter. The term expression vector also encompasses naked DNA operably linked to a promoter.

By "host cell" is meant a cell that contains a ZFP or an expression vector or nucleic acid encoding a ZFP. The host cell typically supports the replication or expression of the expression vector. Host cells may be prokaryotic cells such as *E. coli*, or eukaryotic cells such as fungal cells (e.g., yeast), protozoal cells, plant cells, insect cells, animal cells, avian cells, teleost cells, amphibian cells, mammalian cells, primate cells or human cells. Exemplary mammalian cell lines include CHO, HeLa, 293, COS-1, and the like, e.g., cultured cells (in vitro), explants and primary cultures (in vitro and ex vivo), and cells in vivo.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine, and methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon in an amino acid herein, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid and nucleic acid sequences, individual substitutions, deletions or additions that alter, add or delete a single amino acid or nucleotide or a small percentage of amino acids or nucleotides in the sequence create a "conservatively modified variant," where the alteration results in the substitution of an amino acid with a chemically similar amino acid. Conservative substitution tables providing functionally similar amino acids are well known in the art. Such conservatively modified variants are in addition to and do not exclude polymorphic variants and alleles.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).
(see, e.g., Creighton, *Proteins* (1984) for a discussion of amino acid properties).

Design of ZFPs

The ZFPs disclosed herein are engineered to recognize a selected target site in the endogenous gene of choice. Typically, a backbone from any suitable $C_2H_2$ ZFP, such as SP-1, SP-1C, or ZIF268, is used as the scaffold for the engineered ZFP (see, e.g., Jacobs, *EMBO J.* 11:4507 (1992); Desjarlais & Berg, *PNAS* 90:2256-2260 (1993)). A number of methods can then be used to design and select a ZFP with high affinity for its target (e.g., preferably with a $K_d$ of less than about 25 nM). As described above, a ZFP can be designed or selected to bind to any suitable target site in the target endogenous gene, with high affinity. Co-owned U.S. Pat. No. 6,453,242, herein incorporated by reference in its entirety, comprehensively describes methods for design, construction, and expression of ZFPs for selected target sites.

Any suitable method known in the art can be used to design and construct nucleic acids encoding ZFPs, e.g., phage display, random mutagenesis, combinatorial libraries, computer/rational design, affinity selection, PCR, cloning from cDNA or genomic libraries, synthetic construction and the like. (see, e.g., U.S. Pat. No. 5,786,538; Wu et al., *PNAS* 92:344-348 (1995); Jamieson et al., *Biochemistry* 33:5689-5695 (1994); Rebar & Pabo, *Science* 263:671-673 (1994); Choo & Klug, *PNAS* 91:11163-11167 (1994); Choo & Klug, *PNAS* 91: 11168-11172 (1994); Desjarlais & Berg, *PNAS* 90:2256-2260 (1993); Desjarlais & Berg, *PNAS* 89:7345-7349 (1992); Pomerantz et al., *Science* 267:93-96 (1995); Pomerantz et al., *PNAS* 92:9752-9756 (1995); and Liu et al., *PNAS* 94:5525-5530 (1997); Griesman & Pabo, *Science* 275: 657-661 (1997); Desjarlais & Berg, *PNAS* 91:11-99-11103 (1994)).

In one embodiment, co-owned U.S. Pat. No. 6,453,242, incorporated by reference in its entirety herein, provides methods that select a target gene, and identify a target site within the gene containing one to six (or more) D-able sites (see definition below). Using these methods, a ZFP can then be synthesized that binds to the preselected site. These methods of target site selection are premised, in part, on the recognition that the presence of one or more D-able sites in a target segment confers the potential for higher binding affinity in a ZFP selected or designed to bind to that site relative to ZFPs that bind to target segments lacking D-able sites.

Figure 2:
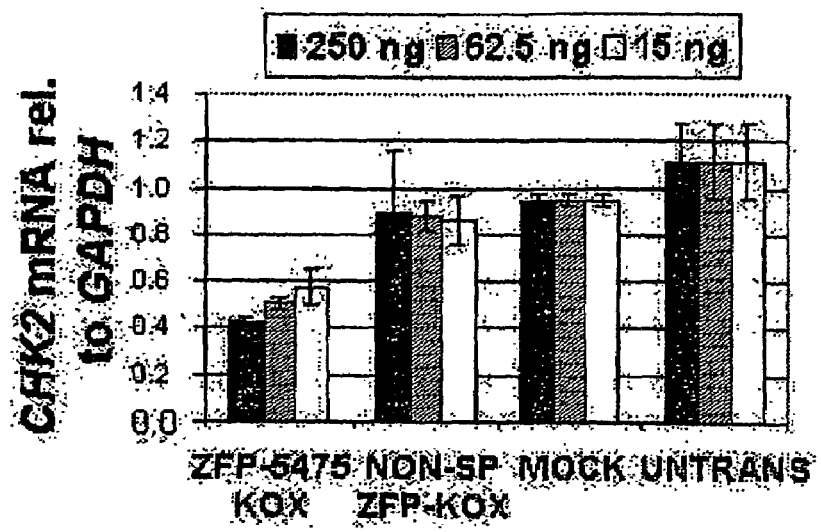
FIG. 2, panels A and B, are graphs depicting regulation of the expression of the endogenous CHK2 gene by ZFP-5475.
Figure 2:
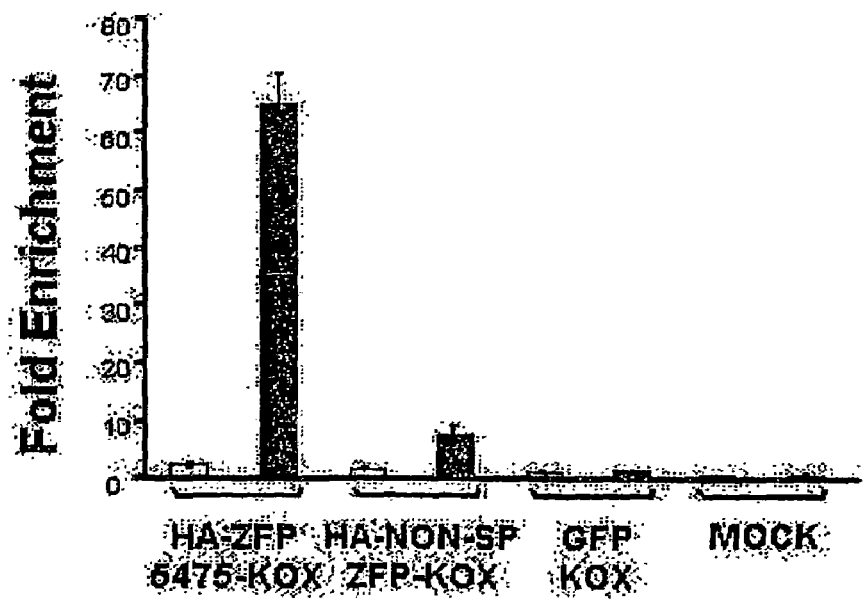

A D-able site or subsite is a region of a target site that allows an appropriately designed single zinc finger to bind to four bases rather than three of the target site. Such a zinc finger binds to a triplet of bases on one strand of a double-stranded target segment (target strand) and a fourth base on the other strand (see FIG. 2 of co-owned U.S. Pat. No. 6,453, 242). Binding of a single zinc finger to a four base target segment imposes constraints both on the sequence of the target strand and on the amino acid sequence of the zinc finger. The target site within the target strand should include the "D-able" site motif 5' NNGK 3', in which N and K are conventional IUPAC-IUB ambiguity codes. A zinc finger for binding to D-able sites typically includes an arginine residue at position −1 and an aspartic acid, (or less preferably a glutamic acid) at position +2. The arginine residues at position −1 interacts with the G residue in the D-able site. The aspartic acid (or glutamic acid) residue at position +2 of the zinc finger interacts with the opposite strand base complementary to the K base in the D-able site. It is the interaction between aspartic acid (symbol D) and the opposite strand base (fourth base) that confers the name D-able site. As is apparent from the D-able site formula, there are two subtypes of D-able sites: 5' NNGG 3' and 5' NNGT 3'. For the former site, the aspartic acid or glutamic acid at position +2 of a zinc finger interacts with a C in the opposite strand to the D-able site. In the latter site, the aspartic acid or glutamic acid at position +2 of a zinc finger interacts with an A in the opposite strand to the D-able site. In general, NNGG is preferred over NNGT.

In the design of a ZFP with three fingers, a target site should be selected in which at least one finger of the protein, and optionally, two or all three fingers have the potential to bind a D-able site. Such can be achieved by selecting a target site from within a larger target gene as described, for example, throughout U.S. Pat. No. 6,453,242.

These methods thus work by selecting a target gene, and systematically searching within the possible subsequences of the gene for target sites, as described above. In some such methods, every possible subsequence of 10 contiguous bases on either strand of a potential target gene is evaluated to determine whether it conforms to the above formula, and, if so, how many D-able sites are present. Typically, such a comparison is performed by computer, and a list of target sites conforming to the formula are output. Optionally, such target sites can be output in different subsets according to how many D-able sites are present.

In a variation, the methods identify first and second target segments, each independently conforming to the above formula. The two target segments in such methods are constrained to be adjacent or proximate (i.e., within about 0-5 bases) of each other in the target gene. The strategy underlying selection of proximate target segments is to allow the design of a ZFP formed by linkage of two component ZFPs specific for the first and second target segments respectively. These principles can be extended to select target sites to be bound by ZFPs with any number of component fingers. For example, a suitable target site for a nine finger protein would have three component segments, each conforming to the above formula.

The target sites identified by the above methods can be subject to further evaluation by other criteria or can be used directly for design or selection (if needed) and production of a ZFP specific for such a site. A further criteria for evaluating potential target sites is their proximity to particular regions within a gene. If a ZFP is to be used to repress a cellular gene on its own (i.e., without linking the ZFP to a repressing moiety), then the optimal location appears to be at, or within 50 bp upstream or downstream of the site of transcription initiation, to interfere with the formation of the transcription complex (Kim & Pabo, *J. Biol. Chem.* 272:29795-296800 (1997)) or compete for an essential enhancer binding protein. If, however, a ZFP is fused to a functional domain such as the KRAB repressor domain or the VP16 activator domain, the location of the binding site is considerably more flexible and can be outside known regulatory regions. For example, a KRAB domain can repress transcription at a promoter up to at least 3 kbp from where KRAB is bound (Margolin et al., *PNAS* 91:4509-4513 (1994)). Thus, target sites can be selected that do not necessarily include or overlap segments of demonstrable biological significance with target genes, such as regulatory sequences. Other criteria for further evaluating target segments include the prior availability of ZFPs binding to such segments or related segments, and/or ease of designing new ZFPs to bind a given target segment.

After a target segment has been selected, a ZFP that binds to the segment can be provided by a variety of approaches. The simplest of approaches is to provide a precharacterized ZFP from an existing collection that is already known to bind to the target site. However, in many instances, such ZFPs do not exist. An alternative approach can also be used to design new ZFPs, which uses the information in a database of existing ZFPs and their respective binding affinities. A further approach is to design a ZFP based on substitution rules as discussed above. A still further alternative is to select a ZFP with specificity for a given target by an empirical process such as phage display. In some such methods, each component finger of a ZFP is designed or selected independently of other component fingers. For example, each finger can be obtained from a different preexisting ZFP or each finger can be subject to separate randomization and selection.

Once a ZFP has been selected, designed, or otherwise provided to a given target segment, the ZFP or the DNA encoding it are synthesized. Exemplary methods for synthesizing and expressing DNA encoding zinc finger proteins are described below. The ZFP or a polynucleotide encoding it can then be used for modulation of expression, or analysis of the target gene containing the target site to which the ZFP binds.

In additional embodiments, zinc finger proteins are designed and synthesized according to methods disclosed in Moore et al. (2001) *Proc. Natl. Acad. Sci. USA* 98:1432-1436; Moore et al. (2001) *Proc. Natl. Acad. Sci. USA* 98:1437-1441; Isalan et al. (2001) *Nature Biotechnol.* 19:656-660 and WO 01/53480.

Expression and Purification of ZFPs

ZFP polypeptides and nucleic acids can be made using routine techniques in the field of recombinant genetics. Basic texts disclosing the general methods of use in the field include Sambrook et al, *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). In addition, essentially any nucleic acid can be custom ordered from any of a variety of commercial sources. Similarly, peptides and antibodies can be custom ordered from any of a variety of commercial sources.

Two alternative methods are typically used to create the coding sequences required to express newly designed DNA-binding peptides. One protocol is a PCR-based assembly procedure that utilizes six overlapping oligonucleotides. Three oligonucleotides correspond to "universal" sequences that encode portions of the DNA-binding domain between the recognition helices. These oligonucleotides remain constant for all zinc finger constructs. The other three "specific" oligonucleotides are designed to encode the recognition helices. These oligonucleotides contain substitutions primarily at positions −1, 2, 3 and 6 on the recognition helices making them specific for each of the different DNA-binding domains.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by high-fidelity thermostable polymerase, the combination of Taq and Pfu polymerases also suffices. In the second phase of construction, the zinc finger template is amplified by external primers designed to incorporate restriction sites at either end for cloning into a shuttle vector or directly into an expression vector.

An alternative method of cloning the newly designed DNA-binding proteins relies on annealing complementary oligonucleotides encoding the specific regions of the desired ZFP. This particular application requires that the oligonucleotides be phosphorylated prior to the final ligation step. This is usually performed before setting up the annealing reactions, but kinasing can also occur post-annealing. In brief, the "universal" oligonucleotides encoding the constant regions of the proteins (oligos 1, 2 and 3 of above) are annealed with their complementary oligonucleotides. Additionally, the "specific" oligonucleotides encoding the finger recognition helices are annealed with their respective complementary oligonucleotides. These complementary oligos are designed to fill in the region which was previously filled in by polymerase in the protocol described above. The complementary oligos to the common oligos 1 and finger 3 are engineered to leave overhanging sequences specific for the restriction sites used in cloning into the vector of choice. The second assembly protocol differs from the initial protocol in the following aspects: the "scaffold" encoding the newly designed ZFP is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment The resulting fragment encoding the newly designed ZFP is ligated into an expression vector. Expression vectors that are commonly utilized include, but are not limited to, a modified pMAL-c2 bacterial expression vector (New England BioLabs, "NEB") or a eukaryotic expression vector, pcDNA (Promega).

Any suitable method of protein purification known to those of skill in the art can be used to purify ZFPs (see Ausubel, supra, Sambrook, supra). In addition, any suitable host can be used, e.g., bacterial cells, insect cells, yeast cells, mammalian cells, and the like.

In one embodiment, expression of the ZFP fused to a maltose binding protein (MBP-ZFP) in bacterial strain JM109 allows for straightforward purification through an amylose column (NEB). High expression levels of the zinc finger chimeric protein can be obtained by induction with IPTG since the MBP-ZFP fusion in the pMal-c2 expression plasmid is under the control of the IPTG inducible tac promoter (NEB). Bacteria containing the MBP-ZFP fusion plasmids are inoculated in to 2xYT medium containing 10 µM $ZnCl_2$, 0.02% glucose, plus 50 µg/ml ampicillin and shaken at 37° C. At mid-exponential growth IPTG is added to 0.3 mM and the cultures are allowed to shake. After 3 hours the bacteria are harvested by centrifugation, disrupted by sonication, and then insoluble material is removed by centrifugation. The MBP-ZFP proteins are captured on an amylose-bound resin, washed extensively with buffer containing 20 mM Tris-HCl (pH 7.5), 200 mM NaCl, 5 mM DTT and 50 µM $ZnCl_2$, then eluted with maltose in essentially the same buffer (purification is based on a standard protocol from NEB). Purified proteins are quantitated and stored for biochemical analysis.

The biochemical properties of the purified proteins, e.g., $K_d$, can be characterized by any suitable assay. In one embodiment, $K_d$ is characterized via electrophoretic mobility shift assays ("EMSA") (Buratowski & Chodosh, in *Current Protocols in Molecular Biology* pp. 12.2.1-12.2.7 (Ausubel ed., 1996); see also U.S. Pat. No. 5,789,538 and co-owned U.S. Pat. No. 6,453,242 herein incorporated by reference in its entirety, and Example 1). Affinity is measured by titrating purified protein against a low fixed amount of labeled double-stranded oligonucleotide target. The target comprises the natural binding site sequence (9 or 18 bp) flanked by the 3 bp found in the natural sequence. External to the binding site plus flanking sequence is a constant sequence. The annealed oligonucleotide targets possess a 1 bp 5' overhang which allows for efficient labeling of the target with T4 phage polynucleotide kinase. For the assay the target is added at a concentration of 40 nM or lower (the actual concentration is kept at least 10-fold lower than the lowest protein dilution) and the reaction is allowed to equilibrate for at least 45 min. In addition the reaction mixture also contains 10 mM Tris (pH 7.5), 100 mM KCl, 1 mM $MgCl_2$, 0.1 mM $ZnCl_2$, 5 mM DTT, 10% glycerol, 0.02% BSA (poly (dIdC) or (dAdT) (Pharmacia) can also added at 10-100 µg/µl).

The equilibrated reactions are loaded onto a 10% polyacrylamide gel, which has been pre-run for 45 min in Tris/glycine buffer, then bound and unbound labeled target is resolved be electrophoresis at 150V (alternatively, 10-20% gradient Tris-HCl gels, containing a 4% polyacrylamide stacker, can be used). The dried gels are visualized by autoradiography or phosphoroimaging and the apparent $K_d$ is determined by calculating the protein concentration that gives half-maximal binding.

Similar assays can also include determining active fractions in the protein preparations. Active fractions are determined by stoichiometric gel shifts where proteins are titrated against a high concentration of target DNA. Titrations are done at 100, 50, and 25% of target (usually at micromolar levels).

In another embodiment, phage display libraries can be used to select ZFPs with high affinity to the selected target site. This method differs fundamentally from direct design in that it involves the generation of diverse libraries of mutagenized ZFPs, followed by the isolation of proteins with desired DNA-binding properties using affinity selection methods. To use this method, the experimenter typically proceeds as follows.

First, a gene for a ZFP is mutagenized to introduce diversity into regions important for binding specificity and/or affinity. In a typical application, this is accomplished via randomization of a single finger at positions −1, +2, +3, and +6, and perhaps accessory positions such as +1, +5, +8, or +10.

Next, the mutagenized gene is cloned into a phage or phagemid vector as a fusion with, e.g., gene III of filamentous phage, which encodes the coat protein pIII. The zinc finger gene is inserted between segments of gene III encoding the membrane export signal peptide and the remainder of pIII, so that the ZFP is expressed as an amino-terminal fusion with pIII in the mature, processed protein. When using phagemid vectors, the mutagenized zinc finger gene may also be fused to a truncated version of gene III encoding, minimally, the C-terminal region required for assembly of pIII into the phage particle.

The resultant vector library is transformed into *E. coli* and used to produce filamentous phage which express variant ZFPs on their surface as fusions with the coat protein pIII (if a phagemid vector is used, then the this step requires superinfection with helper phage). The phage library is then incubated with target DNA site, and affinity selection methods are used to isolate phage which bind target with high affinity from bulk phage. Typically, the DNA target is immobilized on a solid support, which is then washed under conditions sufficient to remove all but the tightest binding phage. After washing, any phage remaining on the support are recovered via elution under conditions which totally disrupt zinc finger-DNA binding.

Recovered phage are used to infect fresh *E. coli*, which is then amplified and used to produce a new batch of phage particles. The binding and recovery steps are then repeated as many times as is necessary to sufficiently enrich the phage pool for tight binders such that these may be identified using sequencing and/or screening methods.

Regulatory Domains

Binding domains such as, for example, ZFPs can optionally be associated with regulatory domains for modulation of gene expression. The ZFP can be covalently or non-covalently associated with one or more regulatory domains, alternatively two or more regulatory domains, with the two or more domains being two copies of the same domain, or two different domains. The regulatory domains can be covalently linked to the ZFP, e.g., via an amino acid linker, as part of a fusion protein. The ZFPs can also be associated with a regulatory domain via a non-covalent dimerization domain, e.g., a leucine zipper, a STAT protein N terminal domain, or an FK506 binding protein (see, e.g., O'Shea, *Science* 254: 539 (1991), Barahmand-Pour et al., *Curr. Top. Microbiol. Immunol.* 211:121-128 (1996); Klemm et al., *Annu. Rev. Immunol.* 16:569-592 (1998); Klemm et al., *Annu. Rev. Immunol.* 16:569-592 (1998); Ho et al, *Nature* 382:822-826 (1996); and Pomeranz et al., *Biochem.* 37:965 (1998)). The regulatory domain can be associated with the ZFP at any suitable position, including the C- or N-terminus of the ZFP.

Common regulatory domains for addition to the ZFP include, e.g., effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers.

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., *Cell* 84:825-30 (1996) for a review of proteins and nucleic acid elements involved in transcription; transcription factors in general are reviewed in Barnes & Adcock, *Clin. Exp. Allergy* 25 Suppl. 2:46-9 (1995) and Roeder, *Methods Enzymol.* 273:165-71 (1996)). Databases dedicated to transcription factors are known (see, e.g., *Science* 269:630 (1995)). Nuclear hormone receptor transcription factors are described in, for example, Rosen et al., *J. Med. Chem.* 38:4855-74 (1995). The C/EBP family of transcription factors are reviewed in Wedel et al., *Immunobiology* 193:171-85 (1995).

Coactivators and co-repressors that mediate transcription regulation by nuclear hormone receptors are reviewed in, for example, Meier, *Eur. J. Endocrinol.* 134(2):158-9 (1996); Kaiser et al, *Trends Biochem. Sci.* 21:342-5 (1996); and Utley et al., *Nature* 394:498-502 (1998)). GATA transcription factors, which are involved in regulation of hematopoiesis, are described in, for example, Simon, *Nat. Geizet.* 11:9-11 (1995); Weiss et al., *Exp. Hematol.* 23:99-107. TATA box binding protein (TBP) and its associated TAF polypeptides (which include TAF30, TAF55, TAF80, TAF110, TAF150, and TAF250) are described in Goodrich & Tjian, *Curr. Opin. Cell Biol.* 6:403-9 (1994) and Hurley, *Curr. Opin. Struct. Biol.* 6:69-75 (1996). The STAT family of transcription factors are reviewed in, for example, Barahmand-Pour et al., *Curr. Top. Microbiol Immunol.* 211:121-8 (1996). Transcription factors involved in disease are reviewed in Aso et al., *J. Clin. Invest.* 97:1561-9 (1996).

In one embodiment, the KRAB repression domain from the human KOX-1 protein is used as a transcriptional repressor (Thiesen et al., *New Biologist* 2:363-374 (1990); Margolin et al., *PNAS* 91:4509-4513 (1994); Pengue et al., *Nucl. Acids Res.* 22:2908-2914 (1994); Witzgall et al., *PNAS* 91:4514-4518 (1994)). In another embodiment, KAP-1, a KRAB co-repressor, is used with KRAB (Friedman et al., *Genes Dev.* 10:2067-2078 (1996)). Alternatively, KAP-1 can be used alone with a ZFP. Other preferred transcription factors and transcription factor domains that act as transcriptional repressors include MAD (see, e.g., Sommer et al., *J. Biol. Chem.* 273:6632-6642 (1998); Gupta et al., *Oncogene* 16:1149-1159 (1998); Queva et al., *Oncogene* 16:967-977 (1998); Larsson et al., *Oncogene* 15:737-748 (1997); Laherty et al., *Cell* 89:349-356 (1997); and Cultraro et al., *Mol Cell. Biol.* 17:2353-2359 (19977)); FKHR (forkhead in rhapdosarcoma gene; Ginsberg et al., *Cancer Res.* 15:3542-3546 (1998); Epstein et al., *Mol. Cell. Biol.* 18:4118-4130 (1998)); EGR-1 (early growth response gene product-1; Yan et al., *PNAS* 95:8298-8303 (1998); and Liu et al., *Cancer Gene Ther.* 5:3-28 (1998)); the ets2 repressor factor repressor domain (ERD; Sgouras et al., *EMBO J.* 14:4781-4793 ((19095)); and the MAD smSIN3 interaction domain (SID; Ayer et al., *Mol. Cell. Biol.* 16:5772-5781 (1996)).

In one embodiment, the HSV VP16 activation domain is used as a transcriptional activator (see, e.g., Hagmann et al., *J. Virol.* 71:5952-5962 (1997)). Other preferred transcription factors that could supply activation domains include the VP64 activation domain (Seipel et al., *EMBO J.* 11:4961-4968 (1996)); nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, *Neuroreport* 8:2937-2942 (1997)); and EGR-1 (early growth response gene product-1; Yan et al., *PNAS* 95:8298-8303 (1998); and Liu et al., *Cancer Gene Ther.* 5:3-28 (1998)).

Kinases, phosphatases, and other proteins that modify polypeptides involved in gene regulation are also useful as regulatory domains for ZFPs. Such modifiers are often involved in switching on or off transcription mediated by, for example, hormones. Kinases involved in transcription regulation are reviewed in Davis, *Mol. Reprod. Dev.* 42:459-67 (1995), Jackson et al., *Adv. Second Messenger Phosphoprotein Res.* 28:279-86 (1993), and Boulikas, *Crit. Rev. Eukaryot. Gene Expr.* 5:1-77 (1995), while phosphatases are reviewed in, for example, Schonthal & Semin, *Cancer Biol.* 6:239-48 (1995). Nuclear tyrosine kinases are described in Wang, *Trends Biochem. Sci.* 19:373-6 (1994).

As described, useful domains can also be obtained from the gene products of oncogenes (e.g., myc, jun, fos, myb, max, mad, rel, ets, bcl, myb, mos family members) and their associated factors and modifiers. Oncogenes are described in, for example, Cooper, *Oncogenes,* 2nd ed., The Jones and Bartlett Series in Biology, Boston, Mass., Jones and Bartlett Publishers, 1995. The ets transcription factors are reviewed in Waslylk et al., *Eur. J. Biochem.* 211:7-18 (1993) and Crepieux et al., *Crit. Rev. Oncog.* 5:615-38 (1994). Myc oncogenes are reviewed in, for example, Ryan et al., *Biochem. J.* 314:713-21 (1996). The jun and fos transcription factors are described in, for example, *The Fos and Jun Families of Transcription Factors,* Angel & Herrlich, eds. (1994). The max oncogene is reviewed in Hurlin et al., Cold Spring Harb. Symp. Quant. Biol. 59:109-16. The myb gene family is reviewed in Kanei-Ishii et al., *Curr. Top. Microbiol. Immunol.* 211:89-98 (1996). The mos family is reviewed in Yew et al., *Curr. Opin. Genet. Dev.* 3:19-25 (1993).

ZFPs can include regulatory domains obtained from DNA repair enzymes and their associated factors and modifiers. DNA repair systems are reviewed in, for example, Vos, *Curr. Opin. Cell Biol.* 4:385-95 (1992); Sancar, *Ann. Rev. Genet.* 29:69-105 (1995); Lehmann, *Genet. Eng.* 17:1-19 (1995); and Wood, *Ann. Rev. Biochem.* 65:135-67 (1996). DNA rearrangement enzymes and their associated factors and modifiers can also be used as regulatory domains (see, e.g., Gangloff et al., *Experientia* 50:261-9 (1994); Sadowski, *FASEB J.* 7:760-7 (1993)).

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al., *Bioessays,* 16:13-22 (1994), and methyltransferases are described in Cheng, *Curr. Opin. Struct. Biol.* 5:4-10 (1995). Chromatin associated proteins and their modifiers (e.g., kinases, acetylases and deacetylases), such as histone deacetylase (Wolffe, *Science* 272:371-2 (1996)) are also useful as domains for addition to the ZFP of choice. In one preferred embodiment, the regulatory domain is a DNA methyl transferase that acts as a transcriptional repressor (see, e.g., Van den Wyngaert et al., *FEBS Lett.* 426:283-289 (1998); Flynn et al., *J. Mol. Biol.* 279:101-116 (1998); Okano et al., *Nucleic Acids Res.* 26:2536-2540 (1998); and Zardo & Caiafa, *J. Biol. Chem.* 273:16517-16520 (1998)).

In additional embodiments, cleavage domains and/or cleavage half-domains (obtained, for example, from restriction enzymes and/or Type IIS endonucleases such as FokI) or functional fragments thereof, are fused to a ZFP. A "cleavage domain" comprises one or more polypeptide sequences which possesses catalytic activity for DNA cleavage. A cleavage domain can be contained in a single polypeptide chain or cleavage activity can result from the association of two (or more) polypeptides. A "cleavage half-domain" is a polypeptide sequence which, in conjunction with a second polypeptide (either identical or different) forms a complex having cleavage activity (e.g., a polypeptide dimer having cleavage activity). Such fusions can be used, for example, for targeted cleavage of cellular chromatin, targeted recombination, and/or gene correction as disclosed, for example, in co-owned U.S. provisional patent application Ser. No. 60/493,931. Such fusions can also be used as transcriptional repressors, which act via gene cleavage (see, e.g., U.S. Pat. Nos. 6,265,196; 5,916,794; 5,792,640; 5,487,994; 5,436,150; and 5,356,802; and PCT/US94/01201).

Factors that control chromatin and DNA structure, movement and localization and their associated factors and modifiers; factors derived from microbes (e.g., prokaryotes, eukaryotes and virus) and factors that associate with or modify them can also be used to obtain chimeric proteins. In one embodiment, recombinases and integrases are used as regulatory domains. In one embodiment, histone acetyltransferase is used as a transcriptional activator (see, e.g., Jin & Scotto, *Mol. Cell. Biol.* 18:4377-4384 (1998); Wolffe, *Science* 272:371-372 (1996); Taunton et al., *Science* 272:408-411 (1996); and Hassig et al., *PNAS* 95:3519-3524 (1998)). In another embodiment, histone deacetylase is used as a transcriptional repressor (see, e.g., Jin & Scotto, *Mol. Cell Biol.* 18:4377-4384 (1998); Syntichaki & Thireos, *J. Biol. Chem.* 273:24414-24419 (1998); Sakaguchi et al, *Genes Dev.* 12:2831-2841 (1998); and Martinez et al., *J. Biol. Chem.* 273:23781-23785 (1998)).

Another suitable repression domain is methyl binding domain protein 2B (MBD-2B) (see, also Hendrich et al. (1999) *Mamm Genome* 10:906-912 for description of MBD proteins). Another useful repression domain is that associated with the v-ErbA protein (see infra). See, for example, Damm, et al. (1989) *Nature* 339:593-597; Evans (1989) *Int. J. Cancer Suppl.* 4:26-28; Pain et al. (1990) *New Biol.* 2:284-294; Sap et al. (1989) *Nature* 340:242-244; Zenke et al. (1988) *Cell* 52:107-119; and Zenke et al. (1990) *Cell* 61:1035-1049. Additional exemplary repression domains include, but are not limited to, thyroid hormone receptor (TR, see infra), SID, MBD1, MBD2, MBD3, MBD4, MBD-like proteins, members of the DNMT family (e.g., DNMT1, DNMT3A, DNMT3B), Rb, MeCP1 and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chern et al. (1996) *Plant Cell* 8:305-321; and Wu et al. (2000) *Plant J.* 22:19-27.

Certain members of the nuclear hormone receptor (NHR) superfamily, including, for example, thyroid hormone receptors (TRs) and retinoic acid receptors (RARs) are among the most potent transcriptional regulators currently known. Zhang et al., *Annu. Rev. Physiol.* 62:439-466 (2000) and Sucov et al., *Mol Neurobiol* 10(2-3):169-184 (1995). In the absence of their cognate ligand, these proteins bind with high specificity and affinity to short stretches of DNA (e.g., 12-17 base pairs) within regulatory loci (e.g., enhancers and promoters) and effect robust transcriptional repression of adjacent genes. The potency of their regulatory action stems from the concurrent use of two distinct functional pathways to drive gene silencing: (i) the creation of a localized domain of repressive chromatin via the targeting of a complex between the corepressor N-CoR and a histone deacetylase, HDAC3 (Guenther et al., *Genes Dev* 14:1048-1057 (2000); Urnov et al., *EMBO J* 19:4074-4090 (2000); Li et al., *EMBO J* 19, 4342-4350 (2000) and Underhill et al., *J. Biol. Chem.* 275: 40463-40470 (2000)) and (ii) a chromatin-independent pathway (Urnov et al., supra) that may involve direct interference with the function of the basal transcription machinery (Fondell et al., *Genes Dev* 7(7B): 1400-1410 (1993) and Fondell et al., *Mol Cell Biol* 16:281-287 (1996).

In the presence of very low (e.g., nanomolar) concentrations of their ligand, these receptors undergo a conformational change which leads to the release of corepressors, recruitnent of a different class of auxiliary molecules (e.g., coactivators) and potent transcriptional activation. Collingwood et al, *J. Mol. Endocrinol.* 23(3):255-275 (1999).

The portion of the receptor protein responsible for transcriptional control (e.g., repression and activation) can be physically separated from the portion responsible for DNA binding, and retains full functionality when tethered to other polypeptides, for example, other DNA-binding domains.

Accordingly, a nuclear hormone receptor transcription control domain can be fused to a ZFP DNA-binding domain such that the transcriptional regulatory activity of the receptor can be targeted to a chromosomal region of interest (e.g., a gene) by virtue of the ZFP binding domain.

Moreover, the structure of TR and other nuclear hormone receptors can be altered, either naturally or through recombinant techniques, such that it loses all capacity to respond to hormone (thus losing its ability to drive transcriptional activation), but retains the ability to effect transcriptional repression. This approach is exemplified by the transcriptional regulatory properties of the oncoprotein v-ErbA. The v-ErbA protein is one of the two proteins required for leukemic transformation of immature red blood cell precursors in young chicks by the avian erythroblastosis virus. TR is a major regulator of erythropoiesis (Beug et al., *Biochim Biophys Acta* 1288(3):M35-47 (1996); in particular, in its unliganded state, it represses genes required for cell cycle arrest and the differentiated state. Thus, the administration of thyroid hormone to immature erythroblasts leads to their rapid differentiation. The v-ErbA oncoprotein is an extensively mutated version of TR; these mutations include: (i) deletion of 12 amino-terminal amino acids; (ii) fusion to the gag oncoprotein; (iii) several point mutations in the DNA binding domain that alter the DNA binding specificity of the protein relative to its parent, TR, and impair its ability to heterodimerize with the retinoid X receptor; (iv) multiple point mutations in the ligand-binding domain of the protein that effectively eliminate the capacity to bind thyroid hormone; and (v) a deletion of a carboxy-terminal stretch of amino acids that is essential for transcriptional activation. Stunnenberg et al, *Biochim Biophys Acta* 1423(1):F15-33 (1999). As a consequence of these mutations, v-ErbA retains the capacity to bind to naturally occurring TR target genes and is an effective transcriptional repressor when bound (Urnov et al., supra; Sap et al., *Nature* 340:242-244 (1989); and Ciana et al., *EMBO J.* 17(24):7382-7394 (1999). In contrast to TR, however, v-ErbA is completely insensitive to thyroid hormone, and thus maintains transcriptional repression in the face of a challenge from any concentration of thyroids or retinoids, whether endogenous to the medium, or added by the investigator.

This functional property of v-ErbA is retained when its repression domain is fused to a heterologous, synthetic DNA binding domain. Accordingly, in one aspect, v-ErbA or its functional fragments are used as a repression domain. In additional embodiments, TR or its functional domains are used as a repression domain in the absence of ligand and/or as an activation domain in the presence of ligand (e.g. 3,5,3'-triiodo-L-thyronine or T3). Thus, TR can be used as a switchable functional domain (i.e., a bifunctional domain); its activity (activation or repression) being dependent upon the presence or absence (respectively) of ligand.

Additional exemplary repression domains are obtained from the DAX protein and its functional fragments. Zazopoulos et al., *Nature* 390:311-315 (1997). In particular, the C-terminal portion of DAX-1, including amino acids 245-470, has been shown to possess repression activity. Altincicek et al., *J. Biol. Chem.* 275:7662-7667 (2000). A further exemplary repression domain is the RBP1 protein and its functional fragments. Lai et al., *Oncogene* 18:2091-2100 (1999); Lai et al., *Mol. Cell. Biol.* 19:6632-6641 (1999); Lai et al., *Mol. Cell. Biol.* 21:2918-2932 (2001) and WO 01/04296. The full-length RBP1 polypeptide contains 1257 amino acids. Exemplary functional fragments of RBP1 are a polypeptide comprising amino acids 1114-1257, and a polypeptide comprising amino acids 243-452.

Members of the TIEG family of transcription factors contain three repression domains known as R1, R2 and R3. Repression by TIEG family proteins is achieved at least in part through recruitment of mSIN3A histone deacetylases complexes. Cook et al. (1999) *J. Biol. Chem.* 274:29,500-29,504; Zhang et al. (2001) *Mol. Cell. Biol.* 21:5041-5049. Any or all of these repression domains (or their functional fragments) can be fused alone, or in combination with additional repression domains (or their functional fragments), to a DNA-binding domain to generate a targeted exogenous repressor molecule.

Furthermore, the product of the human cytomegalovirus (HCMV) UL34 open reading frame acts as a transcriptional repressor of certain HCMV genes, for example, the US3 gene. LaPierre et al (2001) *J. Virol.* 75:6062-6069. Accordingly, the UL34 gene product, or functional fragments thereof, can be used as a component of a fusion polypeptide also comprising a zinc finger binding domain. Nucleic acids encoding such fusions are also useful in the methods and compositions disclosed herein.

Yet another exemplary repression domain is the CDF-1 transcription factor and/or its functional fragments. See, for example, WO 99/27092.

The Ikaros family of proteins are involved in the regulation of lymphocyte development, at least in part by transcriptional repression. Accordingly, an Ikaros family member (e.g., Ikaros, Aiolos) or a functional fragment thereof, can be used as a repression domain. See, for example, Sabbattini et al. (2001) *EMBO J.* 20:2812-2822.

The yeast Ash1p protein comprises a transcriptional repression domain. Maxon et al. (2001) *Proc. Natl. Acad. Sci. USA* 98:1495-1500. Accordingly, the Ash1p protein, its functional fragments, and homologues of Ash1p, such as those found, for example, in, vertebrate, mammalian, and plant cells, can serve as a repression domain for use in the methods and compositions disclosed herein.

Additional exemplary repression domains include those derived from histone deacetylases (HDACs, e.g., Class I HDACs, Class II HDACs, SIR-2 homologues), HDAC-interacting proteins (e.g., SIN3, SAP30, SAP15, NCoR, SMRT, RB, p107, p130, RBAP46/48, MTA, Mi-2, Brg1, Brm), DNA-cytosine methyltransferases (e.g., Dnmt1, Dnmt3a, Dnmt3b), proteins that bind methylated DNA (e.g. MBD1, MBD2, MBD3, MBD4, MeCP2, DMAP1), protein methyltransferases (e.g., lysine and arginine methylases, SuVar homologues such as Suv39H1), polycomb-type repressors (e.g., Bmi-1, eed1, RING1, RYBP, E2F6, Mel18, YY1 and CtBP), viral repressors (e.g., adenovirus E1b 55K protein, cytomegalovirus UL34 protein, viral oncogenes such as v-erbA), hormone receptors (e.g., Dax-1, estrogen receptor, thyroid hormone receptor), and repression domains associated with naturally-occurring zinc finger proteins (e.g., WT1, KAP1). Further exemplary repression domains include members of the polycomb complex and their homologues, HPH1, HPH2, HPC2, NC2, groucho, Eve, tramtrak, mHP1, SIP1, ZEB1, ZEB2, and Enx1/Ezh2. In all of these cases, either the full-length protein or a functional fragment can be used as a repression domain for fusion to a zinc finger binding domain. Furthermore, any homologues of the aforementioned proteins can also be used as repression domains, as can proteins (or their functional fragments) that interact with any of the aforementioned proteins.

Additional repression domains, and exemplary functional fragments, are as follows. Hes1 is a human homologue of the *Drosophila hairy* gene product and comprises a functional fragment encompassing amino acids 910-1014. In particular, a WRPW (trp-arg-pro-trp) motif can act as a repression domain. Fisher et al. (1996) *Mol. Cell. Biol.* 16:2670-2677.

The TLE1, TLE2 and TLE3 proteins are human homologues of the *Drosophila groucho* gene product. Functional fragments of these proteins possessing repression activity reside between amino acids 1-400. Fisher et al., supra.

The Tbx3 protein possesses a functional repression domain between amino acids 524-721. He et al. (1999) *Proc. Natl. Acad. Sci. USA* 96:10,212-10,217. The Tbx2 gene product is involved in repression of the p14/p16 genes and contains a region between amino acids 504-702 that is homologous to the repression domain of Tbx3; accordingly Tbx2 and/or this functional fragment can be used as a repression domain. Carreira et al. (1998) *Mol. Cell. Biol.* 18:5,099-5,108.

The human Ezh2 protein is a homologue of *Drosophila* enhancer of zeste and recruits the eed1 polycomb-type repressor. A region of the Ezh2 protein comprising amino acids 1-193 can interact with eed1 and repress transcription; accordingly Ezh2 and/or this functional fragment can be used as a repression domain. Denisenko et al. (1998) *Mol. Cell. Biol.* 18:5634-5642.

The RYBP protein is a corepressor that interacts with polycomb complex members and with the YY1 transcription factor. A region of RYBP comprising amino acids 42-208 has been identified as functional repression domain. Garcia et al. (1999) *EMBO J.* 18:3404-3418.

The RING finger protein RING1A is a member of two different vertebrate polycomb-type complexes, contains multiple binding sites for various components of the polycomb complex, and possesses transcriptional repression activity. Accordingly, RING1A or its functional fragments can serve as a repression domain. Satjin et al. (1997) *Mol. Cell. Biol.* 17:4105-4113.

The Bmi-1 protein is a member of a vertebrate polycomb complex and is involved in transcriptional silencing. It contains multiple binding sites for various polycomb complex components. Accordingly, Bmi-1 and its functional fragments are useful as repression domains. Gunster et al. (1997) *Mol. Cell. Biol.* 17:2326-2335; Hemenway et al. (1998) *Oncogene* 16:2541-2547.

The E2F6 protein is a member of the mammalian Bmi-1-containing polycomb complex and is a transcriptional repressor that is capable or recruiting RYBP, Bmi-1 and RING1A. A functional fragment of E2F6 comprising amino acids 129-281 acts as a transcriptional repression domain. Accordingly, E2F6 and its functional fragments can be used as repression domains. Trimarchi et al. (2001) *Proc Natl. Acad. Sci. USA* 98:1519-1524.

The eed1 protein represses transcription at least in part through recruitment of histone deacetylases (e.g., HDAC2). Repression activity resides in both the N- and C-terminal regions of the protein. Accordingly, eed1 and its functional fragments can be used as repression domains. van der Vlag et al. (1999) *Nature Genet.* 23:474-478.

The CTBP2 protein represses transcription at least in part through recruitment of an HPC2-polycomb complex. Accordingly, CTBP2 and its functional fragments are useful as repression domains. Richard et al. (1999) *Mol. Cell. Biol.* 19:777-787.

Neuron-restrictive silencer factors are proteins that repress expression of neuron-specific genes. Accordingly, a NRSF or functional fragment thereof can serve as a repression domain. See, for example, U.S. Pat. No. 6,270,990.

It will be clear to those of skill in the art that, in the formation of a fusion protein (or a nucleic acid encoding same) between a zinc finger binding domain and a functional domain, either a repressor or a molecule that interacts with a repressor is suitable as a functional domain. Essentially any molecule capable of recruiting a repressive complex and/or repressive activity (such as, for example, histone deacetylation) to the target gene is useful as a repression domain of a fusion protein.

Additional exemplary activation domains include, but are not limited to, p300, CBP, PCAF, SRC1 PvALF, AtHD2A and ERF-2. See, for example, Robyr et al. (2000) Mol. Endocrinol. 14:329-347; Collingwood et al. (1999) J. Mol. Endocrinol. 23:255-275; Leo et al. (2000) Gene 245: 1-11; Manteuffel-Cymborowska (1999) Acta Biochim. Pol. 46:77-89; McKenna et al. (1999) J. Steroid Biochem. Mol. Biol. 69:3-12; Malik et al. (2000) Trends Biochem. Sci. 25:277-283; and Lemon et al. (1999) Curr. Opin. Genet. Dev. 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) Gene 245:21-29; Okanami et al. (1996) Genes Cells 1:87-99; Goff et al. (1991) Genes Dev. 5:298-309; Cho et al. (1999) Plant Mol. Biol. 40:419-429; Ulmason et al. (1999) Proc. Natl. Acad. Sci. USA 96:5844-5849; Sprenger-Haussels et al. (2000) Plant J. 22:1-8; Gong et al. (1999) Plant Mol. Biol. 41:33-44; and Hobo et al. (1999) Proc. Natl. Acad. Sci. USA 96:15,348-15,353.

It will be clear to those of skill in the art that, in the formation of a fusion protein (or a nucleic acid encoding same) between a zinc finger binding domain and a functional domain, either an activator or a molecule that interacts with an activator is suitable as a functional domain. Essentially any molecule capable of recruiting an activating complex and/or activating activity (such as, for example, histone acetylation) to the target gene is useful as an activating domain of a fusion protein.

Insulator domains, chromatin remodeling proteins such as ISWI-containing domains and/or methyl binding domain proteins suitable for use as functional domains in fusion molecules are described, for example, in co-owned WO 01/83793; WO 02/26959; WO 02/26960 and WO 02/44376.

In a further embodiment, a DNA-binding domain (e.g., a zinc finger domain) is fused to a bifunctional domain (BFD). A bifunctional domain is a transcriptional regulatory domain whose activity depends upon interaction of the BFD with a second molecule. The second molecule can be any type of molecule capable of influencing the functional properties of the BFD including, but not limited to, a compound, a small molecule, a peptide, a protein, a polysaccharide or a nucleic acid. An exemplary BFD is the ligand binding domain of the estrogen receptor (ER). In the presence of estradiol, the ER ligand binding domain acts as a transcriptional activator; while, in the absence of estradiol and the presence of tamoxifen or 4-hydroxy-tamoxifen, it acts as a transcriptional repressor. Another example of a BFD is the thyroid hormone receptor (TR) ligand binding domain which, in the absence of ligand, acts as a transcriptional repressor and in the presence of thyroid hormone (T3), acts as a transcriptional activator. An additional BFD is the glucocorticoid receptor (GR) ligand binding domain. In the presence of dexamethasone, this domain acts as a transcriptional activator, while, in the presence of RU486, it acts as a transcriptional repressor. An additional exemplary BFD is the ligand binding domain of the retinoic acid receptor. In the presence of its ligand all-trans-retinoic acid, the retinoic acid receptor recruits a number of co-activator complexes an transcription. In the absence of ligand, the retinoic acid receptor is not capable of recruiting transcriptional co-activators. Additional BFDs are known to those of skill in the art. See, for example, U.S. Pat. Nos. 5,834,266 and 5,994,313 and PCT WO 99/10508.

Another class of functional domain, derived from nuclear receptors, are those whose functional activity is regulated by a non-natural ligand. These are often mutants or modified versions of naturally-occurring receptors and are sometimes referred to as "switchable" domains. For example, certain mutants of the progesterone receptor (PR) are unable to interact with their natural ligand, and are therefore incapable of being transcriptionally activated by progesterone. Certain of these mutants, however, can be activated by binding small molecules other than progesterone (one example of which is the antiprogestin mifepristone). Such non-natural but functionally competent ligands have been denoted anti-hormones. See, e.g., U.S. Pat. Nos. 5,364,791; 5,874,534; 5,935,934; Wang et al, (1994) *Proc. Natl. Acad. Sci. USA* 91:8180-8184; Wang et al. (1997) *Gene Ther.* 4:432-441.

Accordingly, a fusion comprising a targeted ZFP binding domain, a functional domain, and a mutant PR ligand binding domain of this type can be used for mifepristone-dependent activation or repression of an endogenous gene of choice, by designing the ZFP binding domain such that it binds in or near the gene of choice. If the fusion contains an activation domain, mifepristone-dependent activation of gene expression is obtained; if the fusion contains a repression domain, mifepristone-dependent repression of gene expression is obtained. Additionally, polynucleotides encoding such fusion proteins are provided, as are vectors comprising such polynucleotides and cells comprising such polynucleotides and vectors. It will be clear to those of skill in the art that modified or mutant versions of receptors other than PR can also be used as switchable domains. See, for example, Tora et al. (1989) *EMBO J.* 8:1981-1986.

Linker domains between polypeptide domains, e.g., between two ZFPs or between a ZFP and a regulatory domain, can be included. Such linkers are typically polypeptide sequences, such as poly gly sequences of between about 5 and 200 amino acids. Preferred linkers are typically flexible amino acid subsequences which are synthesized as part of a recombinant fusion protein. For example, in one embodiment, the linker DGGGS is used to link two ZFPs. In another embodiment, the flexible linker linking two ZFPs is an amino acid subsequence comprising the sequence TGEKP (SEQ ID NO:19) (see, e.g., Liu et al., *PNAS* 5525-5530 (1997)). In another embodiment, the linker LRQKDGERP (SEQ ID NO:20) is used to link two ZFPs. In another embodiment, the following linkers are used to link two ZFPs: GGRR (SEQ ID NO:21) (Pomerantz et al. 1995, supra), $(G4S)_n$ (SEQ ID NO:22) (Kim et al., *PNAS* 93, 1156-1160 (1996); and GGR-RGGGS (SEQ ID NO:23); LRQRDGERP (SEQ ID NO:24); LRQKDGGGSERP (SEQ ID NO:25); $LRQKd(G3S)_2$ ERP (SEQ ID NO:26). Alternatively, flexible linkers can be rationally designed using computer program capable of modeling both DNA-binding sites and the peptides themselves (Desjarlais & Berg, *PNAS* 90:2256-2260 (1993), *PNAS* 91:11099-11103 (1994) or by phage display methods.

In other embodiments, a chemical linker is used to connect synthetically or recombinantly produced domain sequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages. In addition to covalent linkage of ZFPs to regulatory domains, non-covalent methods can be used to produce molecules with ZFPs associated with regulatory domains.

In addition to regulatory domains, often the ZFP is expressed as a fusion protein such as maltose binding protein ("MBP"), glutathione S transferase (GST), hexahistidine, c-myc, and the FLAG epitope, for ease of purification, monitoring expression, or monitoring cellular and subcellular localization.

Expression Vectors

The nucleic acid encoding the ZFP of choice is typically cloned into intermediate vectors for transformation into prokaryotic or eukaryotic cells for replication and/or expression, e.g., for determination of $K_d$. Intermediate vectors are typically prokaryote vectors, e.g., plasmids, or shuttle vectors, or insect vectors, for storage or manipulation of the nucleic acid encoding ZFP or production of protein. The nucleic acid encoding a ZFP is also typically cloned into an expression vector, for administration to a plant cell, animal cell, preferably a mammalian cell or a human cell, fungal cell, bacterial cell, or protozoal cell.

To obtain expression of a cloned gene or nucleic acid, a ZFP is typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). Bacterial expression systems for expressing the ZFP are available in, e.g., *E. coli, Bacillus* sp., and *Salmonella* (Palva et al, *Gene* 22:229-235 (1983)). Kits for such expression systems are commercially available. Eukaryotic expression systems for mammalian cells, yeast, and insect cells are well known in the art and are also commercially available.

The promoter used to direct expression of a ZFP nucleic acid depends on the particular application. For example, a strong constitutive promoter is typically used for expression and purification of ZFP. In contrast, when a ZFP is administered in vivo for gene regulation, either a constitutive or an inducible promoter is used, depending on the particular use of the ZFP. In addition, a preferred promoter for administration of a ZFP can be a weak promoter, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the ZFP, and signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the ZFP, e.g., expression in plants, animals, bacteria, fungus, protozoa etc. (see expression vectors described below and in the Example section). Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins are used for purification of the ZFP. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a ZFP encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Assays for Determining Regulation of Gene Expression

A variety of assays can be used to determine the level of gene expression regulation by ZFPs. The activity of a particular ZFP can be assessed using a variety of in vitro and in vivo assays, by measuring, e.g., protein or mRNA levels, product levels, enzyme activity, tumor growth; transcriptional activation or repression of a reporter gene; second messenger levels (e.g., cGMP, cAMP, IP3, DAG, $Ca^{2+}$); cytokine and hormone production levels; and neovascularization, using, e.g., immunoassays (e.g., ELISA and immunohistochemical assays with antibodies), hybridization assays (e.g., RNase protection, northerns, in situ hybridization, oligonucleotide array studies), colorimetric assays, amplification assays, enzyme activity assays, tumor growth assays, phenotypic assays, and the like.

ZFPs are typically first tested for activity in vitro using cultured cells, e.g., 293 cells, CHO cells, VERO cells, BHK cells, HeLa cells, COS cells, and the like. Preferably, human cells are used. The ZFP is often first tested using a transient expression system with a reporter gene, and then regulation of the target endogenous gene is tested in cells and in animals, both in vivo and ex vivo. The ZFP can be recombinantly expressed in a cell, recombinantly expressed in cells transplanted into an animal, or recombinantly expressed in a transgenic animal, as well as administered as a protein to an animal or cell using delivery vehicles described below. The cells can be immobilized, be in solution, be injected into an animal, or be naturally occurring in a transgenic or non-transgenic animal.

Modulation of gene expression is tested using one of the in vitro or in vivo assays described herein. Samples or assays are treated with a ZFP and compared to control samples without the test compound, to examine the extent of modulation. As described above, for regulation of endogenous gene expression, the ZFP typically has a $K_d$ of 200 nM or less, more preferably 100 nM or less, more preferably 50 nM, most preferably 25 nM or less.

The effects of the ZFPs can be measured by examining any of the parameters described above. Any suitable gene expression, phenotypic, or physiological change can be used to assess the influence of a ZFP. When the functional consequences are determined using intact cells or animals, one can also measure a variety of effects such as tumor growth, neovascularization, hormone release, transcriptional changes to both known and uncharacterized genetic markers (e.g., northern blots or oligonucleotide array studies), changes in cell metabolism such as cell growth or pH changes, and changes in intracellular second messengers such as cGMP.

Preferred assays for ZFP regulation of endogenous gene expression can be performed in vitro. In one preferred in vitro assay format, ZFP regulation of endogenous gene expression in cultured cells is measured by examining protein production using an ELISA assay. The test sample is compared to control cells treated with an empty vector or an unrelated ZFP that is targeted to another gene.

In another embodiment, ZFP regulation of endogenous gene expression is determined in vitro by measuring the level of target gene mRNA expression The level of gene expression is measured using amplification, e.g., using PCR, LCR, or hybridization assays, e.g., northern hybridization, RNase protection, dot blotting. RNase protection is used in one embodiment. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the target gene promoter operably linked to a reporter gene such as luciferase, green fluorescent protein, CAT, or β-gal. The reporter construct is typically co-transfected into a cultured cell. After treatment with the ZFP of choice, the amount of reporter gene transcription, translation, or activity is measured according to standard techniques known to those of skill in the art.

Another example of a preferred assay format useful for monitoring ZFP regulation of endogenous gene expression is performed in vivo. This assay is particularly useful for examining ZFPs that inhibit expression of tumor promoting genes, genes involved in tumor support, such as neovascularization (e.g., VEGF), or that activate tumor suppressor genes such as p53. In this assay, cultured tumor cells expressing the ZFP of choice are injected subcutaneously into an immune compromised mouse such as an athymic mouse, an irradiated mouse, or a SCID mouse. After a suitable length of time, preferably 4-8 weeks, tumor growth is measured, e.g., by volume or by its two largest dimensions, and compared to the control. Tumors that have statistically significant reduction (using, e.g., Student's T test) are said to have inhibited growth. Alternatively, the extent of tumor neovascularization can also be measured. Immunoassays using endothelial cell specific antibodies are used to stain for vascularization of the tumor and the number of vessels in the tumor. Tumors that have a statistically significant reduction in the number of vessels (using, e.g., Student's T test) are said to have inhibited neovascularization.

Transgenic and non-transgenic animals are also used as a preferred embodiment for examining regulation of endogenous gene expression in vivo. Transgenic animals typically express the ZFP of choice. Alternatively, animals that transiently express the ZFP of choice, or to which the ZFP has been administered in a delivery vehicle, can be used. Regulation of endogenous gene expression is tested using any one of the assays described herein.

Nucleic Acids Encoding Fusion Proteins

Conventional viral and non-viral based gene transfer methods can be used to introduce nucleic acids encoding engineered ZFP in mammalian cells or target tissues. Such methods can be used to administer nucleic acids encoding ZFPs to cells in vitro. Preferably, the nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):3144 (1995); Haddada et al., in *Current Topics in Microbiology and Immunology* Doerfler and Böhm (eds) (1995); and Yu et al., *Gene Therapy* 1:13-26 (1994).

Methods of non-viral delivery of nucleic acids encoding engineered ZFPs include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g. Crystal, *Science* 270:404-410 (1995); Blaese et al, *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFP take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able, to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications where transient expression of the ZFP is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:3847 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panb cells), GR-1 (granulocytes), and Iad (differentiated antigen presenting cells) (see Inaba et al., *J. Exp. Med.* 176:1693-1702 (1992)).

Vectors (e.g., retroviruses, adenoviruses, liposomes, etc.) containing therapeutic ZFP nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

Delivery Vehicles

An important factor in the administration of polypeptide compounds, such as the ZFPs, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ZFPs across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629-634 (1996)). Another subsequence, the h (hydrophobic) domain of signal peptides, was found to have similar cell membrane translocation characteristics (see, e.g., Lin et al., *J. Biol. Client.* 270:1 4255-14258 (1995)).

Examples of peptide sequences which can be linked to a protein, for facilitating uptake of the protein into cells, include, but are not limited to: an 11 amino acid peptide of the tat protein of HIV; a 20 residue peptide sequence which corresponds to amino acids 84-103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223-233 (1997)). Other suitable chemical moieties that provide enhanced cellular uptake may also be chemically linked to ZFPs.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.*, 268:3334-3341 (1993); Perelle et al., *Infect. Immun.*, 61:5147-5156 (1993); Stenmark et al., *J. Cell Biol.* 113:1025-1032 (1991); Donnelly et al., *PNAS* 90:3530-3534 (1993); Carbonetti et al., *Abstr. Annu. Meet. Am. Soc. Microbiol.* 95:295 (1995); Sebo et al., *Infect. Immun.* 63:3851-3857 (1995); Klimpel et al., *PNAS U.S.A.* 89:10277-10281 (1992); and Novak et al., *J. Biol. Chem.* 267:17186-17193 1992)).

Amino acid sequences which facilitate internalization of linked polypeptides into cells can be selected from libraries of randomized peptide sequences. See, for example, Yeh et al. (2003) *Molecular Therapy* 7(5):S461 (Abstract #1191). Such "internalization peptides" can be fused to a zinc finger protein to facilitate entry of the protein into a cell.

Such subsequences, as described above, can be used to translocate ZFPs across a cell membrane. ZFPs can be conveniently fused to or derivatized with such sequences. Typically, the translocation sequence is provided as part of a fusion protein. Optionally, a linker can be used to link the ZFP and the translocation sequence. Any suitable linker can be used, e.g., a peptide linker.

The ZFP can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., a ZFP.

The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a ZFP) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., *PNAS* 84:7851 (1987); *Biochemistry* 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise a ZFP and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g. Szoka et al., *Ann. Rev. Biophys. Bioeng.* 9:467 (1980), U.S. Pat. Nos. 4,186,183, 4,217, 344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91\17424, Deamer & Bangham, *Biochim. Biophys. Acta* 443: 629-634 (1976); Fraley, et al., *PNAS* 76:3348-3352 (1979); Hope et al., *Biochim. Biophys. Acta* 812:55-65 (1985); Mayer et al., *Biochim. Biophys. Acta* 858:161-168 (1986); Williams et al., *PNAS* 85:242-246 (1988); *Liposomes* (Ostro (ed.), 1983, Chapter 1); Hope et al., *Chem. Phys. Lip.* 40:89 (1986); Gregoriadis, *Liposome Technology* (1984) and Lasic, *Liposomes: from Physics to Applications* (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it is desirable to target liposomes using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044).

Examples of targeting moieties include monoclonal antibodies specific to antigens associated with neoplasms, such as prostate cancer specific antigen and MAGE. Tumors can also be diagnosed by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., *J. Biol. Chem.*, 265: 16337-16342 (1990) and Leonetti et al., *PNAS* 87:2448-2451 (1990).

Dosages

For therapeutic applications, the dose administered to a patient, in the context of the present disclosure, should be sufficient to effect a beneficial therapeutic response in the patient over time. In addition, particular dosage regimens can be useful for determining phenotypic changes in an experimental setting, e.g., in functional genomics studies, and in cell or animal models. The dose will be determined by the efficacy and $K_d$ of the particular ZFP employed, the nuclear volume of the target cell, and the condition of the patient, as well as the body weight or surface area of the patient to be treated. The size of the dose also will be determined by the existence, nature, and extent of any adverse side-effects that accompany the administration of a particular compound or vector in a particular patient.

The maximum therapeutically effective dosage of ZFP for approximately 99% binding to target sites is calculated to be in the range of less than about $1.5 \times 10^5$ to $1.5 \times 10^6$ copies of the specific ZFP molecule per cell. The number of ZFPs per cell for this level of binding is calculated as follows, using the volume of a HeLa cell nucleus (approximately 1000 μm$^3$ or $10^{-12}$ L; *Cell Biology*, (Altman & Katz, eds. (1976)). As the HeLa nucleus is relatively large, this dosage number is recalculated as needed using the volume of the target cell nucleus. This calculation also does not take into account competition for ZFP binding by other sites. This calculation also assumes that essentially all of the ZFP is localized to the nucleus. A value of $100 \times K_d$ is used to calculate approximately 99% binding of to the target site, and a value of $10 \times K_d$ is used to calculate approximately 90% binding of to the target site. For this example, $K_d = 25$ nM ZFP+target site↔complex
i.e., DNA+protein↔DNA:protein complex $$K_d = \frac{[DNA][protein]}{[DNA: protein\ complex]}$$

When 50% of ZFP is bound, $K_d$=[protein]
So when [protein]=25 nM and the nucleus volume is $10^{-12}$ L
[protein]=(25×10$^9$ moles/L) (10$^{-12}$ L/nucleus) (6×10$^{23}$ molecules/mole)
=15,000 molecules/nucleus for 50% binding
When 99% target is bound; $100 \times K_d$=[protein]
$100 \times K_d$=[protein]=2.5 μM
(2.5×10$^{-6}$ moles/L) (10$^{-12}$ L/nucleus) (6×10$^{23}$ molecules/mole)
=about 1,500,000 molecules per nucleus for 99% binding of target site.

The appropriate dose of an expression vector encoding a ZFP can also be calculated by taking into account the average rate of ZFP expression from the promoter and the average rate of ZFP degradation in the cell. Preferably, a weak promoter such as a wild-type or mutant HSV TK is used, as described above. The dose of ZFP in micrograms is calculated by taking into account the molecular weight of the particular ZFP being employed.

In determining the effective amount of the ZFP to be administered in the treatment or prophylaxis of disease, the physician evaluates circulating plasma levels of the ZFP or nucleic acid encoding the ZFP, potential ZFP toxicities, progression of the disease, and the production of anti-ZFP antibodies. Administration can be accomplished via single or divided doses.

Pharmaceutical Compositions and Administration

ZFPs and expression vectors encoding ZFPs can be administered directly to the patient for modulation of gene expression and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Examples of microorganisms that can be inhibited by ZFP gene therapy include pathogenic bacteria, e.g., *chlamydia*, rickettsial bacteria, mycobacteria, staphylococci, streptococci, pneumococci, meningococci and conococci, *klebsiella, proteus, serratia, pseudomonas, legionella,* diphtheria, *salmonella,* bacilli, cholera, tetanus, botulism, anthrax, plague, leptospirosis, and Lyme disease bacteria; infectious fungus, e.g., *Aspergillus, Candida* species; protozoa such as sporozoa (e.g., *Plasmodia*), rhizopods (e.g., *Entamoeba*) and flagellates (*Trypanosoma, Leishmania, Trichomonas, Giardia,* etc.); viral diseases, e.g., hepatitis (A, B, or C), herpes virus (e.g., VZV, HSV-1, HSV-6, HSV-II, CMV, and EBV), HIV, Ebola, adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, poliovirus, rabies virus, and arboviral encephalitis virus, etc.

Administration of therapeutically effective amounts is by any of the routes normally used for introducing ZFP into ultimate contact with the tissue to be treated. The ZFPs are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., *Remington's Pharmaceutical Sciences,* 17$^{th}$ ed. 1985)).

The ZFPs, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Regulation of Gene Expression in Plants

ZFPs can be used to engineer plants for traits such as increased disease resistance, modification of structural and storage polysaccharides, flavors, proteins, and fatty acids, fruit ripening, yield, color, nutritional characteristics, improved storage capability, and the like. In particular, the engineering of crop species for enhanced oil production, e.g., the modification of the fatty acids produced in oilseeds, is of interest.

Seed oils are composed primarily of triacylglycerols (TAGs), which are glycerol esters of fatty acids. Commercial production of these vegetable oils is accounted for primarily by six major oil crops (soybean, oil palm, rapeseed, sunflower, cotton seed, and peanut.) Vegetable oils are used predominantly (90%) for human consumption as margarine, shortening, salad oils, and frying oil. The remaining 10% is used for non-food applications such as lubricants, oleochemicals, biofuels, detergents, and other industrial applications.

The desired characteristics of the oil used in each of these applications varies widely, particularly in terms of the chain length and number of double bonds present in the fatty acids making up the TAGs. These properties are manipulated by the plant in order to control membrane fluidity and temperature sensitivity. The same properties can be controlled using ZFPs to produce oils with improved characteristics for food and industrial uses.

The primary fatty acids in the TAGs of oilseed crops are 16 to 18 carbons in length and contain 0 to 3 double bonds. Palmitic acid (16:0 [16 carbons: 0 double bonds]), oleic acid (18:1), linoleic acid (18:2), and linolenic acid (18:3) predominate. The number of double bonds, or degree of saturation, determines the melting temperature, reactivity, cooking performance, and health attributes of the resulting oil.

The enzyme responsible for the conversion of oleic acid (18:1) into linoleic acid (18:2) (which is then the precursor for 18:3 formation) is A12-oleate desaturase, also referred to as omega-6 desaturase. A block at this step in the fatty acid desaturation pathway should result in the accumulation of oleic acid at the expense of polyunsaturates.

In one embodiment ZFPs are used to regulate expression of the FAD2-1 gene in soybeans. Two genes encoding microsomal Δ6 desaturases have been cloned recently from soybean, and are referred to as FAD2-1 and FAD2-2 (Heppard et al., *Plant Physiol.* 110:311-319 (1996)). FAD2-1 (delta 12 desaturase) appears to control the bulk of oleic acid desaturation in the soybean seed. ZFPs can thus be used to modulate gene expression of FAD2-1 in plants. Specifically, ZFPs can be used to inhibit expression of the FAD2-1 gene in soybean in order to increase the accumulation of oleic acid (18:1) in the oil seed. Moreover, ZFPs can be used to modulate expression of any other plant gene, such as delta-9 desaturase, delta-12 desaturases from other plants, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, polygalacturonase, EPSP synthase, plant viral genes, plant fungal pathogen genes, and plant bacterial pathogen genes.

Recombinant DNA vectors suitable for transformation of plant cells are also used to deliver protein (e.g., ZFP)-encoding nucleic acids to plant cells. Techniques for transforming a wide variety of higher plant species are well known and described in the technical and scientific literature (see, e.g., Weising et al. *Ann. Rev. Genet.* 22:421-477 (1988)). A DNA sequence coding for the desired ZFP is combined with transcriptional and translational initiation regulatory sequences which will direct the transcription of the ZFP in the intended tissues of the transformed plant.

For example, a plant promoter fragment may be employed which will direct expression of the ZFP in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the ZFP in a specific tissue or may be otherwise under more precise environmental or developmental control. Such promoters are referred to here as "inducible" promoters. Examples of environmental conditions that may effect transcription by inducible promoters include anaerobic conditions or the presence of light.

Examples of promoters under developmental control include promoters that initiate transcription only in certain tissues, such as fruit, seeds, or flowers. For example, the use of a polygalacturonase promoter can direct expression of the ZFP in the fruit, a CHS-A (chalcone synthase A from petunia) promoter can direct expression of the ZFP in flower of a plant.

The vector comprising the ZFP sequences will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Such DNA constructs may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *EMBO J.* 3:2717-2722 (1984). Electroporation techniques are described in Fromm et al. *PNAS* 82:5824 (1985). Biolistic transformation techniques are described in Klein et al. *Nature* 327:70-73 (1987).

*Agrobacterium tumefaciens*-meditated transformation techniques are well described in the scientific literature (see, e.g., Horsch et al. *Science* 233:496-498 (1984)); and Fraley et al. *PNAS* 80:4803 (1983)).

Transformed plant cells which are derived by any of the above transformation techniques can be cultured to regenerate a whole plant which possesses the transformed genotype and thus the desired ZFP-controlled phenotype. Such regeneration techniques rely on manipulation of certain phytohormones in a tissue culture growth medium, typically relying on a biocide and/or herbicide marker which has been introduced together with the ZFP nucleotide sequences. Plant regeneration from cultured protoplasts is described in Evans et al., *Protoplasts Isolation and Culture, Handbook of Plant Cell Culture*, pp. 124-176 (1983); and Binding, *Regeneration of Plants, Plant Protoplasts*, pp. 21-73 (1985). Regeneration can also be obtained from plant callus, explants, organs, or parts thereof. Such regeneration techniques are described generally in Klee et al. *Ann. Rev. of Plant Phys.* 38:467-486 (1987).

Functional Genomics Assays

ZFPs also have use for assays to determine the phenotypic consequences and function of gene expression. The recent advances in analytical techniques, coupled with focussed mass sequencing efforts have created the opportunity to identify and characterize many more molecular targets than were previously available. This new information about genes and their functions will speed along basic biological understanding and present many new targets for therapeutic intervention. In some cases analytical tools have not kept pace with the generation of new data. An example is provided by recent advances in the measurement of global differential gene expression. These methods, typified by gene expression microarrays, differential cDNA cloning frequencies, subtractive hybridization and differential display methods, can very rapidly identify genes that are up or down-regulated in different tissues or in response to specific stimuli. Increasingly, such methods are being used to explore biological processes such as, transformation, tumor progression, the inflammatory response, neurological disorders etc. One can now very easily generate long lists of differentially expressed genes that correlate with a given physiological phenomenon, but demonstrating a causative relationship between an individual differentially expressed gene and the phenomenon is difficult. Until now, simple methods for assigning function to differentially expressed genes have not kept pace with the ability to monitor differential gene expression.

Using conventional molecular approaches, over expression of a candidate gene can be accomplished by cloning a full-length cDNA, subcloning it into a mammalian expression vector and transfecting the recombinant vector into an appropriate host cell. This approach is straightforward but labor intensive, particularly when the initial candidate gene is represented by a simple expressed sequence tag (EST). Under expression of a candidate gene by "conventional" methods is yet more problematic. Antisense methods and methods that rely on targeted ribozymes are unreliable, succeeding for only a small fraction of the targets selected. Gene knockout by homologous recombination works fairly well in recombinogenic stem cells but very inefficiently in somatically derived cell lines. In either case large clones of syngeneic genomic DNA (on the order of 10 kb) should be isolated for recombination to work efficiently.

The ZFP technology can be used to rapidly analyze differential gene expression studies. Engineered ZFPs can be readily used to up or down-regulate any endogenous target gene. Very little sequence information is required to create a gene-specific DNA binding domain. This makes the ZFP technology ideal for analysis of long lists of poorly characterized differentially expressed genes. One can simply build a zinc finger-based DNA binding domain for each candidate gene, create chimeric up and down-regulating artificial transcription factors and test the consequence of up or down-regulation on the phenotype under study (transformation, response to a cytokine etc.) by switching the candidate genes on or off one at a time in a model system.

This specific example of using engineered ZFPs to add functional information to genomic data is merely illustrative. Any experimental situation that could benefit from the specific up or down-regulation of a gene or genes could benefit from the reliability and ease of use of engineered ZFPs.

Additionally, greater experimental control can be imparted by ZFPs than can be achieved by more conventional methods. This is because the production and/or function of an engineered ZFP can be placed under small molecule control. Examples of this approach are provided by the Tet-On system, the ecdysone-regulated system and a system incorporating a chimeric factor including a mutant progesterone receptor. These systems are all capable of indirectly imparting small molecule control on any endogenous gene of interest or any transgene by placing the function and/or expression of a ZFP regulator under small molecule control.

Transgenic Animals

A further application of the ZFP technology is manipulating gene expression in transgenic animals. As with cell lines, over-expression of an endogenous gene or the introduction of a heterologous gene to a transgenic animal, such as a transgenic mouse, is a fairly straightforward process. The ZFP technology is an improvement in these types of methods because one can circumvent the need for generating full-length cDNA clones of the gene under study.

Likewise, as with cell-based systems, conventional down-regulation of gene expression in transgenic animals is plagued by technical difficulties. Gene knockout by homologous recombination is the method most commonly applied currently. This method requires a relatively long genomic clone of the gene to be knocked out (ca. 10 kb). Typically, a selectable marker is inserted into an exon of the gene of interest to effect the gene disruption, and a second counter-selectable marker provided outside of the region of homology to select homologous versus non-homologous recombinants. This construct is transfected into embryonic stem cells and recombinants selected in culture. Recombinant stem cells are combined with very early stage embryos generating chimeric animals. If the chimerism extends to the germline homozygous knockout animals can be isolated by back-crossing. When the technology is successfully applied, knockout animals can be generated in approximately one year. Unfortunately two common issues often prevent the successful application of the knockout technology; embryonic lethality and developmental compensation. Embryonic lethality results when the gene to be knocked out plays an essential role in development This can manifest itself as a lack of chimerism, lack of germline transmission or the inability to generate homozygous back crosses. Genes can play significantly different physiological roles during development versus in adult animals. Therefore, embryonic lethality is not considered a rationale for dismissing a gene target as a useful target for therapeutic intervention in adults. Embryonic lethality most often simply means that the gene of interest can not be easily studied in mouse models, using conventional methods.

Developmental compensation is the substitution of a related gene product for the gene product being knocked out Genes often exist in extensive families. Selection or induction during the course of development can in some cases trigger the substitution of one family member for another mutant member. This type of functional substitution may not be possible in the adult animal. A typical result of developmental compensation would be the lack of a phenotype in a knockout mouse when the ablation of that gene's function in an adult would otherwise cause a physiological change. This is a kind of false negative result that often confounds the interpretation of conventional knockout mouse models.

A few new methods have been developed to avoid embryonic lethality. These methods are typified by an approach using the cre recombinase and lox DNA recognition elements. The recognition elements are inserted into a gene of interest using homologous recombination (as described above) and the expression of the recombinase induced in adult mice post-development. This causes the deletion of a portion of the target gene and avoids developmental complications. The method is labor intensive and suffers form chimerism due to non-uniform induction of the recombinase.

The use of engineered ZFPs to manipulate gene expression can be restricted to adult animals using the small molecule regulated systems described in the previous section. Expression and/or function of a zinc finger-based repressor can be switched off during development and switched on at will in the adult animals. This approach relies on the addition of the ZFP expressing module only; homologous recombination is not required. Because the ZFP repressors are trans dominant, there is no concern about germline transmission or homozygosity. These issues dramatically affect the time and labor required to go from a poorly characterized gene candidate (a cDNA or EST clone) to a mouse model. This ability can be used to rapidly identify and/or validate gene targets for therapeutic intervention, generate novel model systems and permit the analysis of complex physiological phenomena (development, hematopoiesis, transformation, neural function etc.). Chimeric targeted mice can be derived according to Hogan et al., *Manipulating the Mouse Embryo: A Laboratory Manual*, (1988); *Teratocarcinomas and Embryonic Stem Cell: A Practical Approach*, Robertson, ed., (1987); and Capecchi et al., *Science* 244:1288 (1989.

All publications and patent applications cited in this specification are herein incorporated by reference in their entireties, as if each individual publication or patent application were specifically and individually indicated to be incorporated by reference in its entirety.

EXAMPLES

The following examples are provided by way of illustration only and not by way of limitation. Those of skill in the art will readily recognize a variety of noncritical parameters that could be changed or modified to yield essentially similar results.

Example 1

ZFP-Targeted Gene Regulation: Genome-Wide Single Gene Specificity

A zinc finger protein transcription factor (ZFP TF) that can repress target gene expression with single-gene specificity within the human genome was generated and evaluated. The specificity of repression was determined, using DNA microarrays, and it was found that the ZFP TF repressed a single gene (CHK2) within the monitored genome, in two different cell types.

This example describes the use of ZFP TFs in the area of oncology, and specifically, on the emerging role of checkpoint kinase 2 (CHK2). CHK2 acts as a key integrator of DNA damage signals regulating cell cycle progression, DNA repair and cell death by phosphorylating a variety of substrates, including the p53 tumor suppressor protein (McGowan (2002) *Bioessays* 24:502-11; Bartek et al. (2001) *Nat Rev Mol Cell Biol* 2:877-86). Here it is shown that a designed ZFP TF targeted to a unique 18 bp recognition sequence in the promoter of the CHK2 gene (ZFP 5475) binds the intended site within chromatin and represses CHK2 transcription in vivo, providing a >10-fold reduction in chk2 mRNA and protein. This level of repression was sufficient to generate a functional phenotype, as demonstrated by the loss of DNA damage-induced CHK2-dependent p53 phosphorylation. Moreover, repression of CHK2 by this engineered ZFP TF occurs with remarkable specificity while simultaneously reducing CHK2 protein to levels that functionally ablate the action of this kinase. Finally, we show that constitutive expression of the ZFP TF in telomerase-immortalized untransformed human fibroblasts provides stable repression of the CHK2 gene, and results in loss of DNA damage-induced CHK2-dependent phosphorylation of p53 on Ser-20. These data demonstrate that ZFP TFs can be exquisitely specific yet potent repressors of gene expression, and therefore are potentially powerful reagents for target validation as well as therapeutic interventions in vivo.

A. Materials and Methods

Cell Culture

HEK293 cell line was obtained from ATCC. HEK293 T-REx and U2OS T-REx cell line were purchased from Invitrogen. Each line was maintained as recommended by the supplier.

Mapping of DNAse I Accessible Chromatin Regions in CHK2 Locus

Human HEK293 nuclei were treated with DNase I essentially as described in Liang et al. (2002) *J Biol Chem* 277: 20087-94. Genomic DNA isolation, restriction enzyme digestion, and Southern blot analysis were then carried out as described in Zhang et al. (2000) *J Biol Chem* 275:33850-60 and Liu et al. (2001) *J Biol Chem* 276:11323-34 except that the restriction enzymes and probe used were as indicated in FIG. 1.

Synthesis, Purification, and Gel Shift Analysis of Zinc Finger Proteins

A ZFP TF targeted to a pre-determined region in CHK2 gene was assembled by the linkage of three two-finger modules as described in Moore et al. (2001) *Proc Natl Acad Sci USA* 98:1437-41 and Moore et al. (2001) *Proc Natl Acad Sci USA* 98:1432-6. The amino acid sequence of this protein is shown in FIG. 6 (SEQ ID NO:27). A synthetic gene encoding this protein was constructed and cloned into the pMal-c2 plasmid (New England Biolabs, Beverly, Mass.) as a fusion with DNA encoding maltose-binding protein. Maltose-binding protein-ZFP fusions were then expressed and affinity-purified using an amylose resin (New England Biolabs). Binding studies were performed as described (Zhang et al. (2000) *J Biol Chem* 275:33850-60 and Liu et al. (2000) *J Biol Chem* 276:11323-34) except that the target site 5'-AC-CCGGGTTCCCCTCGGG-3' (SEQ ID NO:17) was incorporated into the DNA oligonucleotides.

Zinc Finger Protein Expression Constructs Used for Cell Culture Studies

For transient transfection studies, sequences encoding a ZFP-TF were cloned into a repression domain construct as described previously in Reynolds et al. (2003) *Proc Natl Acad Sci USA* 100: 1615-20. The protein encoded by the resulting construct, pTracer-ZFP-KOX1, contains an N-terminal ZFP DNA-binding domain, a nuclear localization signal PKKKRKV (SEQ ID NO: 28) from SV40 large T antigen, and the KOX1 repression domain. The ZFP portion of the protein was assembled from an archive of two finger modules described in Isalan et al. (2001) *Nat Biotechnol* 19:656-60, wherein the amino acid residues of the helical regions (from the −1 to +6 positions) responsible for specific DNA binding are; F1—RSDHLSR (SEQ ID NO: 1); F2—DNRDRTK (SEQ ID NO: 2); F3—DRKTLIE (SEQ ID NO: 3); F4—TSSGLSR (SEQ ID NO: 4); F5—RSDHLSE (SEQ ID NO: 5); and F6—TSSDRTK (SEQ ID NO: 6) respectively.

Cell Culture and Transient Transfections

HEK293 cells were grown in Dulbecco's modified eagle medium supplemented with 10% fetal bovine serum in a 5% $CO_2$ incubator at 37° C. For transfections, HEK293 cells were plated in 12-well plates at a density of 250,000 cells/well and transfected 1 day later using Lipofectamine 2000 reagent (Gibco-BRL, MD) according to manufacturers recommendations, using 9 μl of Lipofectamine 2000 reagent and 1.5 μg of ZFP plasmid DNA per well. The medium was removed and replaced with fresh medium 6-12 h after transfection. Transfection efficiency was assessed in each independent experiment via the use of a GFP expression plasmid control, in all experiments an apparent efficiency of 80-90% GFP positive cells was observed.

Retroviral Constructs, Virus Preparation and Generation of Stable Lines

A self inactivating retroviral vector containing a Tet inducible ZFP expression cassette was constructed and used for virus generation. Briefly, the pSIR vector (Clontech) was modified to contain the CMV promoter and the Tet operator sequences from pcDNA4-TO (Invitrogen). The coding region of ZFP-5475-KOX1 was inserted downstream of the inducible promoter by cloning into the modified pSIR vector (Clontech). Virus containing supernatant was generated by transient transfection of the resulting plasmid, pSIR-TO-ZFP-5475-KOX1, into the Phoenix packaging line as previously described in Pear et al. (1993) *Proc Natl Acad Sci USA* 90:8392-6. For generation of stable cell lines, HEK293 T-REx and U2OS T-REx cells were transduced with supernatant obtained above containing retrovirus encoding ZFP-5475-KOX1 and selected in medium containing 800 μg/ml of G418 (Invitrogen). Individual clones were isolated and analyzed for doxycycline-dependent expression of ZFP-KOX1 expression and corresponding repression of the endogenous gene target.

Quantitative RT-PCR Analysis of RNA Expression (TaqMan).

Cells were lysed and total RNA was prepared using the high pure RNA isolation kit (Roche) according to manufacturer's recommendations. Real-time quantitative RT-PCR analysis using TaqMan chemistry in a 96-well format on an ABI 7700 SDS machine (PerkinElmer Life Sciences) was done as described previously in Zhang et al. (2000) *J Biol Chem* 275:33850-60. The sequences of the primers and probes used for these analyses are shown in Table 1. The results were analyzed using SDS Version 1.6.3 software.

TABLE 1

Probe and primer sequences for RNA analysis

| Target Gene | OLIGO | SEQUENCE | SEQ ID NO |
|---|---|---|---|
| CHK2 mRNA detection | Forward | CCGAACATACAGCAAGAAACACTT | 29 |
| | Reverse | TCCATTGCCACTGTGATCTTCTA | 30 |
| | Probe | FAM-CGGATTTTCAGGGAAGTGGGTCCTAA-TAMRA | 31 |
| MDM2 mRNA detection | Forward | GCTGGAGTGCAGTGGGTGAT | 32 |
| | Reverse | TGACTGTAGGCCAAGCTAATTGG | 33 |
| | Probe | FAM-TTGGCTCACTGCAAGCTCTGCCCT-TAMRA | 34 |
| BAX mRNA detection | Forward | CCAGCAAACTGGTGCTCAAG | 35 |
| | Reverse | AGTCCAATGTCCAGCCCATGA | 36 |
| | Probe | FAM-CACCAAGGTGCCGGAACTGATCAGA-TAMRA | 37 |
| ZFP-TF mRNA detection | Forward | AGAGACCCATCCTGATTCAGA | 38 |
| | Reverse | AGCTCGGATCCTTACAGATCT | 39 |
| | Probe | FAM-CTGCATTTGAAATCAAATC-TAMRA | 40 |
| 18S RNA detection | Forward | TTCCGATAACGAACGAGACTCT | 41 |
| | Reverse | TGGGTGAACGCCACTTGTC | 42 |
| | Probe | FAM-TAACTAGTTACGCGACCCCCGAG-TAMRA | 43 |
| GAPDH mRNA detection | Forward | CCTTTTGCAGACCACAGTCCA | 44 |
| | Reverse | GCAGGGATGATGTTCTGGAGA | 45 |
| | Probe | FAM-CACTGCCACCCAGAAGACTGTGG-TAMRA | 46 |
| CHK2 promoter ChIP | Forward | AGCAAAGAGAGCGTCTAACCAGA | 47 |
| | Reverse | CCTCAATGCCTCCTGGGA | 48 |
| | Probe | FAM-CGGGTTCTAAGTTCCGCTCTCCCTTCTAAA-TAMRA | 49 |
| GAPDH ChIP | Forward | ACATCAAGAAGGTGGTGAAG | 50 |
| | Reverse | AGCTTGACAAAGTGGTCGTTG | 51 |
| | Probe | FAM-CACTGAGCACCAGGTGGTCTCCT-TAMRA | 52 |

Microarray Analysis

Global changes in gene expression were analyzed using an Affymetrix U133A GeneChip® array and Agilent GeneArray Scanner. RNA samples were prepared as per the manufacturer's recommendations. Data analysis to determine differentially expressed genes was carried out using Affymetrix GeneChip MAS5.0 and DMT13.0 software. The "Change Call" indicated does not relate to the P value; rather, for a probe set to be called "up" or "down," criteria of (i) a 2-fold difference in expression level between experiment and control, and (ii) a 100% confidence call were applied. For the HEK293 experiments, three independent single cell-derived clones were analyzed in duplicate with fold change determined using Affymetrix DMT3.0 statistical software and the "low signal log ratio" algorithm. For the U20S experiments, an individual single cell-derived clone was analyzed in duplicate, and fold change determined using Affymetrix DMT3.0 statistical software and the "signal log ratio" algorithm.

Immunoblot

Western blot analysis of protein expression was performed as previously described in Snowden et al. (2002) *Curr Biol* 12:2159-66, followed by immunoblotting using antibodies against CHK2 (cat no. 2391, ProSci Incorporated) and TFIIB (sc-225 Santa Cruz Biotech).

Chromatin Immunoprecipitation (ChIP)

Chromatin immunoprecipitation was performed using the CHIP assay kit according to the manufacturer's instructions (Upstate Biotechnology, NY) and as previously described Snowden et al. (2002) Curr Biol 12:2159-66, except that an anti-HA epitope tag antibody (sc-7392 Santa Cruz Biotechnology) was used throughout. Plasmids encoding HA-tagged constructs were assembled as previously described in Snowden et al. (2002) Curr Biol 12:2159-66. Sequences of primers and probes used in these analyses are given in Table 1.

hTERT-Immortalized Human Cells Studies

Human fibroblasts (strain 82-6) were obtained, cultured and immortalized with an hTERT-expressing retrovirus, as described in Kim et al. (1999) *Nat Genet* 23:405-12 and Rubio et al. (2002) *J Biol Chem* 277, 28609-17. The ZFP-5475 cDNA was subcloned into the pLXSN retroviral vector, infectious virus was produced, and hTERT-expressing cells were infected and selected as mass cultures. The cells were then plated at clonal densities, and single cell clones were expanded for analysis. Whole cell lysates were prepared and analyzed for the indicated proteins by immunoblotting, using commercially available antibodies that recognize CHK2 (Santa Cruz Biotechnologies), actin (Chemicon), p53 (Oncogene Research), and p53-Ser-20 (CellSignaling), as described in Kim et al. (1999) *Nat Genet* 23:405-12.

B. An Engineered ZFP TF Repressor of the Human CHK2 Gene

Engineered ZFP TFs can regulate the expression of endogenous genes in vivo (see, e.g., Jameison et al. (2003) *Nat Rev Drug Discov* 2:361-368 for recent review). To identify engineered ZFP TFs capable of controlling transcription of the CHK2 gene, we first mapped the chromatin architecture of the human CHK2 promoter to determine regions of "open" or accessible chromatin. FIG. 1A shows a schematic of the human CHK2 locus, indicating positions of the probe and restriction enzyme cutting sites used in the DNaseI hypersensitive site mapping experiment. Two accessible or hypersensitive (HS) sites were identified, designated HS1 and HS2 (FIG. 1B). HS1 contained the major start site of transcription, as determined by rapid amplification of cDNA ends (RACE). The sequence of the HS1 site was therefore used to design a novel 6-finger ZFP TF (ZFP-5475) recognizing the site 5'-ACCCGGGTTCCCCTCGGG-3' (SEQ ID NO: 17), and this ZFP was constructed from an archive of zinc finger DNA binding modules (Isalan et al. (2001) *Nat Biotechnol* 19:656-60). Importantly, this ZFP TF consisted of a string of three two-finger units, which was demonstrated to have increased specificity over more conventional polyzinc finger peptide units in vitro (Moore et al. (2001) *Proc Natl Acad Sci USA* 98:1437-41). See also WO 01/53480.

The in vitro DNA binding characteristics of this protein are shown in FIG. 1C. ZFP-5475 binds its intended target sequence with an apparent Kd of ~70 pM, a value that is similar to natural transcription factors (Greisman & Pabo (1997) *Science* 275:657-61). Furthermore, when linked to the Kruppel-associated box (KRAB A/B) repression domain (Margolin et al. (1994) *Proc Natl Acad Sci USA* 91:4509-13) from the N-terminal region of the KOX1 protein (Vissing et al. (1995) *FEBS Lett* 369:153-7), this ZFP decreased the level of CHK2 mRNA in a dose-dependent manner, achieving up to ~50% repression in transient transfection assays (FIG. 2A).

The repression of CHK2 mRNA levels depended on the KRAB A/B repressor domain because transfection of a construct expressing the DNA binding domain alone failed to repress CHK2 gene expression. Moreover, when the repressor domain was substituted with the p65 activation domain of NFkB (Ballard et al. (1992) *Proc Natl Acad Sci USA* 89:1875-9), levels of CHK2 mRNA increased.

To confirm that CHK2 repression resulted from a direct interaction between ZFP-5475 and its intended target site, chromatin immunoprecipitation (ChIP) analysis was performed. A ~65-fold enrichment of the CHK2 promoter fragment containing the ZFP TF binding site was observed in the presence of ZFP-5475 (HA-ZFP5475-KOX) relative to a control fragment from the GAPDH gene (FIG. 2B). Neither transfection with a plasmid encoding GFP-KOX, nor transfection with a plasmid encoding a non-specific ZFP TF, invoked a significant enrichment of the CHK2 promoter fragment. Moreover, in all cases, no enrichment of a control fragment at the p16 gene was observed. Thus this ZFP TF bound to the expected region of the CHK2 promoter in vivo.

Therefore, the engineered transcription factor ZFP-5475 binds to and regulates the expression of the CHK2 gene in vivo.

C. Regulatable and Reversible Repression of CHK2 in Stable Inducible Cell Lines

Figure 3:
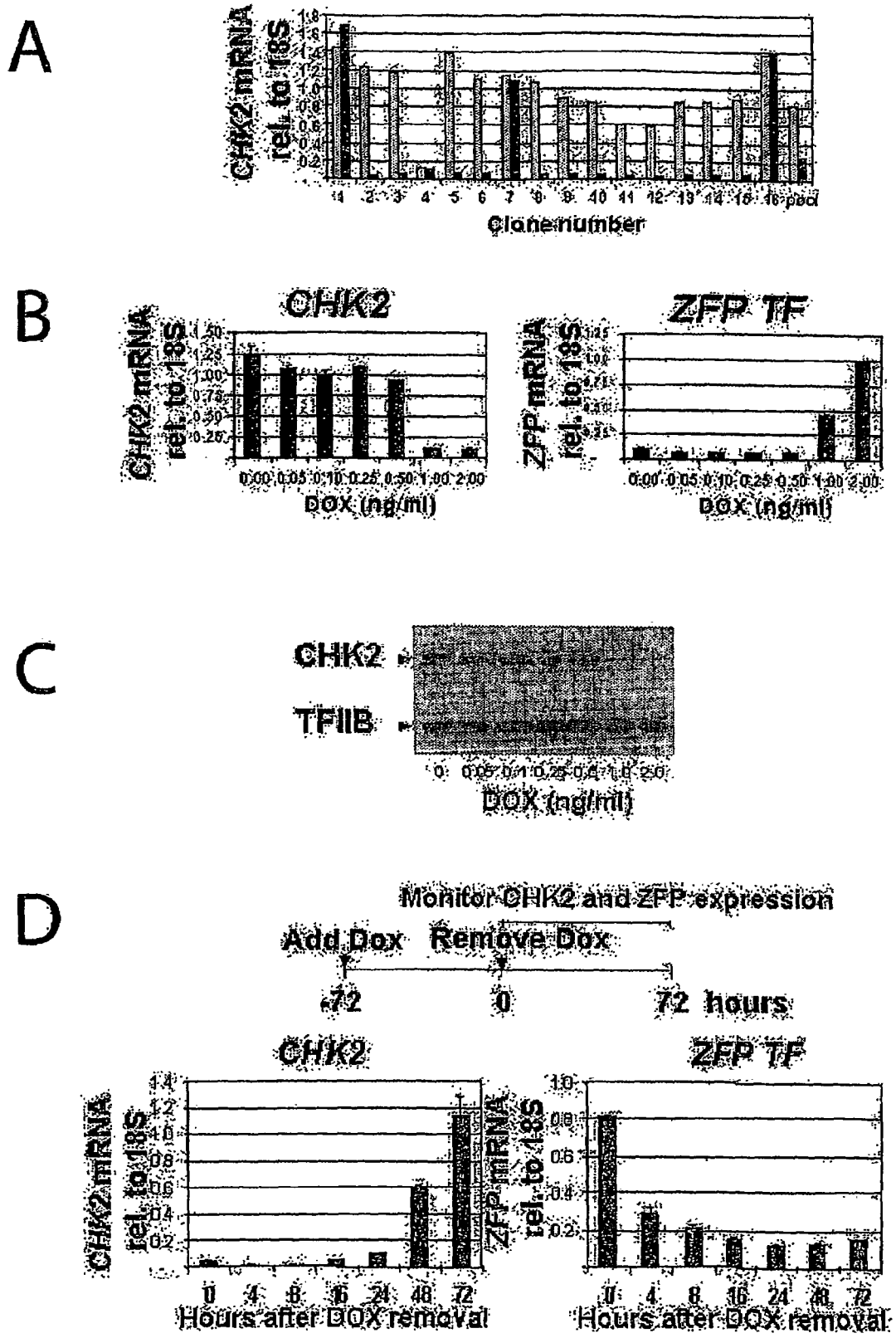
FIG. 3, panels A to D, depict regulatable expression of the ZFP TF drives inducible and reversible repression of CHK2.

To eliminate the contribution of untransfected cells in the transient transfection assays of repression, stable cell lines in which the T-REx system (Invitrogen) provided inducible expression of the ZFP TF were constructed. Vectors that placed ZFP TF expression under the control of a tetracycline operator (TetO)-regulated CMV promoter were created and introduced into HEK293 (HEK293 T-Rex) and U20S (U2OS T-Rex) cells by retroviral transduction. Single cell-derived clones were isolated and tested for doxycycline (DOX)-dependent repression of the CHK2 gene. The results from 16 HEK293 T-REx clones are shown in FIG. 3A.

The majority (12/16) of clones showed DOX-dependent repression of CHK2 mRNA levels, indicating a high frequency with which inducible repression was obtained. Moreover, most clones showed >10-fold repression, resulting in barely detectable CHK2 transcript levels. Of particular importance for the functional assays described below, mRNA levels of the related checkpoint kinase CHK1 (Shieh et al. (2000) *Genes Dev* 14: 289-300) were unaffected by ZFP induction. Target gene repression depended on the ZFP expression level, as the increasing ZFP mRNA levels obtained by increasing DOX concentrations correlated well with the degree of CHK2 repression at both the mRNA and protein levels (FIGS. 3B and 3C). Essentially identical results were obtained in U2OS T-REx clones, indicating that the results were not specific to a particular cell type (see below).

Figure 5:
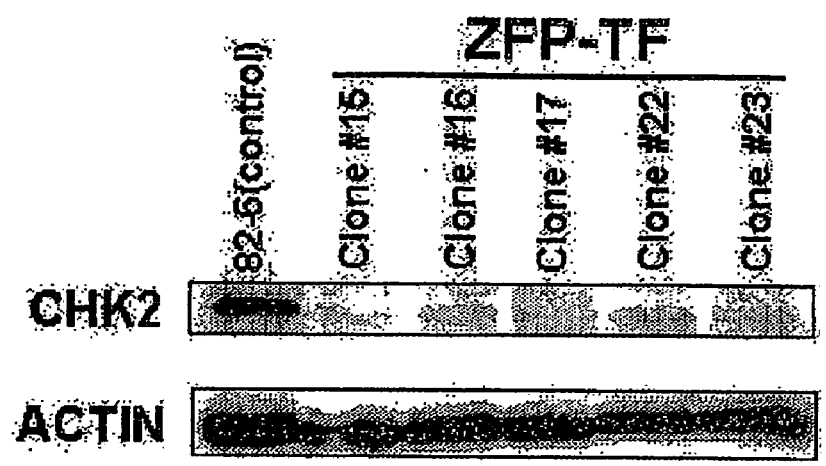
FIG. 5, panels A and B, are reproductions of blots and depict ZFP TF repression of CHK2 prevents the DNA-damage dependent phosphorylation of p53 at Serine 20.
Figure 5:
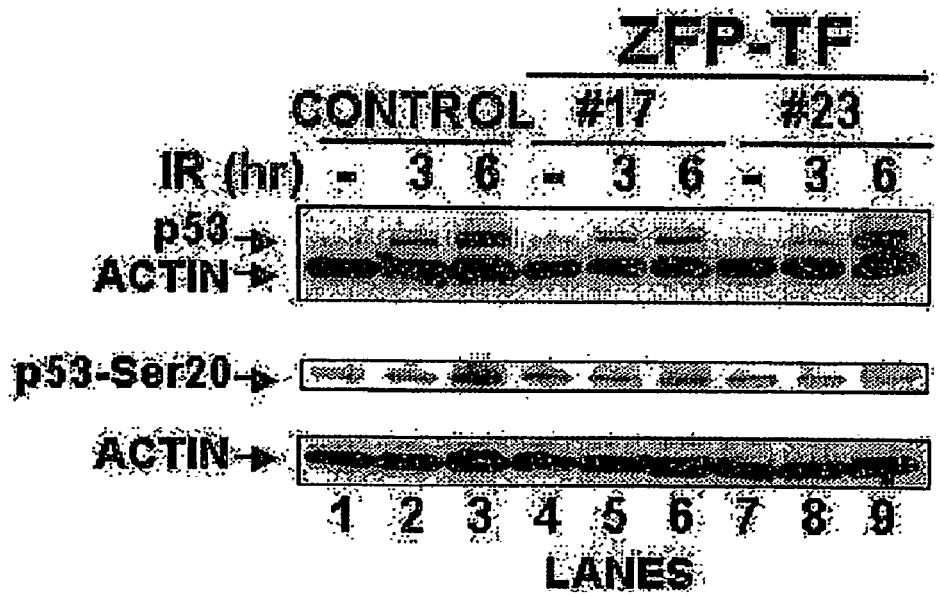
Figure 8:
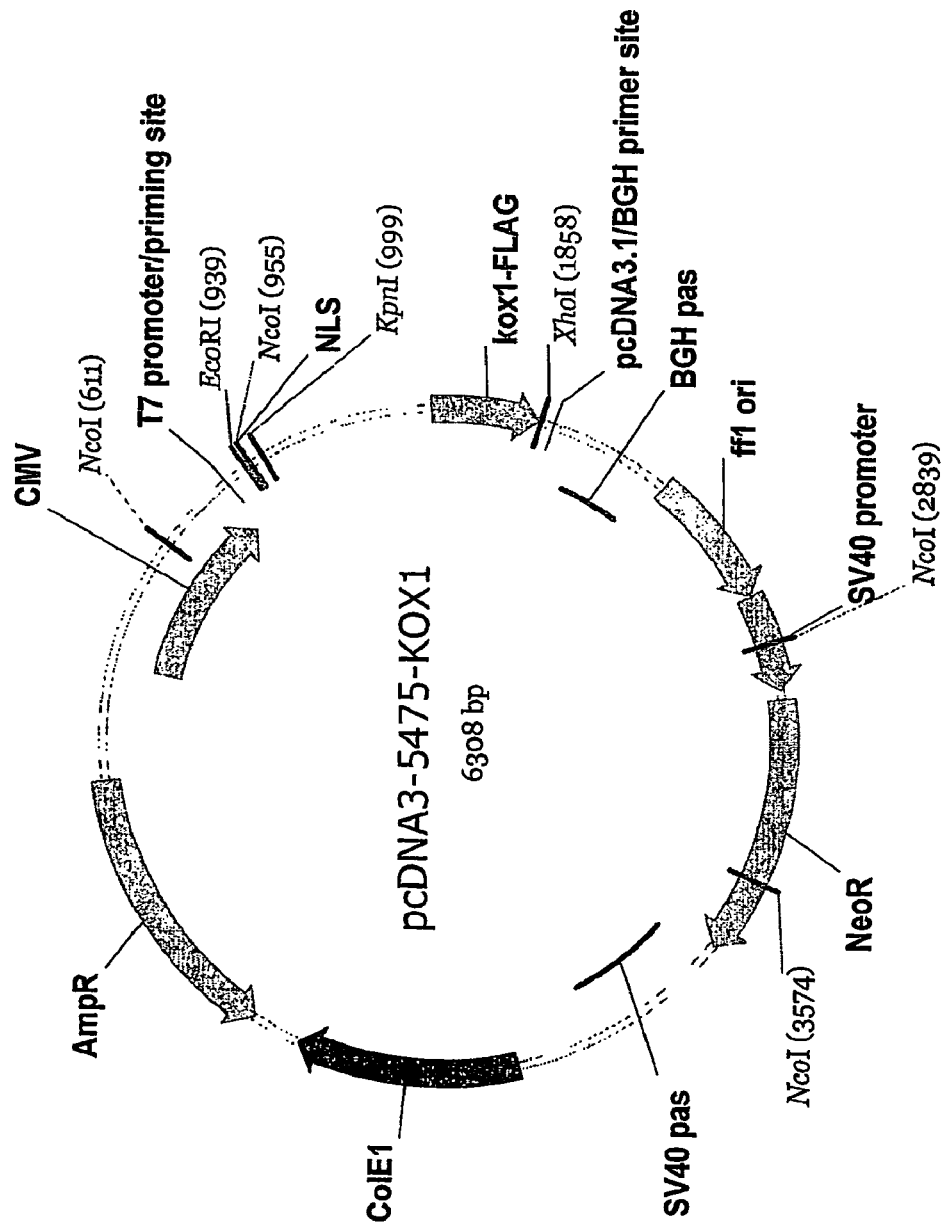
FIG. 8 is a schematic depiction of an exemplary zinc finger protein expression vector designated pcDNA3-5475-KOX1. The plasmid encodes the engineered zinc finger 5475 and a KOX1 functional domain (transcriptional repressor). Various regions are also designated, including restriction sites, CMV promoter, origins of replication, etc.

The growth characteristics of induced HEK293 T-Rex and U2OS T-Rex cells were indistinguishable from uninduced cells following approximately two weeks of culture. Moreover, repression of CHK2 was maintained throughout this period (see FIG. 5). These results indicate that cells tolerated persistent expression of the ZFP TF. Importantly, target gene repression required the continuous presence of the ZFP TF, as removing DOX from the culture medium reduced ZFP expression to background levels within ~24 hrs followed by recovery of CHK2 gene expression (FIG. 3D).

Taken together, these data demonstrate that the repression of target gene expression driven by the ZFP is dramatically effective (>10-fold repression) and is also stable, regulatable and reversible.

D. CHK2-Dependent p53 Function is Abolished Following ZFP Driven Repression

CHK2 is a cell cycle checkpoint kinase that phosphorylates a number of key regulators of cell proliferation in response to DNA damage, most notably p53 (see, e.g., Shieh et al. (2000) *Genes Dev* 14:289-300; Chehab et al. (2000) *Genes Dev* 14:278-88; Hirao et al. (2000) *Science* 287:1824-7). One consequence of CHK2-dependent p53 phosphorylation is an increase in p53 transactivation activity (Takai et al. (2002) *EMBO J* 21:5195-205). This increased activity is manifest by elevated expression of p53 target genes, such as MD2, BAX and p21. Indeed, cells from Chk2−/− mice fail to induce expression of these p53 targets following DNA damage by ionizing radiation (Takai et al. (2002) *EMBO J* 21:5195-205).

Figure 4:
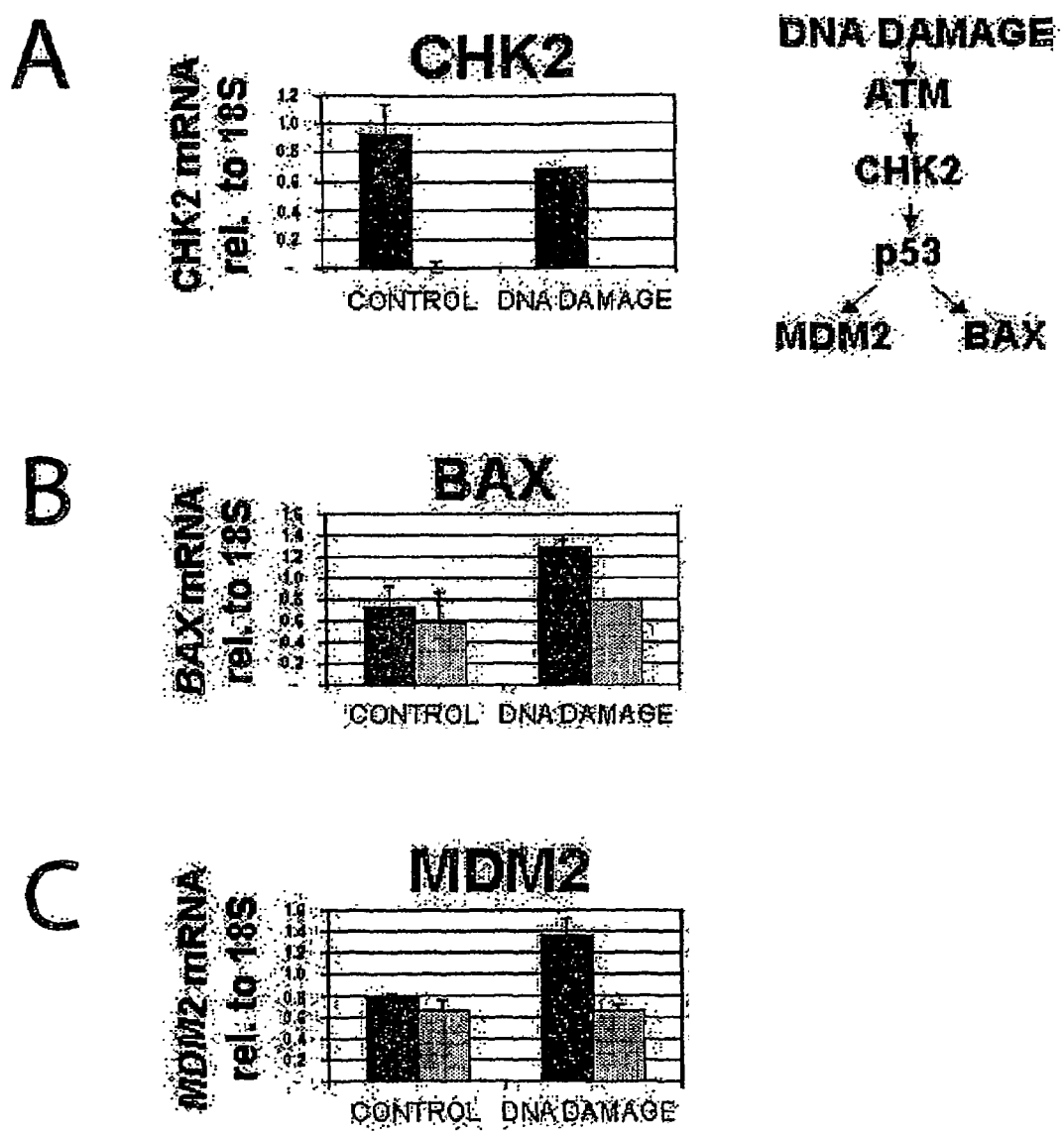
FIG. 4, panels A to C, are graphs showing that ZFP driven repression of CHK2 functionally eliminates the DNA damage dependent transactivation of p53. An isolated single cell-derived clone of U2OS T-REx transduced with a vector encoding inducible expression of the ZFP TF was cultured in the presence (grey bars) or absence (black bars) of DOX. 72 h after the addition of DOX, DNA damage was induced by addition of 10 uM camptothecin (DNA damage) or not (Control). mRNA levels were assayed 8 h post drug addition and are shown relative to 18S RNA levels as described in FIG. 2.

To confirm that the repression of CHK2 by the ZFP TF functionally abolished CHK2 activity, U2OS T-REx cells were challenged by a DNA damaging agent (camptothecin) in the presence or absence of the ZFP (i.e. in the presence or absence of DOX). Camptothecin is a topoisomerases I inhibitor, and was previously reported to stimulate a CHK2-dependent DNA damage response in cultured cells (Yu et al. *FEBS Lett* 505:7-12). As shown in FIG. 4, in uninduced cells lacking ZFP expression, camptothecin activated the p53-dependent DNA damage pathway, resulting in increased expression of BAX and MDM2. In contrast, induced cells, in which the ZFP repressed transcription of the CHK2 gene (FIG. 4A), failed to show a camptothecin-dependent increase in BAX and MDM2 expression 8 hrs after treatment (FIGS. 4B and 4C). Following 24 hrs of camptothecin treatment, however, activation of both MDM2 and BAX1 was observed in the ZFP TF cell line, but did not reach the levels observed for this line in the absence of DOX. These results are very similar to the results of comparable experiments performed with Chk2−/− mouse thymocytes (Takai et al. (2002) *EMBO J* 21:5195-205).

These data indicate that the CHK2 specific ZFP TF causes a functional CHK2 knock down phenotype similar to that obtained by genetic ablation of the CHK2 gene.

E. CBK2 is the Only Gene Repressed by ZFP-5475

The CHK2 specific ZFP TF repressor protein recognizes an 18 bp sequence that, theoretically, is sufficient to provide a unique address within the human genome. In this regard, the CHK2 gene target is an attractive test system for determining the genome wide specificity of ZFP TF because; (i) the site to which the ZFP TF binds is indeed unique within the human genome; and (ii) CHK2 must be phosphorylated by ataxia-telangiectasia mutated kinase (ATM) in order to become an active kinase capable of phosphorylating substrates such as p53 (Matsuoka et al. (2000) *Proc Natl Acad Sci USA* 97:10389-94; Melchionna et al. (2000) *Nat Cell Biol* 2:762-5; Ahn, J. Y., Schwarz, J. K., Piwnica-Worms, H. & Canman, C. E. (2000) *Cancer Res* 60, 5934-6). Thus, in undamaged cells, CHK2 remains unphosphorylated and to a first approximation inert, thereby eliminating possible downstream or secondary effects that might confound genome wide analyses of the specificity of ZFP TFs.

To test whether the designed ZFP TF indeed regulated a single gene (CHK2), the following studies were performed. Three different HEK293 T-REx clones, each demonstrating DOX inducible CHK2 repression, were analyzed for changes in gene expression in the presence (plus ZFP) or absence (minus ZFP) of DOX. Gene expression changes were determined using the Affymetrix U133A array, which provides information on 22,225 probe sets representing ~16,000 genes. The results were analyzed using Affymetrix GeneChip MAS5.0 and DMT3.0 software. For a probe set to be called "up" or "down" (Change Call) criteria of (i) a 2-fold difference in expression level between experiment and control, and (ii) a 100% confidence call were applied. The results of this analysis are shown in Table 2.

TABLE 2

Genes regulated by the CHK2 specific ZFP TF in HEK293 T-REx stable lines.

| # | PROBE SET | Fold Change (Down) | Confidence Call | P Value | Change Call | GENE NAME |
|---|---|---|---|---|---|---|
| 1 | 210416_s_at | 9.4 | 100 | <0.001 | Down | *Homo sapiens*, protein kinase hChk2 |
| 2 | 208739_x_at | 1.5 | 83 | 0.056 | None | *Homo sapiens* MIF2 suppressor (HSMT3) |
| 3 | 203012_x_at | 1.3 | 75 | 0.085 | None | *Homo sapiens* ribosomal protein L23a (RPL23A) |
| 4 | 201665_x_at | 1.3 | 75 | 0.192 | None | *Homo sapiens* ribosomal protein S17 (RPS17) |
| 5 | 206074_s_at | 2.5 | 66 | 0.009 | None | *Homo sapiens* high-mobility group protein isoforms I and Y (HMGIY) |
| 6 | 200817_x_at | 1.3 | 66 | 0.131 | None | *Homo sapiens* ribosomal protein S10 (RPS10), mRNA. |
| 7 | 208909_at | 1.3 | 66 | 0.068 | None | *Homo sapiens*, ubiquinol-cytochrome c reductase, |
| 8 | 208738_x_at | 1.3 | 66 | 0.23 | None | *Homo sapiens* cDNA: highly similar to HSSMT3B *Homo sapiens* mRNA |

TABLE 2-continued

Genes regulated by the CHK2 specific ZFP TF in HEK293 T-REx stable lines.

| # | PROBE SET | Fold Change (Down) | Confidence Call | P Value | Change Call | GENE NAME |
|---|---|---|---|---|---|---|
| 9 | 211765_x_at | 1.3 | 66 | 0.431 | None | Homo sapiens, peptidylprolyl isomerase A (cyclophilin A) |
| 10 | 212734_x_at | 1.3 | 66 | 0.01 | None | CLONE = IMAGE: 1745177 Hs.180842 ribosomal protein L13 |

The only gene that was identified as showing a "down change" (i.e. repression) in this analysis was the intended target, the human CHK2 gene. CHK2 mRNA was repressed ~10-fold, with a 100% confidence call and p value of <0.001. No other gene on the array was identified by the software as an "up" or "down" change.

To determine whether this result was peculiar to HEK293 T-Rex cells, the experiment was repeated using U2OS T-REx cells. Comparison of the genome-wide expression profiles of uninduced HEK293 T-REx and U2OS T-REx cells indicated that, of all the genes that were expressed (scored as "present" by the analysis software), ~30% were exclusive to one or other cell line. Despite this difference in uninduced gene expression, the expression of the ZFP TF in U2OS T-REx cells effected repression of only the CHK2 gene (Table 3).

human cell clones are wild type with respect to p53 function, and thus provide the opportunity to examine the downstream consequences of CHK2 repression in an untransformed human cell. Specifically, DNA damage induces p53 phosphorylation at both Ser15 and Ser20 (see Bartek et al. (2001) *Nat Rev Mol Cell Biol* 2:877-86), and data from Chk2−/− mice identified CHK2 as the kinase responsible for Ser20 phosphorylation.

To determine whether human CHK2 similarly phosphorylates p53 on Ser-20, control (infected with an insertless retrovirus) and ZFP TF transduced human cells were irradiated with 10 Gy of ionizing radiation (IR). Whole cell extracts were prepared 0, 3, and 6 h after IR and analyzed by immunoblotting. In response to IR, the cells stabilize p53 protein, as expected of cells with a normal DNA damage response

TABLE 3

Genes regulated by the CHK2 specific ZFP TF in the U2OS T-Rex stable line.

| # | PROBE SET | Fold Change (Down) | P Value | Change Call | GENE NAME |
|---|---|---|---|---|---|
| 1 | 210416_s_at | 7.1 | 0.003 | Down | Homo sapiens, protein kinase hChk2 mRNA |
| 2 | 205010_at | 1.9 | 0.058 | None | Homo sapiens hypothetical protein (FLJ10613) |
| 3 | 201085_s_at | 1.9 | 0.23 | None | Consensus includes SON DNA binding protein |
| 4 | 206074_s_at | 1.6 | 0.053 | None | Homo sapiens high-mobility group protein isoforms I and Y (HMGIY) |
| 5 | 211767_at | 1.6 | 0.1 | None | Homo sapiens similar to RIKEN cDNA 4933405K01 mRNA |
| 6 | 208993_s_at | 1.5 | 0.276 | None | Consensus includes peptidyl-prolyl isomerase G (cyclophilin G) |
| 7 | 201108_s_at | 1.5 | 0.092 | None | Consensus includes thrombospondin 1 |
| 8 | 208739_x_at | 1.4 | 0.006 | None | Homo sapiens MIF2 suppressor (HSMT3) |
| 9 | 215529_x_at | 1.4 | 0.842 | None | Consensus includes Homo sapiens mRNA DKFZp434G0572 |
| 10 | 205443_at | 1.3 | 0.076 | None | Homo sapiens small nuclear RNA activating complex mRNA |

Taken together, these data demonstrate that ZFP TFs can regulate target gene expression with single-gene specificity within the human genome. Moreover, this specificity was established in two different human cell types.

F. ZFP-5475 Functionally Abolishes CHK2 Expression in Telomerase-Immortalized Untransformed Human Fibroblasts To provide further functional validation of the CHK2-specific ZFP TF repressor, we used retroviruses to constitutively express ZFP-5475 in untransformed human fibroblasts that were immortalized by hTERT, the catalytic subunit of telomerase (Kim et al. (1999) *Nat Genet* 23:405-12). Several independent single cell-derived clones were obtained in which ZFP TF driven CHK2 repression was evident by immunoblot analysis (FIG. 5A). These immortalized untransformed (Chehab et al. (2000) *Genes Dev* 14:278-88) (FIG. 5B, top panel, lanes 1-3). Moreover, p53 became phosphorylated on Ser20, 6 h after irradiation (FIG. 5B, lower panel, lane 3), as expected (Hirao et al. (2000) *Science* 287:1824-7). In the ZFP TF expressing cells, the Ser20 phosphorylation signal was abolished (FIG. 5B lower panel, compare lanes 3 & 6 or 3 & 9). This result indicates that human CHK2 is necessary for the DNA damage dependent phosphorylation of p53 at Ser20. Interestingly, ablation of p53 Ser20 phosphorylation by CHK2 repression did not prevent damage-induced stabilization of p53 protein (FIG. 5B, top panel, compare lanes 3 & 6, or lanes 3 & 9). ATM phosphorylates p53 at Ser15 in response to DNA damage (Khanna et al. (1998) *Nat Genet* 20:398-400), and this phosphorylation partially blocks the interaction between p53 and MDM2, which promotes p53 degradation (Shieh et al. (1997) *Cell* 91:325-34). Thus, ATM dependent phosphorylation may stabilize p53 in the absence of CHK2, a result observed in Chk2−/− mouse cells (Takai et al. (2002) *EMBO J* 21:5195-205).

Therefore, in human fibroblasts, absence of CHK2 specifically abolishes phosphorylation of p53 at serine 20, but not p53 stabilization (FIG. 5A & FIG. 5B). Taken together, these data show that ZFP TFs can functionally repress target genes in untransformed human cells.

These data demonstrate the utility of ZFP TFs as precise tools for target validation, and highlight their potential as clinical therapeutics. Designed ZFP TFs can knock down the mRNA expression of a pre-determined target gene, while providing single-gene specificity (based on an analysis of ~16,000 human genes). Moreover, the extent of repression achieved by this highly specific engineered transcription factor was sufficient to abolish CHK2 function in two different assays and cell types. This degree of repression is all the more impressive given that the target gene, CHK2, encodes an enzymatic activity (protein kinase activity), for which even minimal residual protein might be expected to functionally compensate for incomplete repression. Indeed, recent data employing RNA interference or siRNA targeted to CHK2 in human cells reduced CHK2 protein by only ~60-75% (Ahn et al. (2003) *J Biol Chem* 24:24). ZFP TFs are thus shown to be a potent and highly specific alternative to siRNA-based approaches.

The remarkable biochemical specificity demonstrated in vivo herein, even when challenged with the complexity of a 3 billion bp genome, compares favorably to recent specificity and genome wide array data using siRNA (Jackson et al. (2003) *Nat Biotechnol* 18:18).

The potential therapeutic utility of ZFP TFs stems, in part, from the exquisite specificity of the ZFP DNA binding domain. This specificity, when combined with the potent yet reversible effects of the functional domain, will likely effect the success of these reagents in the clinic. As shown in this work, a single ZFP TF can be initially validated using transient transfection assays, and the same reagent can then be carried forward to more stringent tests of efficacy using stable-inducible cell lines, and untransformed human cells. See, also, Rebar et al. (2002) *Nat Med* 8:1427-32) describing in vivo animal studies with ZFP TFs. Finally, our data show that ZFP TFs can be constitutively expressed, thus providing stable, long-term target gene regulation. Taken together, these data demonstrate that ZFP TFs can be employed across species from cell lines through animal model settings for advanced experimental validation of therapeutic utility.

It will be readily apparent to one of ordinary skill in the art, in light of the teachings disclosed herein, that certain changes and modifications may be made thereto without departing from the spirit or scope of the present disclosure.

What is claimed is:

1. An isolated polynucleotide comprising a nucleic acid sequence encoding an engineered zinc finger protein, the engineered zinc finger protein comprising six zinc fingers, each zinc finger comprising a recognition region, wherein the amino acid sequence of the recognition regions, in amino- to carboxy-terminal order, are as follows: RSDHLSR (SEQ ID NO: 1); DNRDRTK (SEQ ID NO:2); DRKTLIE (SEQ ID NO:3); TSSGLSR (SEQ ID NO:4); RSDHLSE (SEQ ID NO:5); TSSDRTK (SEQ ID NO:6).

2. The polynucleotide of claim 1, wherein the target site is in a chk2 gene.

3. The polynucleotide of claim 1, further comprising a sequence encoding at least one functional domain.

4. The polynucleotide of claim 3, wherein the functional domain comprises a transcriptional activation domain.

5. The polynucleotide of claim 3, wherein the functional domain comprises a transcriptional repression domain.

6. The polynucleotide of claim 3, wherein the functional domain comprises a nuclease domain.

7. An isolated polypeptide encoded by the polynucleotide of claim 1.

8. A method of modulating expression of a chk2 gene in an isolated host cell; the method comprising administering a polynucleotide according to claim 3 to the host cell, wherein the polynucleotide expresses the zinc finger protein in the host cell and the zinc finger protein binds to the target site, thereby modulating the expression of the chk2 gene.

9. The method of claim 8, wherein expression of the single chk2 gene is repressed.

10. The method of claim 8, wherein expression of the single chk2 gene is activated.

* * * * *